(12) United States Patent
Finke et al.

(10) Patent No.: US 6,472,410 B1
(45) Date of Patent: Oct. 29, 2002

(54) N-CYCLOPENTYL MODULATORS OF CHEMOKINE RECEPTOR ACTIVITY

(75) Inventors: Paul E. Finke, Milltown; Kevin T. Chapman, Scotch Plains; Malcolm Maccoss, Freehold; Sander G. Mills, Scotch Plains; Jennifer L. Loebach, Westfield, all of NJ (US); Bryan Oates, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 11 days.

(21) Appl. No.: 09/590,318

(22) Filed: Jun. 8, 2000

Related U.S. Application Data
(60) Provisional application No. 60/139,078, filed on Jun. 11, 1999.

(51) Int. Cl.[7] .................. A61K 31/4468; A61K 31/454; C07D 211/58; C07D 401/08

(52) U.S. Cl. ........................ 514/329; 546/224; 546/210; 546/208; 514/326

(58) Field of Search ................................ 514/329, 326; 546/224, 210, 208

(56) References Cited

U.S. PATENT DOCUMENTS

| | | |
|---|---|---|
| 3,647,804 A | 3/1972 | Rynbrandt et al. |
| 4,105,666 A | 8/1978 | Ward |
| 4,281,132 A | 7/1981 | Ward |
| 5,169,844 A | 12/1992 | Commons et al. |
| 5,424,319 A | 6/1995 | Hanson et al. |
| 5,712,279 A | 1/1998 | Biller et al. |
| 5,750,549 A | 5/1998 | Caldwell et al. |
| 5,935,974 A | 8/1999 | Rae et al. |
| 6,054,468 A | 4/2000 | Geerts et al. |

FOREIGN PATENT DOCUMENTS

| | | |
|---|---|---|
| WO | WO 98/25617 | 6/1998 |
| WO | WO 98/31364 | 7/1998 |
| WO | WO 99/04794 | 2/1999 |
| WO | WO 99/09984 | 3/1999 |

OTHER PUBLICATIONS

Ko et al., "Preparation of N–ureidoalkyl–piperidines as modulators of chemokine receptor activity", Chemical Abstracts No. 133:43441, Abstract of WO 00/35449.

J. J. Gomez–Reino et al., "Association of Rheumatoid Arthritis with a Functional Chemokine Receptor, CCR5", Arthritis & Rheumatism, vol. 42, No. 5, May 1999, pp. 989–992.

T. J. Schall, "Biology of the Rantes/sis Cytokine Family", Cytokine, vol. 3, No. 3, May 1991, pp. 165–183.

P.M. Murphy, "The Molecular Biology of Leukocyte Chenoattractant Receptors", Annual Review of Immunology, vol. 12, 1994, pp. 593–633.

H. Deng et al., "Identification of a major co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.

A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote et al., "Molecular Cloning, Functional Expression, and Signaling Characteristics of C–C Chemokine Receptor", Cell, vol. 72, Feb. 1993, pp. 415–425.

C. Combadiere et al., "Cloning and Functional Expression of a Human Eosinophil CC Chemokine Receptor", J. Biol. Chem., vol. 270, No. 27, Jul. 1995, pp. 16491–16494.

C. A. Power et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.

M. Samson et al., "Molecular Cloning and Functional Expression of a New Human CC–Chemokine Receptor Gene", Biochemistry, vol. 35, 1996, pp. 3362–3367.

A. Chaudhuri et al., "Expression of the Duffy Antigen in K562 Cells,", J. Biol. Chem., vol. 269, No. 11, Mar. 1994, pp. 7835–7838.

H. Kita et al., "Chemokines Active on Eosinophils: Potential Roles in Allergic Inflammation", J. Exp. Med., vol. 183, Jun. 1996, pp. 2421–2426.

D. Smith et al., "Blocking of HIV–1 Infectivity by a Soluble, Secreted Form of the CD4 Antigen", Science, vol. 238, 1987, pp. 1704–1707.

J. A. Levy, "Infection by Human Immunodeficiency Virus— CD4 is not Enough", N. Eng. J. Med., vol. 335, No. 20, Nov. 1996, pp. 1528–1530.

(List continued on next page.)

*Primary Examiner*—Charanjit S. Aulakh
(74) *Attorney, Agent, or Firm*—Kenneth R. Walton; Valerie J. Camara; Richard S. Parr

(57) ABSTRACT

The present invention is directed to compounds of the formula I:

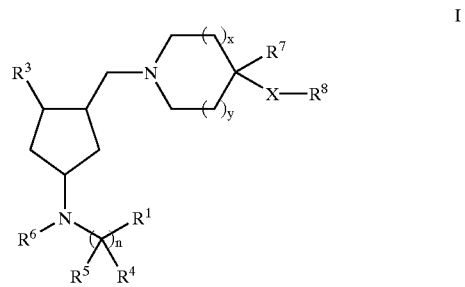

(wherein $R^1$, $R^3$, $R^4$, $R^5$, $R^6$, $R^7$, $R^8$, X, n, x and y are defined herein) which are useful as modulators of chemokine receptor activity. In particular, these compounds are useful as modulators of the chemokine receptors CCR-5 and/or CCR-3.

31 Claims, No Drawings

OTHER PUBLICATIONS

T. Dragic et al., "HIV–1 entry into CD4+ cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistance to HIV–1 infection in caucasian individuals bearing mutant alleles of the CCR–5 cehmokine receptor gene", Nature, vol. 382, Aug. 1996, pp. 722–725.

C. M. Hill et al., "Natural resistance to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

N-CYCLOPENTYL MODULATORS OF CHEMOKINE RECEPTOR ACTIVITY

This application claims the benefit of U.S. Provisional Application No. 60/139,078, filed Jun. 11, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C—X—C (α) and C—C (β), depending on whether the first two cysteines are separated by a single amino acid (C—X—C) or are adjacent (C—C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR4" or "CC-CKR-4") [MIP-1α, RANTES, MCP-1] (Power, et al., *J. Biol. Chem.*, 270, 19495–19500 (1995)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-m, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

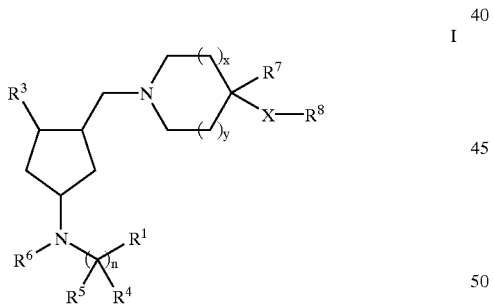

wherein:

X is —($C_{0-2}$ alkyl)—Y—($C_{0-6}$ alkyl)—,
  where the alkyl is unsubstituted or substituted with 1–7 substituents where the substituents are independently selected from:
  (a) halo,
  (b) hydroxy,
  (c) —O—$C_{1-3}$ alkyl, and
  (d) trifluoromethyl,
  where Y is selected from:
    —(CO)—, —(CO)O—, —O(CO)—, —(CO)$NR^9$—, —$NR^9$(CO)—, —O(CO)$NR^9$—, —$NR^9$(CO)O—, and —$NR^9$(CO)$NR^{10}$—,
  where $R^9$ is independently selected from: hydrogen, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and where $R^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl, or where $R^9$ and $R^{10}$ may be joined together to form a 5–8 membered ring which may be unsubstituted or substituted with halo, $C_{1-3}$ alkyl, and $C_{1-3}$ alkoxy;

$R^1$ is selected from:
  (1) —$CO_2H$,
  (2) —$NO_2$,
  (3) -tetrazolyl,
  (4) -hydroxyisoxazole,
  (5) —$SO_2NHCO$—($C_{0-3}$ alkyl)—$R^9$, and
  (6) —$P(O)(OH)_2$;

$R^3$ is selected from the group consisting of:
  phenyl and heterocycle, which is unsubstituted or substituted with 1–7 substituents where the substituents are independently selected from:
  (a) halo,
  (b) trifluoromethyl,
  (c) hydroxy,
  (d) $C_{1-3}$ alkyl,
  (e) —O—$C_{1-3}$ alkyl,
  (f) —$CO_2R^9$,
  (g) —$NR^9R^{10}$, and
  (h) —$CONR^9R^{10}$;

$R^4$, $R^5$ and $R^6$ are independently selected from:
  hydrogen, $C_{1-10}$ alkyl, $C_{3-8}$ cycloalkyl, $C_{2-10}$ alkenyl, $C_{2-10}$ alkynyl, phenyl, —($C_{1-6}$ alkyl)-phenyl, —($C_{1-6}$ alkyl)-$C_{3-8}$ cycloalkyl, naphthyl, biphenyl, and heterocycle, which is unsubstituted or substituted with 1–7 of $R^{11}$ where $R^{11}$ is independently selected from:
  (a) halo,
  (b) trifluoromethyl,
  (c) hydroxy,
  (d) $C_{1-3}$ alkyl,
  (e) —O—$C_{1-3}$ alkyl,
  (f) —$CO_2R^9$,
  (g) —$NR^9R^{10}$, and
  (h) —$CONR^9R^{10}$, or where $R^4$ and $R^5$ may be joined together to form a 3–8 membered saturated ring which may be unsubstituted or substituted with 1–7 of $R^{11}$,
or where $R^5$ and $R^6$ may be joined together to form a 3–8 membered saturated ring which may be unsubstituted or substituted with 1–7 of $R^{11}$;

$R^7$ is selected from:
  (1) hydrogen,
  (2) $C_{1-6}$ alkyl, which is unsubstituted or substituted with 1–4 substituents where the substituents are independently selected from: hydroxy, cyano, and halo,
  (3) hydroxy, and
  (4) halo;

$R^8$ is selected from:
  hydrogen, phenyl, naphthyl, biphenyl, and heterocycle, which is unsubstituted or substituted with 1–7 of $R^{12}$ where $R^{12}$ is independently selected from:

(a) halo,
(b) cyano,
(c) hydroxy,
(d) $C_{1-6}$ alkyl, which is unsubstituted or substituted with 1–5 of $R^{13}$ where $R^{13}$ is independently selected from: halo, cyano, hydroxy, $C_{1-6}$ alkoxy, $-CO_2H$, $-CO_2(C_{1-6}$ alkyl), phenyl, trifluoromethyl, and $-NR^9R^{10}$,
(e) $-O-C_{1-6}$ alkyl, which is unsubstituted or substituted with 1–5 of $R^{13}$,
(f) $-CF_3$,
(g) $-CHF_2$,
(h) $-CH_2F$,
(i) $-NO_2$,
(j) phenyl,
(k) $-CO_2R^9$,
(l) tetrazolyl,
(m) $-NR^9R^{10}$,
(n) $-NR^9-COR^{10}$,
(o) $-NR^9-CO_2R^{10}$,
(p) $-CO-NR^9R^{10}$,
(q) $-OCO-NR^9R^{10}$,
(r) $-NR^9CO-NR^9R^{10}$,
(s) $-S(O)_m-R^9$, wherein m is an integer selected from 0, 1 and 2,
(t) $-S(O)_2-NR^9R^{10}$,
(u) $-NR^9S(O)_2-R^{10}$, and
(v) $-NR^9S(O)_2-NR^9R^{10}$;

n is an integer selected from 1, 2, 3 and 4;

x is an integer selected from 0, 1 and 2, and y is an integer selected from 0, 1 and 2, with the proviso that the sum of x and y is 2;

and pharmaceutically acceptable salts thereof and individual diastereomers thereof.

One embodiment of the present invention is a compound of Formula I, wherein $R^1$ is selected from:
(1) $-CO_2H$,
(2) $-NO_2$,
(3) -tetrazolyl,
(4) -hydroxyisoxazole, and
(5) $-P(O)(OH)_2$;

and all other variables are as previously defined;
and pharmaceutically acceptable salts thereof and individual diastereomers thereof.

Preferred compounds of the present invention include those of formula

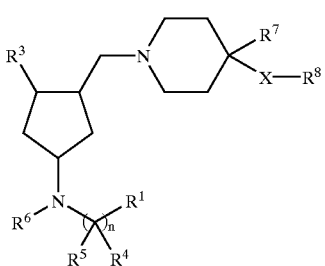

wherein $R^1$, $R^3$, $R^4$, $R^5$, $R^6$, $R^7$, $R^8$, X and n are defined herein;
and pharmaceutically acceptable salts and individual diastereomers thereof.

More preferred compounds of the present invention include those of formula Ic:

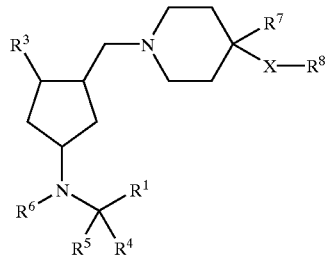

wherein $R^1$, $R^3$, $R^4$, $R^5$, $R^6$, $R^7$, $R^8$ and X are defined herein;
and pharmaceutically acceptable salts and individual diastereomers thereof.

Highly preferred compounds of the present invention include those of formula Id:

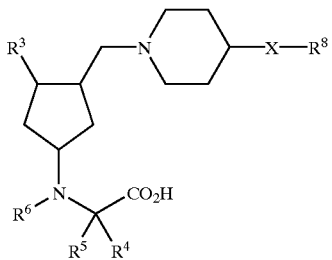

wherein $R^3$, $R^4$, $R^5$, $R^6$, $R^8$ and X are defined herein;
and pharmaceutically acceptable salts and individual diastereomers thereof.

More highly preferred compounds of the present invention include those of formula Ie:

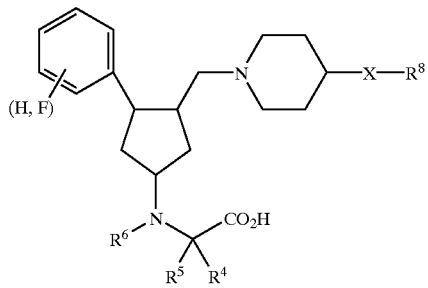

wherein $R^4$, $R^5$, $R^6$, $R^8$ and X are defined herein;
and pharmaceutically acceptable salts and individual diastereomers thereof.

In the present invention it is preferred that $R^1$ is selected from:
(1) $-CO_2H$,
(2) $-P(O)(OH)_2$, and
(3) -tetrazolyl.

In the present invention it is more preferred that $R^1$ is selected from:
(1) $-CO_2H$, and
(2) -tetrazolyl.

In the present invention it is even more preferred that $R^1$ is $-CO_2H$.

In the present invention it is preferred that $R^3$ is selected from the group consisting of:
phenyl and thienyl, which may be unsubstituted or substituted with 1–5 substituents where the substituents are independently selected from:

(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl, which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl.

In the present invention it is even more preferred that $R^3$ is selected from the group consisting of:
phenyl, which may be unsubstituted or substituted with 1–5 substituents where the substituents are independently selected from:
(a) fluoro, and
(b) chloro; and unsubstituted thienyl.

In the present invention it is still more preferred that $R^3$ is unsubstituted phenyl, (3-fluoro)phenyl or 3-thienyl.

In the present invention it is preferred that $R^4$ is hydrogen or $C_{1-6}$ alkyl.

In the present invention it is more preferred that $R^4$ is hydrogen.

In the present invention it is preferred that $R^5$ is selected from: hydrogen, $C_{1-6}$ alkyl, $C_{3-8}$ cycloalkyl, $C_{1-6}$ alkyl-$C_{3-8}$ cycloalkyl, and phenyl.

In the present invention it is more preferred that $R^5$ is selected from: hydrogen, methyl, n-propyl, isopropyl, n-butyl, t-butyl, isobutyl, sec-butyl, cyclohexyl, —$CH_2$-cyclopropyl, —$CH_2$-cyclobutyl, and phenyl.

In the present invention it is still more preferred that $R^5$ is selected from: isopropyl, isobutyl, sec-butyl, and cyclohexyl.

In the present invention it is preferred that $R^6$ is selected from: hydrogen, $C_{1-6}$ alkyl, $C_{3-8}$ cycloalkyl, $C_{1-6}$ alkyl-$C_{3-8}$ cycloalkyl, and phenyl.

In the present invention it is more preferred that $R^6$ is selected from: hydrogen, methyl, n-butyl, t-butyl, isobutyl, sec-butyl, —$CH_2$-cyclopropyl, —$CH_2$-cyclobutyl, and cyclohexyl.

In the present invention it is still more preferred that $R^6$ is selected from: hydrogen, methyl, —$CH_2$-cyclopropyl, —$CH_2$-cyclobutyl, and cyclohexyl.

In an alternate embodiment of the present invention it is preferred that $R^5$ and $R^6$ are joined together to form a $C_{3-8}$ cycloalkyl ring.

In an alternate embodiment of the present invention it is more preferred that $R^5$ and $R^6$ are joined together to form a pyrrolidine ring.

In the present invention it is preferred that $R^7$ is hydrogen, fluoro, hydroxy or $C_{1-6}$ alkyl.

In the present invention it is more preferred that $R^7$ is hydrogen or fluoro.

In the present invention it is even more preferred that $R^7$ is hydrogen.

In the present invention it is preferred that X is: —($CO_{0-2}$ alkyl)—Y—($C_{0-4}$ alkyl)—,
where the alkyl is unsubstituted or substituted with 1–7 substituents where the substituents are independently selected from:
(a) halo,
(b) hydroxy,
(c) —O—$C_{1-3}$ alkyl, and
(d) trifluoromethyl,
where Y is selected from: —(CO)$NR^9$—, —$NR^9$(CO)—, —O(CO)$NR^9$—, —$NR^9$(CO)O—, and —$NR^9$(CO)$NR^{10}$—,
where $R^9$ is independently selected from: hydrogen, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
and where $R^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl,
or where $R^9$ and $R^{10}$ may be joined together to form a 5–8 membered ring which is unsubstituted.

In the present invention it is more preferred that X is: —Y—($C_{0-4}$ alkyl)—,
where the alkyl is unsubstituted,
where Y is selected from: —O(CO)$NR^9$—, —$NR^9$(CO)O—, and —$NR^9$(CO)$NR^{10}$—,
where $R^9$ is independently selected from: hydrogen, $C_{1-10}$ alkyl, $C_{2-10}$ alkenyl, and $C_{1-6}$ alkyl-$C_{3-6}$ cycloalkyl,
where $R^{10}$ is independently selected from: hydrogen and $C_{1-6}$ alkyl,
or where $R^9$ and $R^{10}$ may be joined together to form a 5–8 membered ring which is unsubstituted.

In the present invention it is even more preferred that X is selected from:
—(CO)$NR^9$—, —(CO)$NR^9CH_2$—, —$NR^9$(CO)O—, —$NR^9$(CO)O$CH_2$—, —$NR^9$(CO)$NR^{10}$—, and —$NR^9$(CO)$NR^{10}CH_2$—,
where $R^9$ is independently selected from: hydrogen, $C_{1-10}$ alkyl, $C_{2-10}$ alkenyl, and $C_{1-6}$ alkyl-$C_{3-6}$ cycloalkyl,
where $R^{10}$ is independently selected from: hydrogen and $C_{1-6}$ alkyl,
or where $R^9$ and $R^{10}$ may be joined together to form a 5–8 membered ring which is unsubstituted.

In an aspect of the preceding embodiment, in the present invention it is even more preferred that X is selected from:
—(CO)$NR^9$—, —$NR^9$(CO)O—, and —$NR^9$(CO)$NR^{10}$—,
where $R^9$ is independently selected from: hydrogen, $C_{1-10}$ alkyl, $C_{2-10}$ alkenyl, and $C_{1-6}$ alkyl-$C_{3-6}$ cycloalkyl,
where $R^{10}$ is independently selected from: hydrogen and $C_{1-6}$ alkyl,
or where $R^9$ and $R^{10}$ may be joined together to form a 5–8 membered ring which is unsubstituted.

In the present invention it is still more preferred that X is selected from:
—$NR^9$(CO)O—, —$NR^9$(CO)O$CH_2$—, —$NR^9$(CO)NH—, and —$NR^9$(CO)NH$CH_2$—,
where $R^9$ is independently selected from: methyl, ethyl, n-propyl, allyl, and—$CH_2$-cyclopropyl.

In an aspect of the preceding embodiment, in the present invention it is still more preferred that X is selected from:
—$NR^9$(CO)O—, and —$NR^9$(CO)NH—,
where $R^9$ is independently selected from: methyl, ethyl, n-propyl, allyl, and—$CH_2$-cyclopropyl.

In the present invention it is preferred that $R^8$ is hydrogen or phenyl, which is unsubstituted or substituted with 1–7 substituents where the substituents are independently selected from:

(a) halo,
(b) cyano,
(c) hydroxy,
(d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, phenyl, —$CO_2(C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;
(e) —O—$C_{1-6}$ alkyl, which is unsubstituted or substituted with 1–5 of $R^{13}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$ In the present invention it is more preferred that $R^8$ is phenyl which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) tetrazolyl,
(h) $C_{1-6}$ alkyl, which is unsubstituted or substituted with phenyl, and
(i) —O—$C_{1-6}$ alkyl.

In the present invention it is even more preferred that $R^8$ is phenyl, which is unsubstituted or substituted with 1–3 substituents where the substituents are independently selected from:
(a) fluoro,
(b) chloro,
(c) cyano,
(d) —$NO_2$,
(e) $C_{1-6}$ alkyl, which is unsubstituted or substituted with phenyl, and
(f) —$CF_3$.

In the present invention it is still more preferred that $R^8$ is selected from: phenyl, 4-chlorophenyl, 2-fluorophenyl, 3-fluorophenyl, 4-fluorophenyl, 2,4-difluorophenyl, 3,4-difluorophenyl, 3,5-difluorophenyl, 4-methylphenyl, 3-nitrophenyl, 4-nitrophenyl, and 4-trifluoromethylphenyl.

In the present invention it is preferred that n is an integer selected from 1,2 and 3.

In the present invention it is more preferred that n is an integer which is 1.

In the present invention it is preferred that x is an integer which is 1 and y is an integer which is 1.

It is to be understood that embodiments of the present invention include, but are not limited to, compounds of formula I wherein $R^1$, $R^3$, $R^4$, $R^5$, $R^6$, $R^7$, $R^8$, X, n, x, and y are defined in accordance with one of the embodiments or aspects thereof as set forth above. Any and all possible combinations of preferred, more preferred, even more preferred, highly preferred, more highly preferred, and most preferred definitions of these variables in formulas I are within the scope of the present invention.

The compounds of the instant invention have at least two asymmetric centers at the ring junction of the substitutents bearing the piperidine and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

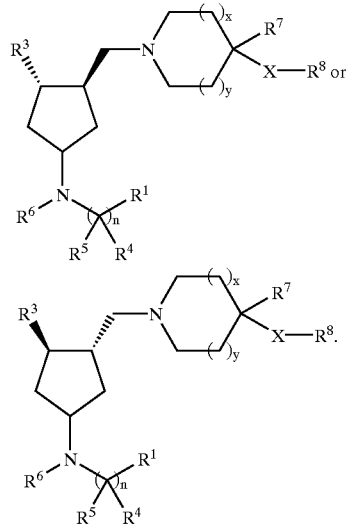

The relative configurations of the even more preferred compounds of this invention wherein $R^6$ is hydrogen, methyl or wherein $R^5$ and $R^6$ form a pyrrolidine ring with respect to the configuration of the nitrogen substituent on the cyclopentane ring is cis to the orientation of $R^3$ as depicted:

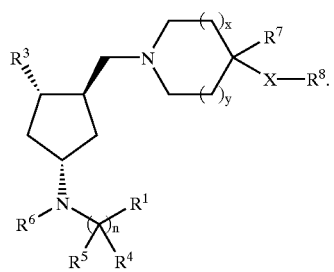

The relative configurations of the most preferred compounds of this invention wherein $R^6$ is hydrogen or methyl with respect to the configuration of the nitrogen substituent on the cyclopentane ring is is cis to the orientation of $R^3$ and with the (R)-stereochemistry of the nitrogen side chain of the orientation as depicted:

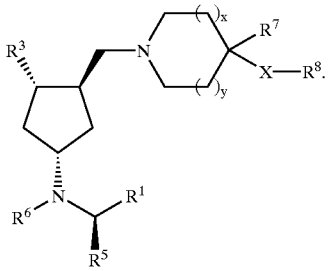

The relative configurations of the even more preferred compounds of this invention wherein $R^6$ is other than hydrogen or methyl with respect to the configuration of the nitrogen substituent on the cyclopentane ring is 1,3-cis of the orientation as depicted:

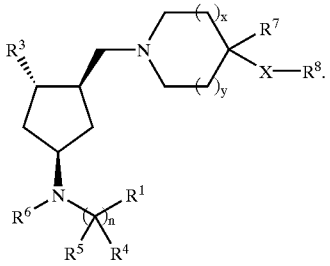

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression ". . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1–3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri- substituted phenyl.

Exemplifying the invention is the use of the compounds disclosed in the Examples and herein.
Specific compounds within the present invention include a compound which is selected from the group consisting of:
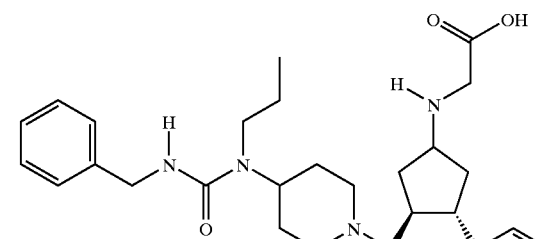
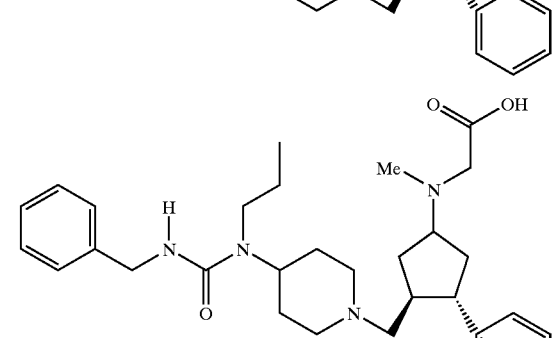
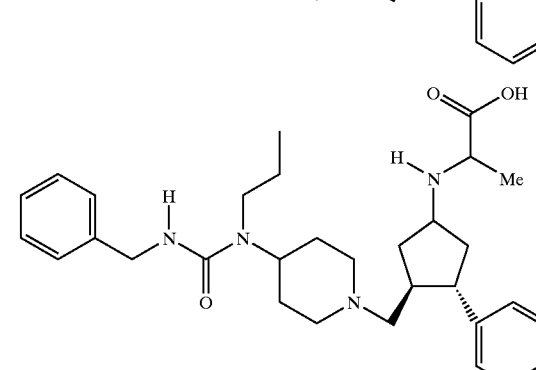
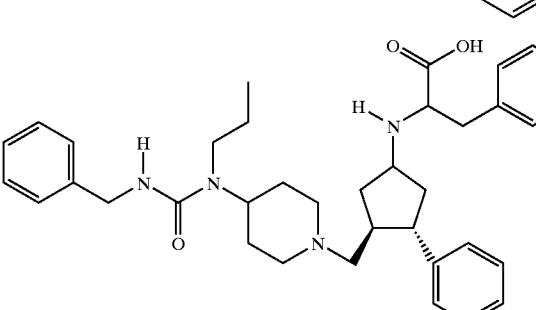
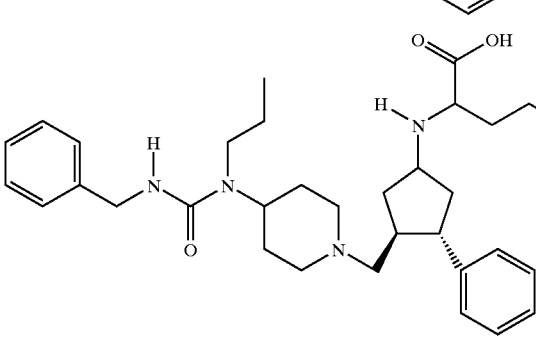
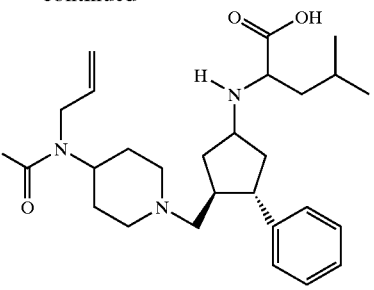
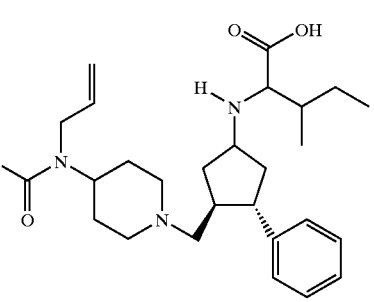
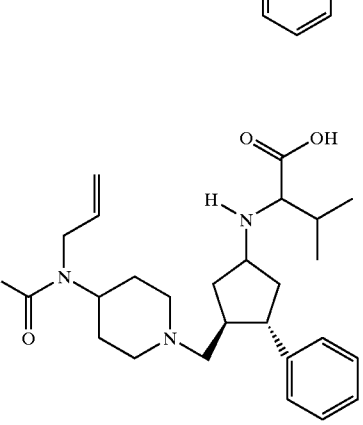
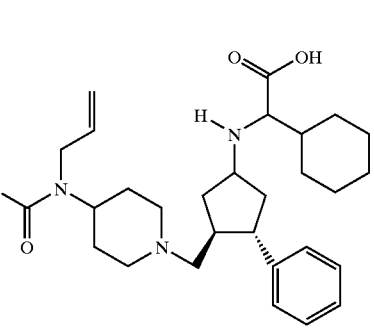
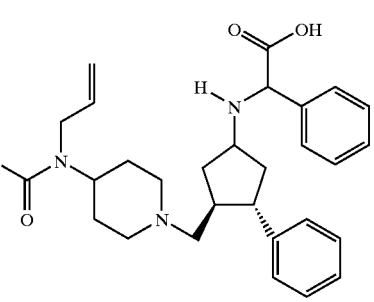

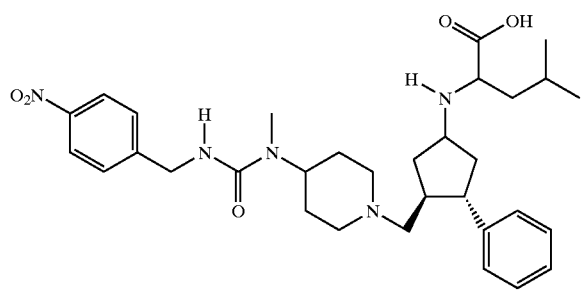
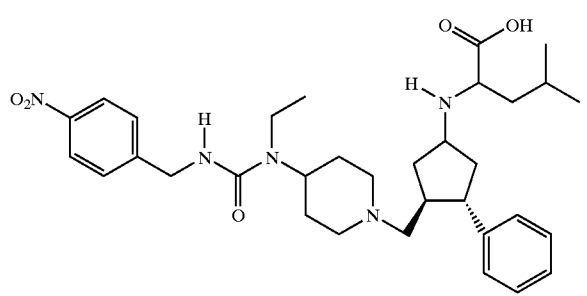
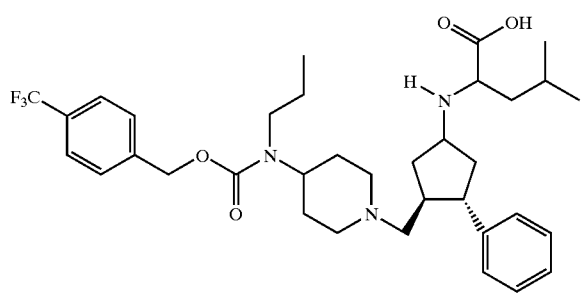
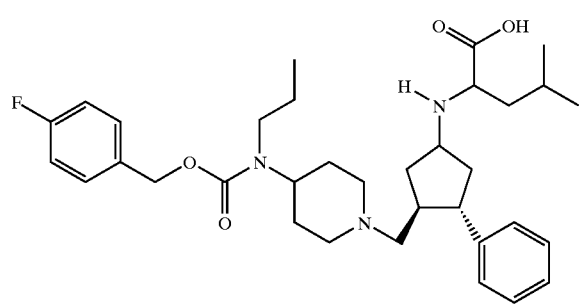
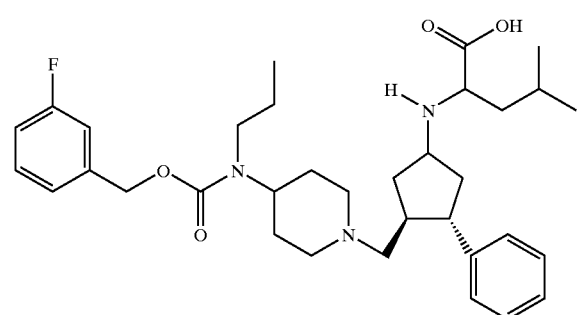
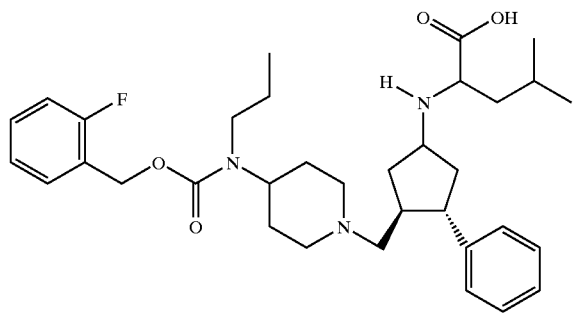
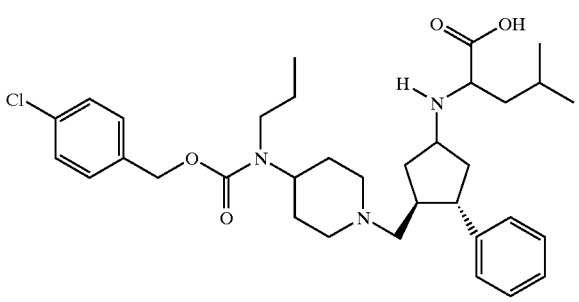
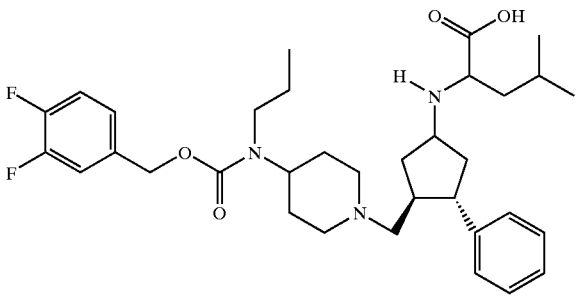
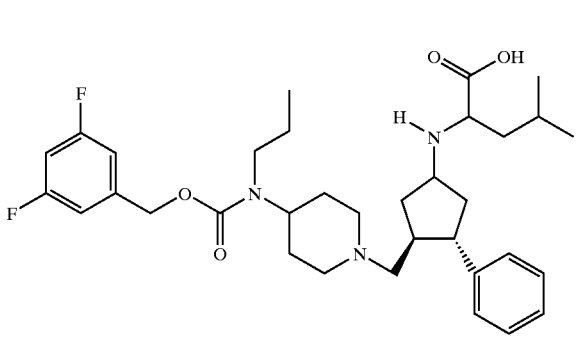
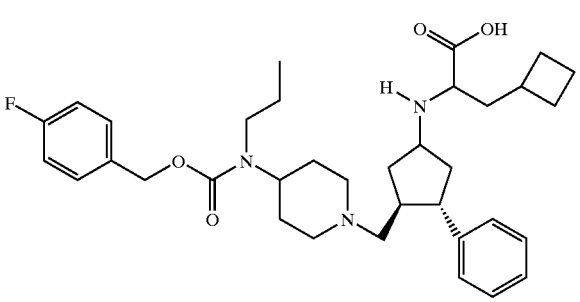

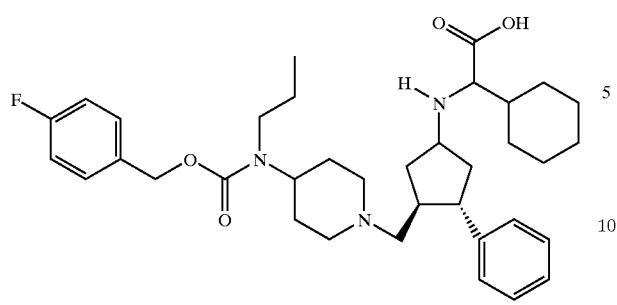
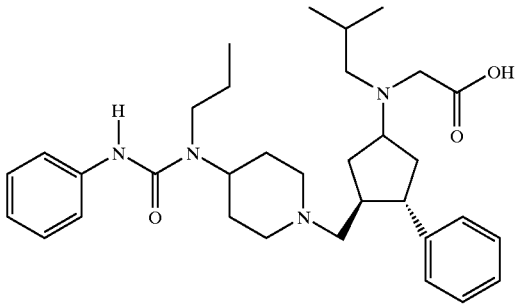
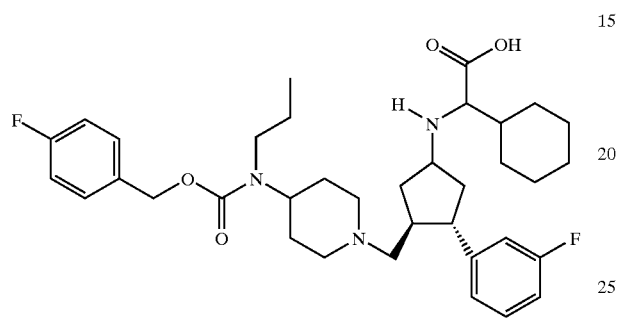
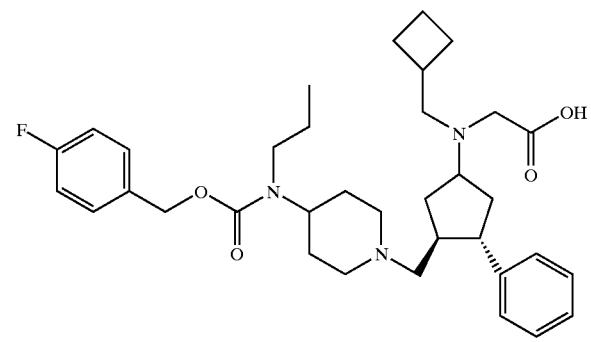
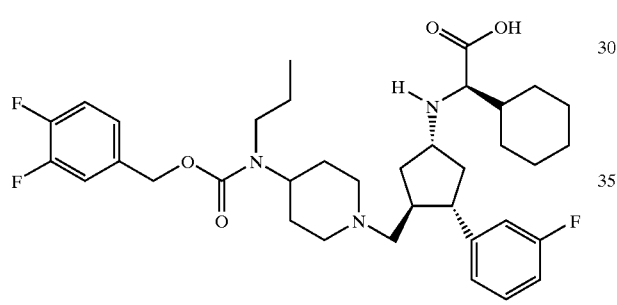
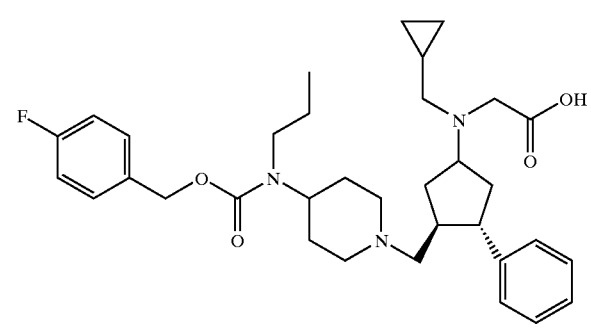
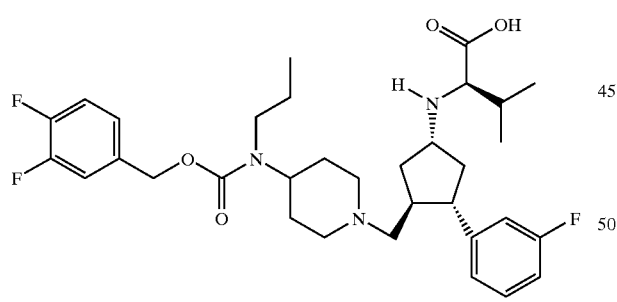
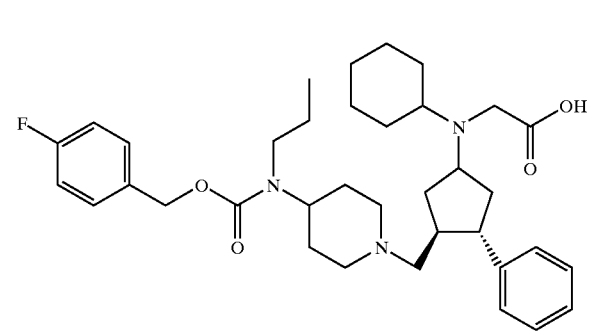
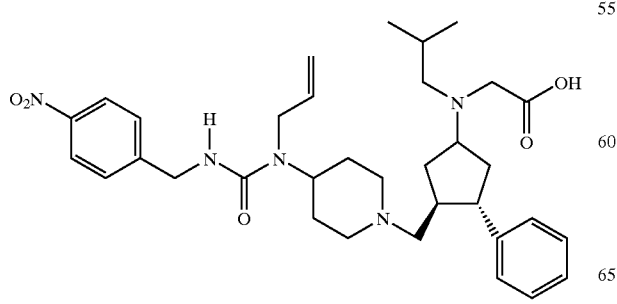
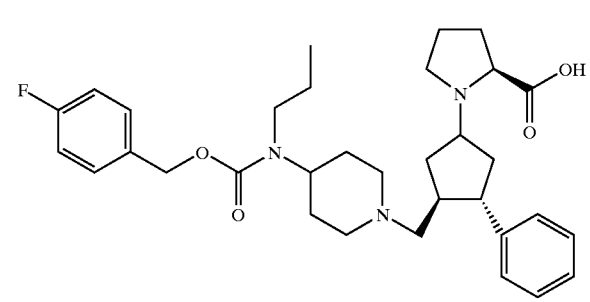

-continued

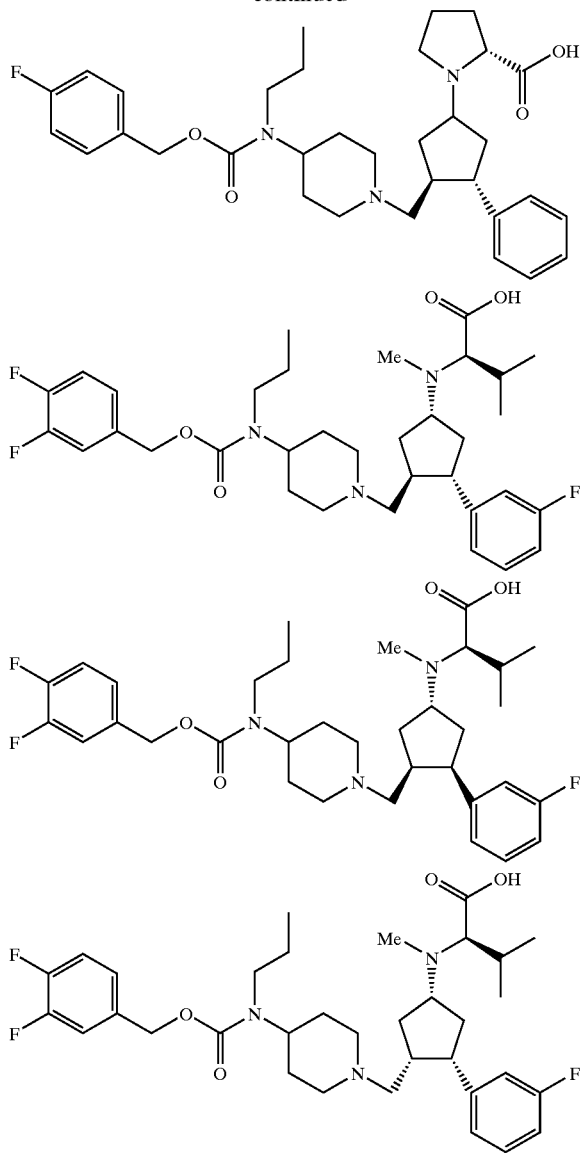

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (WLD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by FHV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants, (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), oc-glucosidase inhibitors (acarbose) and glitazones (troglitazone and pioglitazone); (1) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| ANTIVIRALS Drug Name | Manufacturer | Indication |
| --- | --- | --- |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |

| | | -continued | | | |
|---|---|---|---|---|---|
| AD-439 | Tanox Biosystems | HIV infection, AIDS, ARC | GW 141 | Glaxo Welcome | HIV infection, AIDS, ARC (protease inhibitor) |
| AD-519 | Tanox Biosystems | HIV infection, AIDS, ARC | | | |
| Adefovir dipivoxil | Gilead Sciences | HIV infection | GW 1592 | Glaxo Welcome | HIV infection, AIDS, ARC (reverse transcriptase inhibitor) |
| AL-721 | Ethigen (Los Angeles, CA) | ARC, PGL HIV positive, AIDS | | | |
| Alpha Interferon | Glaxo Wellcome | Kaposi's sarcoma, HIV in combination w/Retrovir | HBY097 | Hoechst Marion Roussel | HIV infection, AIDS, ARC (non-nucleoside reverse transcriptase inhibitor) |
| Ansamycin LM 427 | Adria Laboratories (Dublin, OH) Erbamont (Stamford, CT) | ARC | Hypericin | VIMRx Pharm. | HIV infection, AIDS, ARC |
| Antibody which neutralizes pH labile alpha aberrant Interferon | Advanced Biotherapy Concepts (Rockville, MD) | AIDS, ARC | Recombinant Human Interferon Beta Interferon alfa-n3 | Triton Biosciences (Almeda, CA) Interferon Sciences | AIDS, Kaposi's sarcoma, ARC ARC, AIDS |
| AR177 | Aronex Pharm | HIV infection, AIDS, ARC | Indinavir | Merck | HIV infection, AIDS, ARC, asymptomatic HIV positive, also in combination with AZT/ddI/ddC |
| beta-fluoro-ddA (−) 6-Chloro4(S)-cyclopropylethynyl-4(S)-trifluoro-methyl-1,4-dihydro-2H-3,1-benzoxazin-2-one | Nat'l Cancer Institute Merck | AIDS-associated diseases HIV infection, AIDS, ARC (non-nucleoside reverse transcriptase inhibitor) | Compound A | Merck | HIV infection, AIDS, ARC, asymptomatic HIV positive |
| CI-1012 | Warner-Lambert | HIV-1 infection | ISIS 2922 | ISIS Pharmaceuticals | CMV retinitis |
| Cidofovir | Gilead Science | CMV retinitis, herpes, papillomavirus | KNI-272 | Nat'l Cancer Institute | HIV-assoc. diseases |
| Curdlan sulfate | AJI Pharma USA | HIV infection | Lamivudine, 3TC | Glaxo Wellcome | HIV infection, AIDS, ARC (reverse transcriptase inhibitor); also with AZT |
| Cytomegalovirus immune globin | MedImmune | CMV retinitis | | | |
| Cytovene Ganciclovir | Syntex | sight threatening CMV peripheral CMV retinitis | | | |
| Delaviridine | Pharmacia-Upjohn | HIV infection, AIDS, ARC (protease inhibitor) | Lobucavir | Bristol-Myers Squibb | CMV infection |
| | | | Nelfinavir | Agouron Pharmaceuticals | HIV infection, AIDS, ARC (protease inhibitor) |
| Dextran Sulfate | Ueno Fine Chem Ind Ltd. (Osaka, Japan) | AIDS, ARC, HIV positive asymptomatic | Nevirapine | Boeheringer Ingleheim | HIV infection, AIDS, ARC (protease inhibitor) |
| ddC Dideoxycytidine | Hoffman-La Roche | HIV infection, AIDS, ARC | | | |
| ddI Dideoxyinosine | Bristol-Myers Squibb | HIV infection, AIDS, ARC; combination with AZT/d4T | Novapren | Novaferon Labs, Inc. (Akron, OH) | HIV inhibitor |
| | | | Peptide T Octapeptide Sequence | Peninsula Labs (Belmont, CA) | AIDS |
| DMP-450 | AVID (Camden, NJ) | HIV infection, AIDS, ARC (protease inhibitor) | Trisodium Phosphonoformate | Astra Pharm. Products, Inc | CMV retinitis, HIV infection, other CMV infections |
| EL10 | Elan Corp, PLC (Gainesville, GA) | HIV infection | PNU-140690 | Pharmacia Upjohn | HIV infection, AIDS, ARC (protease inhibitor) |
| Efavirenz (DMP 266) (−) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) | | | |
| | | | Probucol | Vyrex | HIV infection, AIDS |
| | | | RBC-CD4 | Sheffield Med. Tech (Houston TX) | HIV infection, AIDS, ARC |
| Famciclovir | Smith Kline | herpes zoster, herpes simplex | Ritonavir | Abbott | HIV infection, AIDS, ARC (protease inhibitor) |
| FTC | Emory University | HIV infection, AIDS, ARC (reverse transcriptase inhibitor) | Saquinavir | Hoffmann-LaRoche | HIV infection, AIDS, ARC (protease inhibitor) |
| GS 840 | Gilead | HIV infection, AIDS, ARC (reverse transcriptase inhibitor) | Stavudine; d4T Didehydrodeoxy-thymidine | Bristol-Myers Squibb | HIV infection, AIDS, ARC |

-continued

| Drug Name | Manufacturer | Indication |
|---|---|---|
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Intenferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Bioiogical (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immuno-therapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/ gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Phamiacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflomithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |

| | | |
|---|---|---|
| Testosterone Total Enteral Nutrition | Alza, Smith Kline Norwich Eaton Pharmaceuticals | AIDS-related wasting diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N—((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.) The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are either commercially available, are made from known procedures or are prepared as illustrated.

SCHEME 1

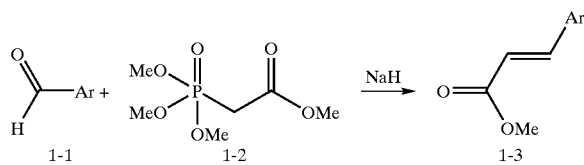

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

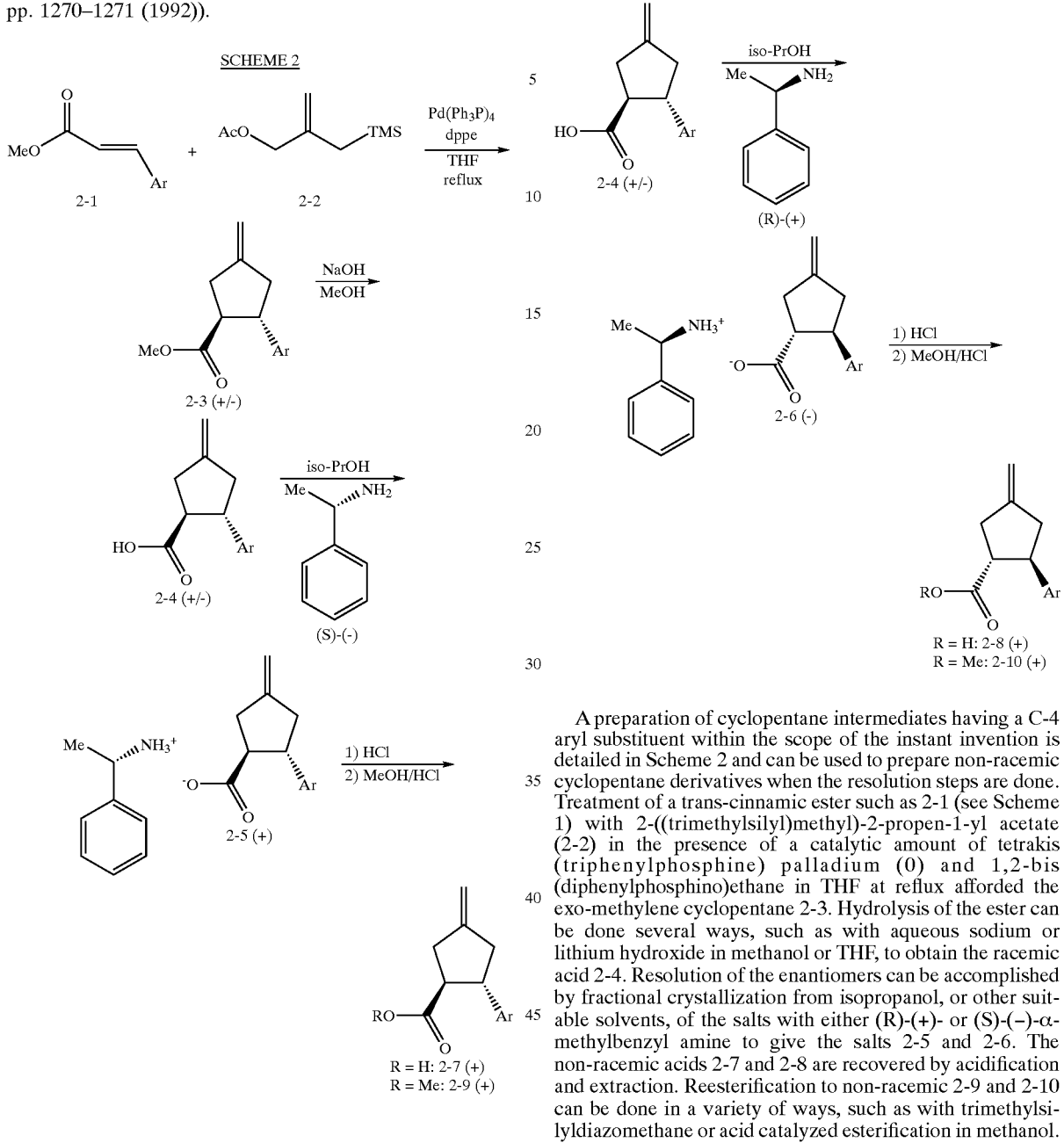

A preparation of cyclopentane intermediates having a C-4 aryl substituent within the scope of the instant invention is detailed in Scheme 2 and can be used to prepare non-racemic cyclopentane derivatives when the resolution steps are done. Treatment of a trans-cinnamic ester such as 2-1 (see Scheme 1) with 2-((trimethylsilyl)methyl)-2-propen-1-yl acetate (2-2) in the presence of a catalytic amount of tetrakis (triphenylphosphine) palladium (0) and 1,2-bis (diphenylphosphino)ethane in THF at reflux afforded the exo-methylene cyclopentane 2-3. Hydrolysis of the ester can be done several ways, such as with aqueous sodium or lithium hydroxide in methanol or THF, to obtain the racemic acid 2-4. Resolution of the enantiomers can be accomplished by fractional crystallization from isopropanol, or other suitable solvents, of the salts with either (R)-(+)- or (S)-(−)-α-methylbenzyl amine to give the salts 2-5 and 2-6. The non-racemic acids 2-7 and 2-8 are recovered by acidification and extraction. Reesterification to non-racemic 2-9 and 2-10 can be done in a variety of ways, such as with trimethylsilyldiazomethane or acid catalyzed esterification in methanol.

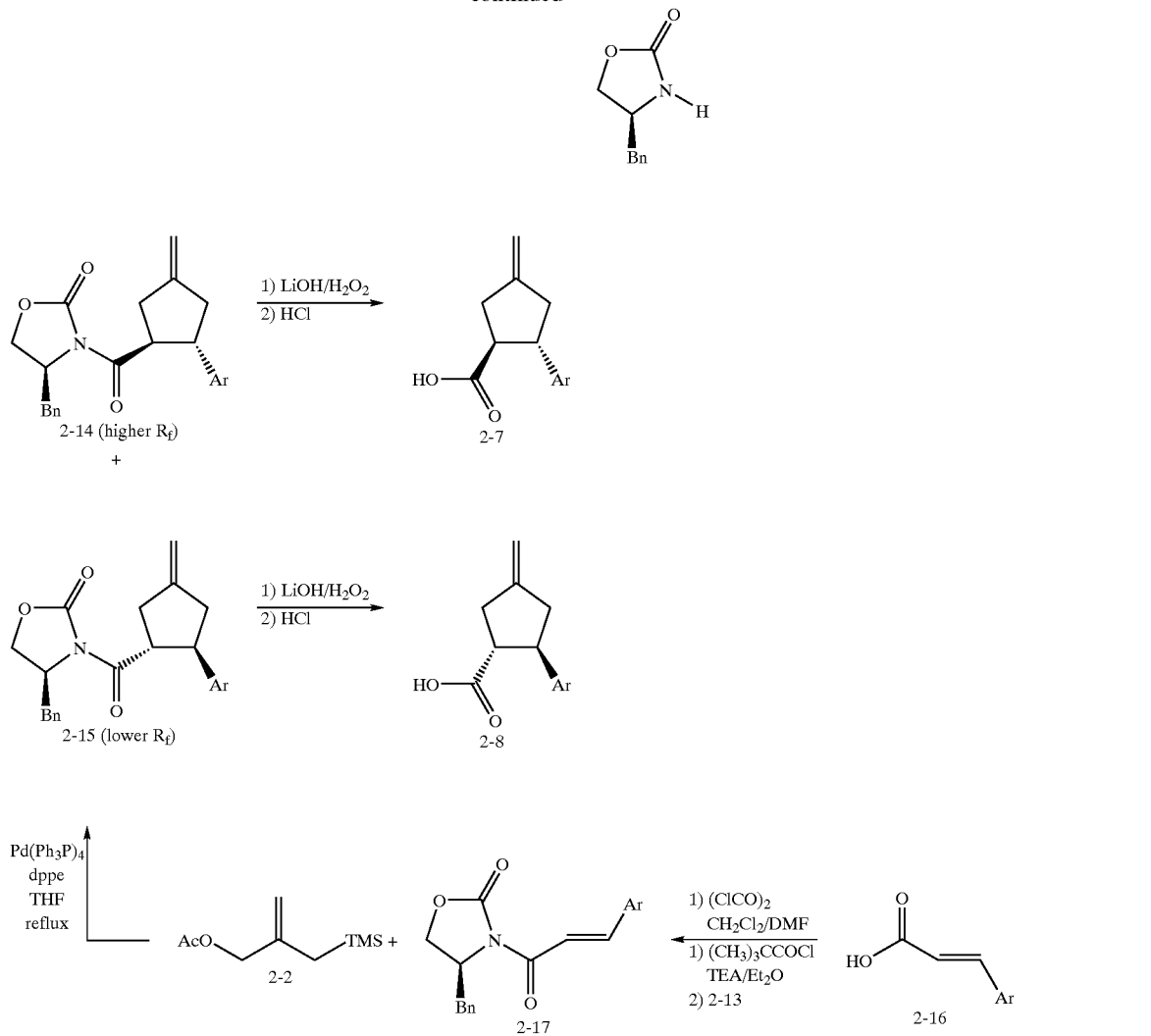

An alternative preparation of non-racemic cyclopentane intermediates having a C-4 aryl substituent within the scope of the instant invention is detailed in Scheme 2A. Conversion of the cyclopentane acid 2-4 to the acid chloride 2-11 under standard conditions, such as with oxalyl chloride in methylene chloride with a catalytic amount of DMF, or to the mixed anhydride 2-12, prepared in situ with trimethylacetyl chloride in ether with TEA as base, followed by reaction with the performed lithium salt of (S)-(−)-4-benzyl-2-oxazolidinone 2-13, afforded the two non-racemic diastereomeric products 2-14 and 2-15, which are then separable by chromatography. Hydrolysis of each diastereomer under standard conditions, such as with lithium hydroxide and hydrogen peroxide or trimethylamine-N-oxide, affords the two non-racemic acids 2-7 and 2-8. Alternatively, in order to obtain an enhanced amount of the desired diastereomer 2-14 before separation, similar conversion of the starting trans-cinnamic acid 2-16 (Scheme 1) to the chiral trans-cinnamate 2-17 followed by the ring formation reaction with 2-((trimethylsilyl)methyl)-2-propen-1-yl acetate (2-2) as detailed in Scheme 2 affords a 60:40 product mixture of 2-14: 2-15.

SCHEME 3

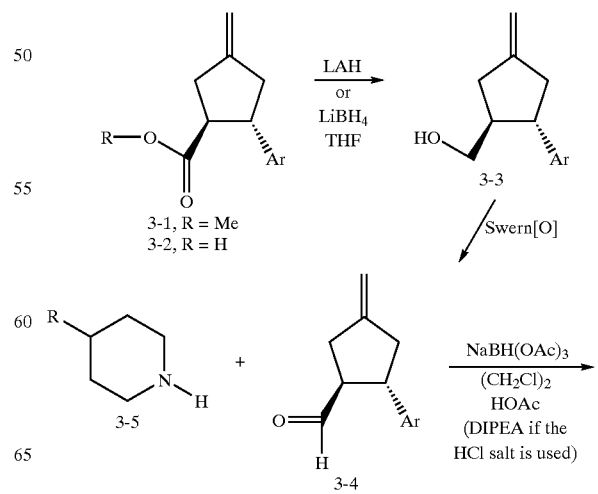

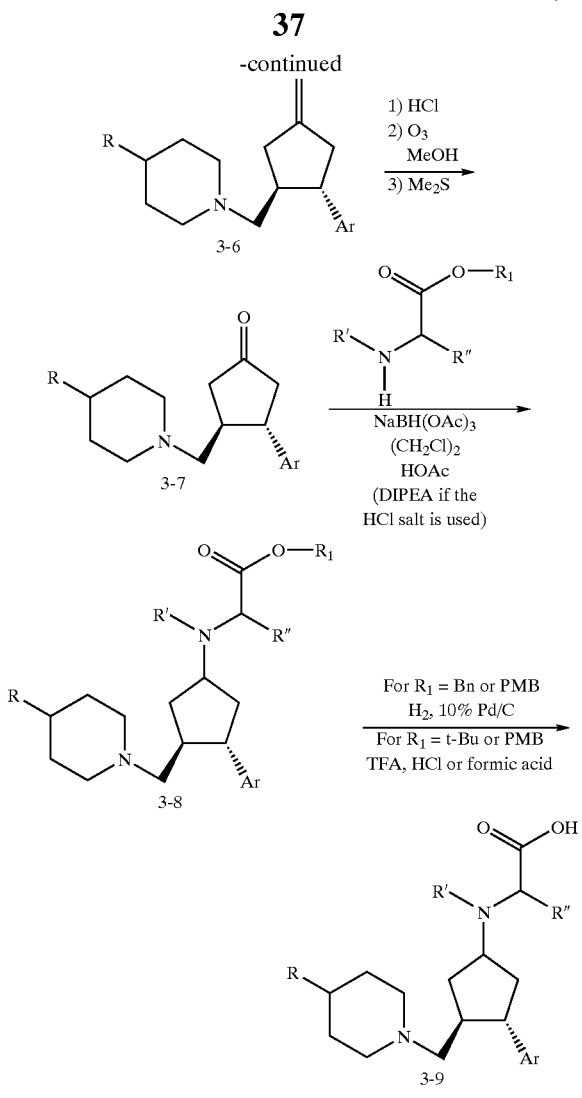

methyl)cyclopentane derivative 3-6. In the cases where the R group of the piperidine is stable to ozone, ozonolysis of the exo-methylene followed by a reductive work-up with dimethyl sulfide affords the ketone 3-7. Alternatively, 3-7 can be obtained from 3-6 through a stepwise oxidation using catalytic osmium tetroxide in the presence of N-methylmorpholine-N-oxide followed by sodium periodate cleavage of the intermediate diol. A second reductive alkylation of a D- and/or L-amino-acid ester, such as the methyl, ethyl, t-butyl, benzyl or 4-methoxybenzyl ester of glycine (R"=H), alanine (R"=Me), valine (R"=iso-Pr), leucine (R"=iso-Bu), isoleucine (R'=sec-Bu), cyclopropylalanine (R"=CH$_2$cycPr), cyclobutylalanine (R"=CH$_2$cycBu), cyclohexylglycine (R"=cycHex) or a N-alkyl amino-acid, such as N-methyl glycine (R'=Me), or a cyclic amino-acid, such as proline (R'R"=—(CH$_2$)$_3$-), with 3-7 as described above with sodium triacetoxyborohydride or sodium cyanoborohydride affords 3-8. Final deprotection of the ester under conditions to which the R group is stable, such as HCl in ether, TFA or formic acid for t-butyl and 4-methoxybenzyl esters, hydrogenation for benzyl esters or standard hydrolysis for alkyl or benzyl esters, affords the final product(s) 3-9 which are within the scope of the instant invention and which can be chemokine receptor modulators or which can be further modified as shown below in Scheme 14. The two individual C-1 isomers (four diastereomers when either the cyclopentyl scaffold or the amino-acid are racemic) can be separated by flash chromatography, Prep TLC or HPLC methods as either the penultimate esters 3-8 and/or the final compounds 3-9.

Preparation of some 1,3,4-trisubstituted cyclopentanes within the scope of the instant invention is given in Scheme 3. Reduction of ester 3-1 (either racemic or non-racemic) (Scheme 2), for example, with lithium borohydride, diisobutylaluminum hydride, lithium aluminum hydride, or sodium bis(2-methoxyethoxy)aluminum hydride in a suitable solvent, such as ether or THF, provides the primary alcohol 3-3. Alternatively, reduction of the acid 3-2 (either racemic or non-racemic) (Scheme 2 or 2A), for example with lithium aluminum hydride in THF, will also afford the alcohol 3-3. In cases where the Ar moiety is not amenable to salt resolution as detailed in Scheme 3, an alternative resolution can often be achieved using chiral HPLC methods to separate the enantiomers 3-3. Oxidation of 3-3 to the aldehyde 3-4 can be carried out under numerous conditions, such as with DMSO and oxalyl chloride at low temperature, followed by triethylamine (Swern oxidation), with the Dess-Martin periodinane, with N-methylmorpholine in the presence of a catalytic amount of TPAP, or with various chromium trioxide-based reagents (see March J. "Advanced Organic Chemistry", 4th ed., John Wiley & Sons, New York, pp. 1167–1171 (1992)). Reductive alkylation of a cyclic amine, such as piperidine 3-5 (see Schemes 12 and 13), using for example sodium triacetoxyborohydride or sodium cyanoborohydride in a suitable solvent such as methylene chloride, 1,2-dichloroethane, THF, acetonitrile or methanol, with 3-4 then provides a 3-(4-(substituted-piperidin-1-yl)

SCHEME 4

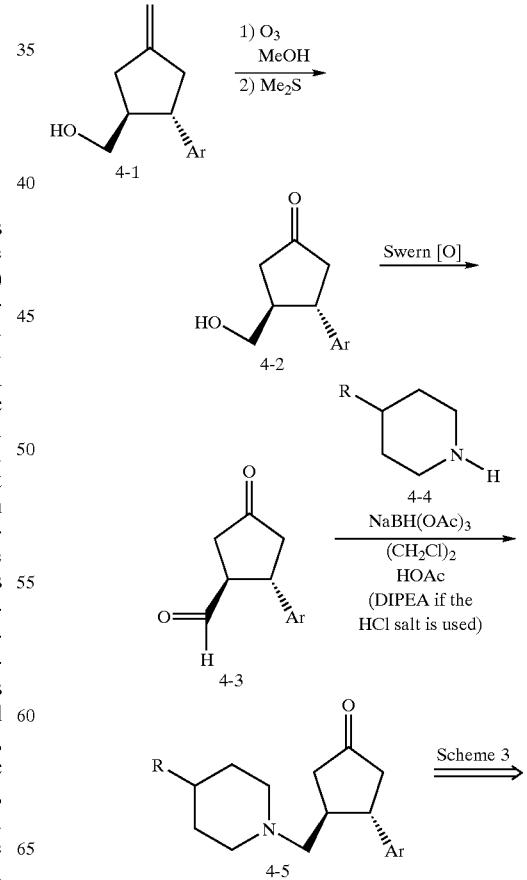

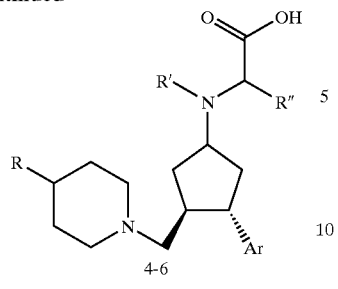

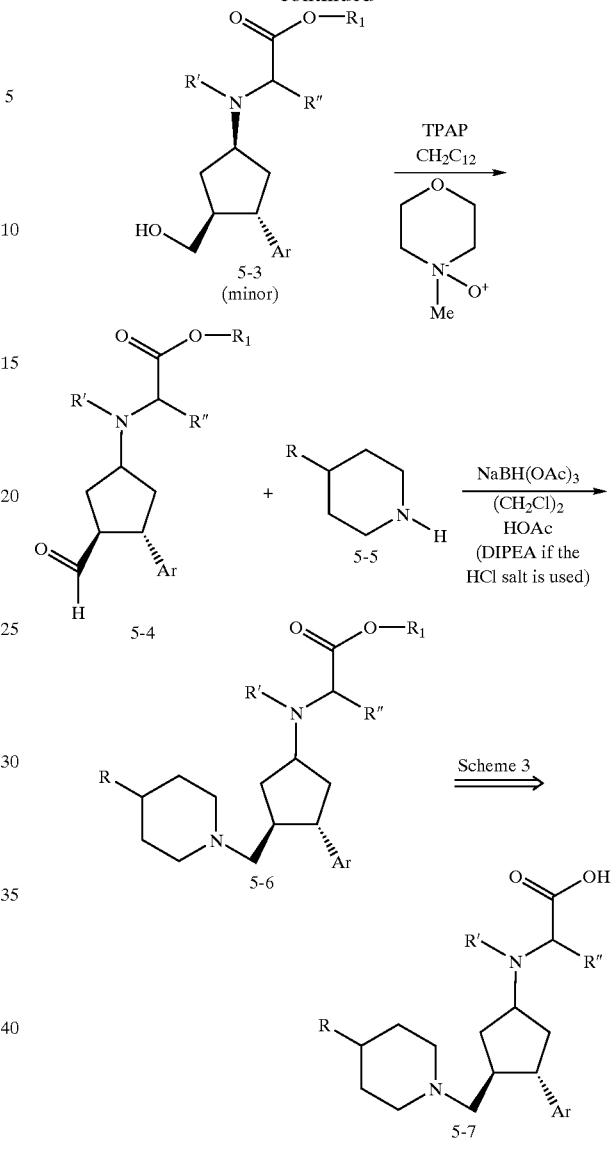

An alternative route for the preparation of some 1,3,4-trisubstituted cyclopentanes within the scope of the instant invention is given in Scheme 4. In the cases where the R group of the piperidine in Scheme 3 is not stable to ozone or the osmium tetroxide/sodium periodate oxidation sequence, oxidation of the exo-methylene can be done prior to the reductive alkylation of the piperidine. Thus, ozonolysis of the alcohol 4-1 (Scheme 3) followed by a reductive work-up with dimethyl sulfide affords the ketone-alcohol 4-2. Oxidation to the ketone-aldehyde 4-3 can be done as described for Scheme 3 with N-methylmorpholine/TPAP or under Swern conditions. Selective reductive alkylation of the 4-substitutedpiperidine 4-4 (see Schemes 12 and 13) with the aldehyde of 4-3, using for example sodium triacetoxyborohydride or sodium cyanoborohydride in a suitable solvent such as methylene chloride, 1,2-dichloroethane, THF, acetonitrile or methanol, then provides the 3-(4-(substituted-piperidin-1-yl)methyl)cyclopentane derivative 4-5 (same as 3-7). This can then be converted to the final product(s) 4-6 as described in Scheme 3.

SCHEME 5

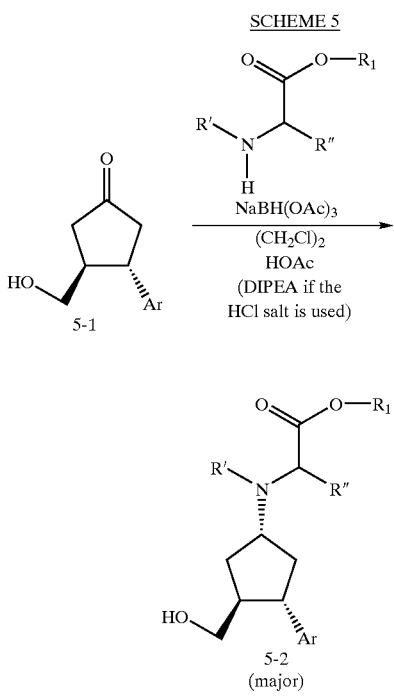

An alternative route for the preparation of some 1,3,4-trisubstituted cyclopentanes within the scope of the instant invention is given in Scheme 5. Reductive alkylation with ketone alcohol 5-1 (Scheme 4) of a variety of amino-acid esters (See Scheme 3) affords the alcohols 5-2 and 5-3, of which 5-2 is the major product (lower $R_f$ when R" is (S), higher $R_f$ when R" is (R)) and 5-3 is the minor product (higher $R_f$ when R" is (S), lower $R_f$ when R" is (R)). Separation of the individual diastereomers (2 when both reactants are non-racemic, 4 when only one is non-racemic) can be done at this intermediate or at a later step. Oxidation of 5-2 and/or 5-3 to the aldehyde(s) 5-4 can be done as described in Scheme 3, preferably now with N-methylmorpholine/TPAP due to the presence of the secondary N—H. Reductive alkylation of a 4-substitutedpiperidine 5-5 (see Schemes 12 to 30) with the aldehyde of 5-4, using for example sodium triacetoxyborohydride or sodium cyanoborohydride in a suitable solvent such as methylene chloride, 1,2-dichloroethane, THF, acetonitrile or methanol, then provides the 3-(4-(substituted-piperidin-1-yl)methyl)cyclopentane derivative 5-6. The intermediate ester(s) 5-6 can then be converted to the final product(s) 5-7 as described in Scheme 3.

SCHEME 5A

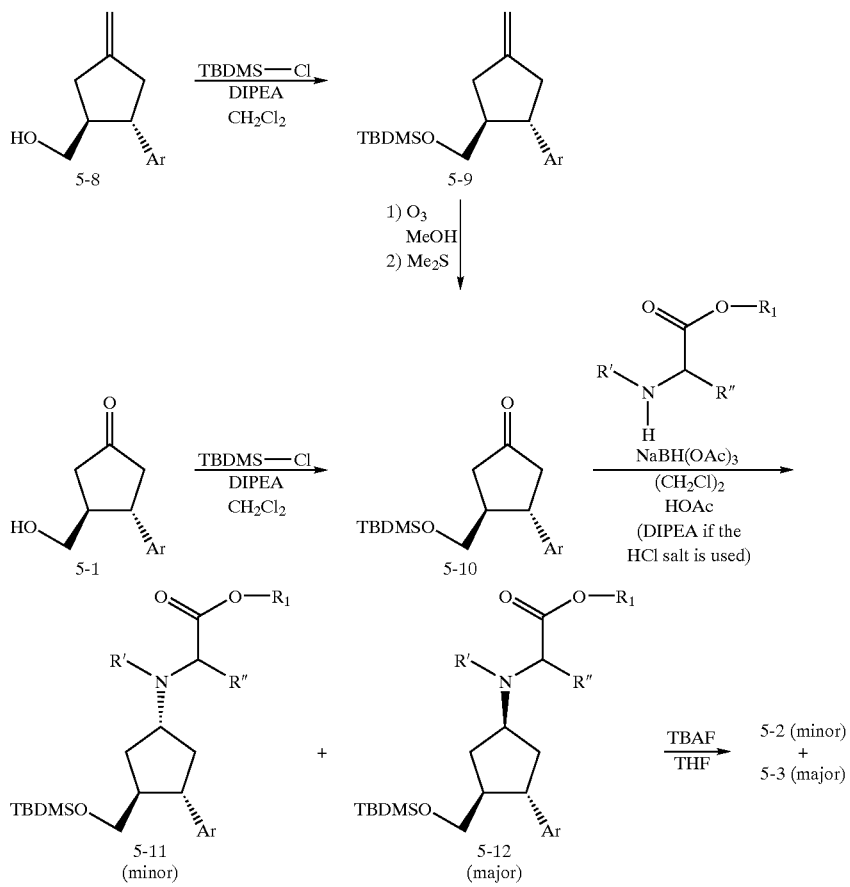

An alternative preparation of the intermediates 5-2 and 5-3 in Scheme 5 which reverses the C-1 isomeric selectivity is shown in Scheme 5A. Silylation of the alcohol moiety of 5-1 (Scheme 4) gives the silyl ether 5-10. Alternatively, silylation of the alcohol 5-8 (Scheme 3) gives 5-9 which on ozonolysis can also afford the silyl ether 5-10. Reductive alkylation of the aforementioned amino-acid esters now using the silyl ether 5-10 affords the products 5-11 and 5-12 in an essentially opposite ratio as is obtained in Scheme 5 for 5-2 and 5-3. TBAF desilylation then affords primarily 5-3. Thus, the preferred C-1 orientation can be selected for depending on the requirements of the desired final compounds.

SCHEME 6

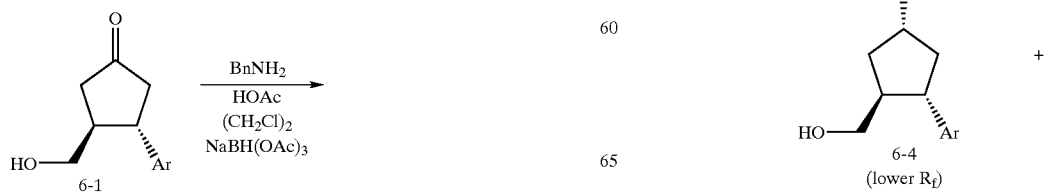

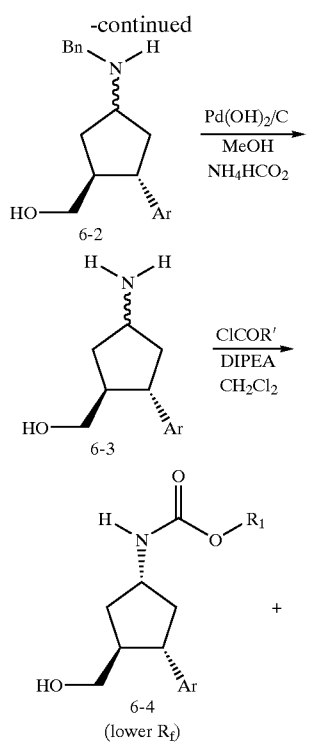

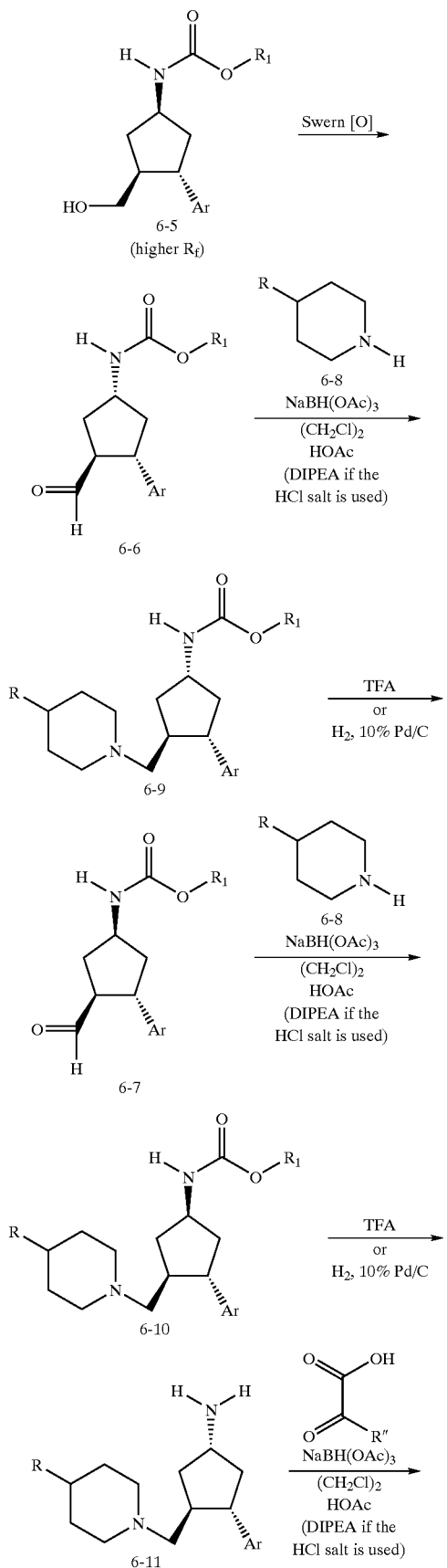
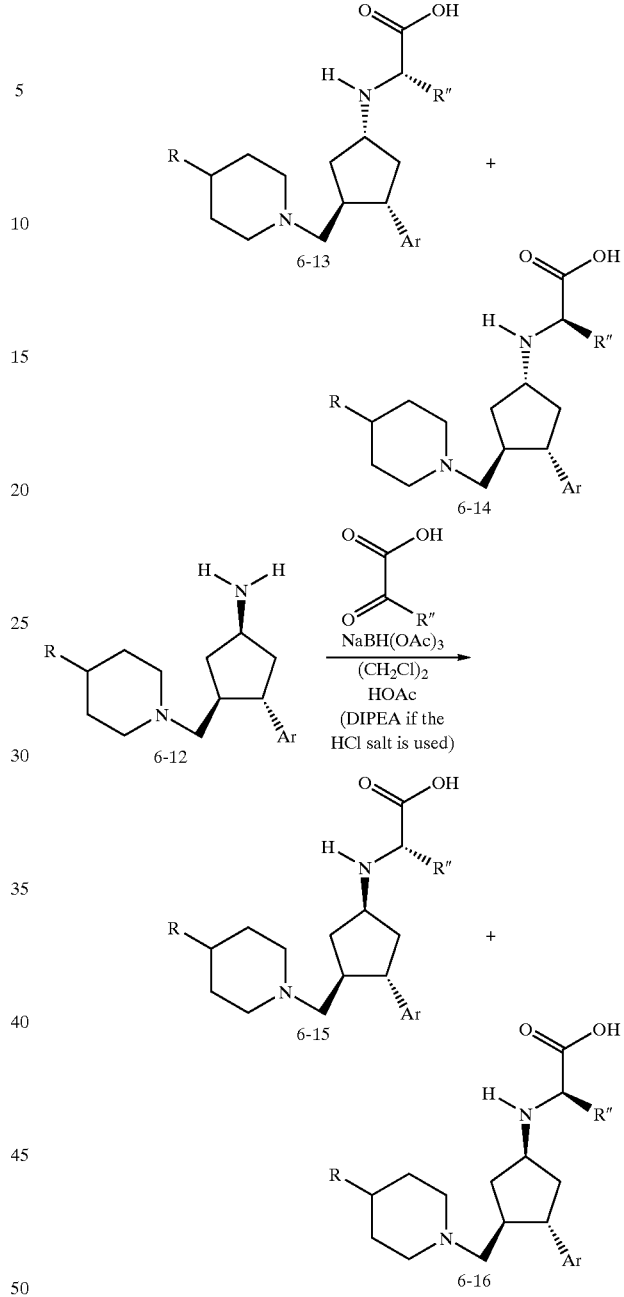

An alternative route for the preparation of some 1,3,4-trisubstituted cyclopentanes within the scope of the instant invention is given in Scheme 6. Reductive alkylation of benzylamine with ketone-alcohol 6-1 (Scheme 4, either racemic or non-racemic), using for example sodium triacetoxyborohydride or sodium cyanoborohydride, gives 6-2 which can be hydrogenated under standard conditions in methanol in the presence of a palladium catalyst, for example Pd/C or Pearlman's catalyst and using either hydrogen under pressure or ammonium formate at reflux, to afford the primary amine 6-3. Reaction of the amine with CBZ chloride or BOC anhydride gives the amine protected carbamates 6-4 and 6-5 as a mixture of C-1 isomers which can be separated. Oxidation to the aldehydes 6-6 and 6-7 is carried out under Swern conditions or with N-methylmorpholine/TPAP. The relative stereochemistry of the C-1 to the C-3 and C4 substituents was determined by NMR Noe experiments on either the alcohols 6-4 and 6-5 or the aldehydes 6-6 and 6-7. Reductive alkylation of a 4-substitutedpiperidine 6-8 with the individual aldehydes 6-6 and 6-7 using for example sodium triacetoxyborohydride or sodium cyanoborohydride in a suitable solvent such as methylene chloride, 1,2-dichloroethane, THF, acetonitrile or methanol, then provides each of the C-1 amino-protected isomeric 3-(4-(substituted-piperidin-1-yl)methyl) cyclopentane derivatives 6-9 and 6-10. Deprotection of the C-1 amino with either TFA (for $R_1$=t-butyl) or standard hydrogenation (for $R_1$=Bn) depending on the stability of the piperidine R group affords the amines 6-11 and 6-12. These amines can then be individually reductively alkylated as above with 2-oxo-acetic acids, such as 2-oxovaleric (R"=n-Pr), 4-methyl-2-oxovaleric (R"=iso-Bu), 2-oxophenylacetic (R"=Ph), to afford the final compounds 6-13 and 6-14 and 6-15 and 6-16 as mixtures of the R" isomers. In the case of R"=iso-Bu and non-racemic cyclopentyl scaffold, comparison of the HPLC of these products with those obtained in Scheme 5A allowed the stereochemical assignments of all the final products and intermediates.

An alternative route for the preparation of some 1,3,4-trisubstituted cyclopentanes within the scope of the instant invention is given in Scheme 7. Reductive alkylation, using for example sodium triacetoxyborohydride or sodium cyanoborohydride, of an alkyl amine with the ketone 7-1 (Schemes 3 or 4) gives 7-2 as a mixture of C-1 isomers which may be separated. Alternatively, carbamate 7-3 (see Scheme 6) can be alkylated with an alkyl or allyl halide, such as 1-bromo-2-methylprop-2-ene, and a strong base, such as sodium hydride in DMF, followed by hydrogenation under standard conditions to reduce the allyl. When $R_1$ is Bn, removal the CBZ can occur simultaneously to give the same amine intermediate 7-2. When R1 is t-butyl, a subsequent reaction with TFA is required to give 7-2. Alkylation of the amine with t-butyl or benzyl bromoacetate affords 74 which can be converted to the desired final compounds 7-5 as described in Scheme 3.

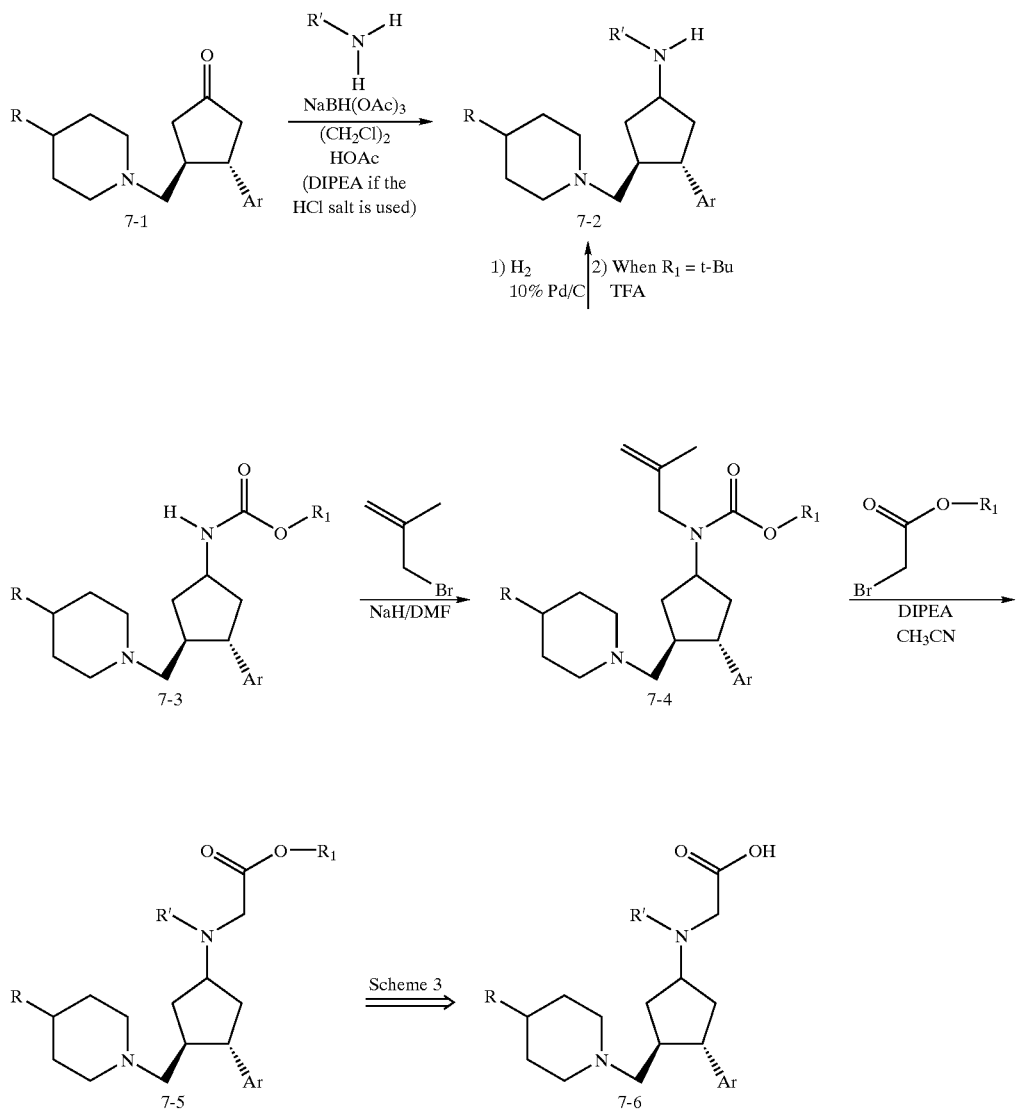

SCHEME 7

SCHEME 8

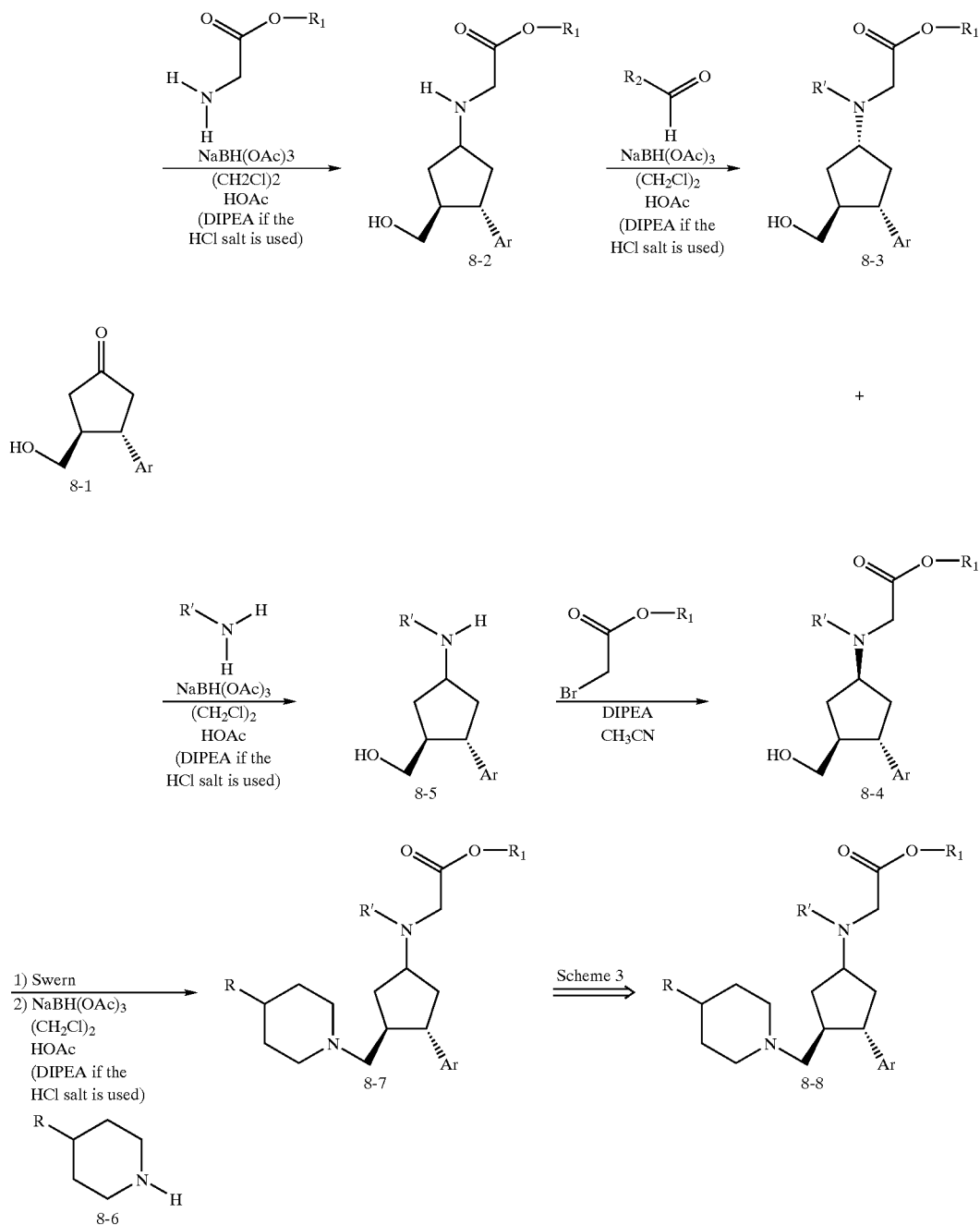

An alternative route for the preparation of some 1,3,4-trisubstituted cyclopentanes within the scope of the instant invention is given in Scheme 8. Reductive alkylation, using for example sodium triacetoxyborohydride or sodium cyanoborohydride, of glycine t-butyl, benzyl or PMB ester with the ketone-alcohol 8-1 (Scheme 4) gives 8-2 as a mixture of C-1 isomers. A second reductive alkylation with a ketone or aldehyde affords the N-alkyl glycine derivatives 8-3 and 8-4 which can be separated chromatographically either before and/or after the second alkylation. Also, the order of the steps can be reversed such that reductive alkylation of an amine with 8-1 first to give 8-5, followed by alkylation with an alkyl or benzyl bromoacetate as in Scheme 7, affords 8-3 and 8-4. These reactions generally give 8-3 as the predominate product. Individual oxidation of the alcohols 8-3 and 8-4 can be done either under Swern conditions or using the N-methylmorpholine/TPAP method to give the aldehydes followed by a second or third reductive alkylation of a 4-substitutedpiperidine 8-6, using for example sodium triacetoxyborohydride or sodium cyanoborohydride in a suitable solvent such as methylene chloride, 1,2-dichloroethane, THF, acetonitrile or methanol, which then provides the 3-(4-(substituted-piperidin-1-yl) methyl)cyclopentane derivative 8-7. This intermediate can then be converted to the final products 8-8 as described in Scheme 3.

SCHEME 8A

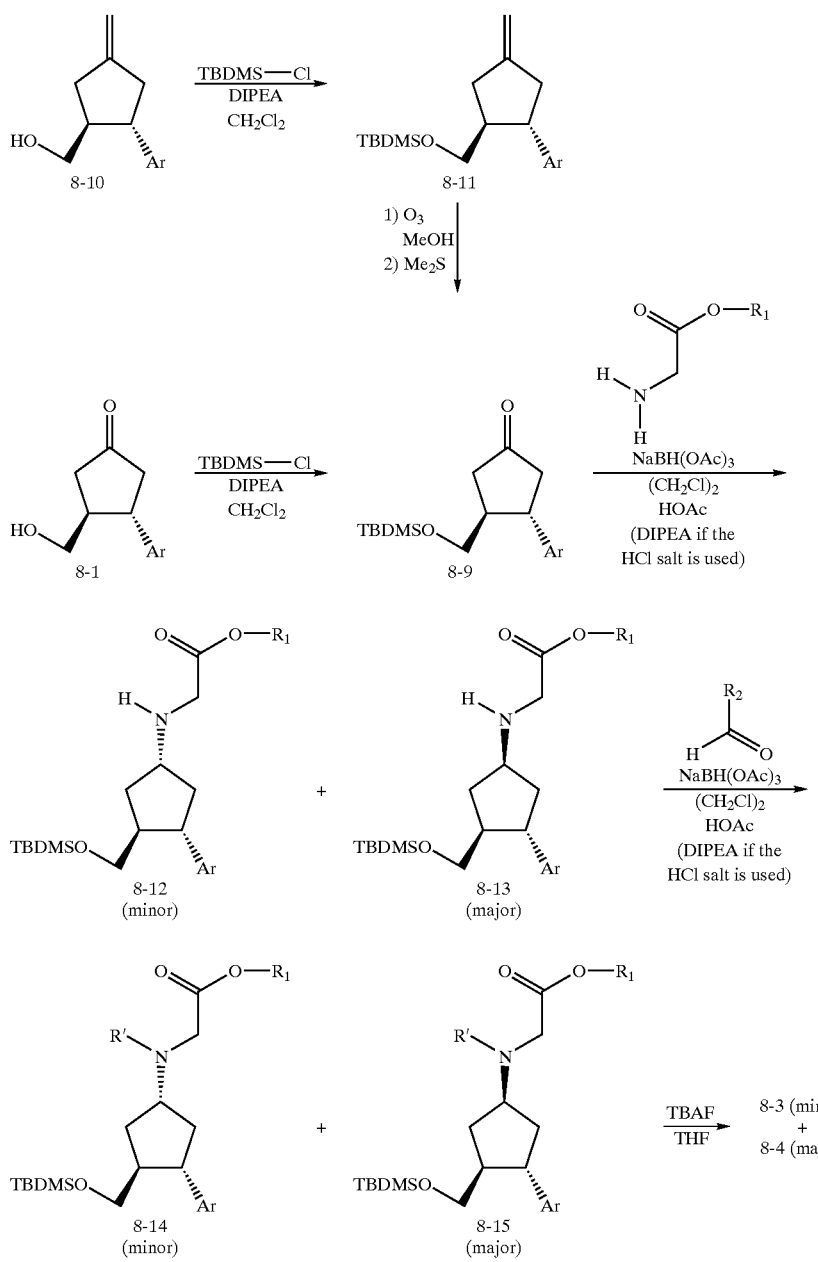

An alternative preparation of the intermediates 8-3 and 8-4 in Scheme 8 which again reverses the C-1 isomeric selectivity is shown in Scheme 8A. Silylation of the alcohol moiety of 8-1 (Scheme 4) gives the silyl ether 8-9. Alternatively, silylation of the alcohol 8-10 (Scheme 3) gives 8-11, which on ozonolysis can also afford the silyl ether 8-9. Reductive alkylation now using the silyl ether 8-9 gives 8-12 and 8-13 followed by the second reductive alkylation with an aldehyde or ketone affords the products 8-14 and 8-15 in an essentially opposite ratio as is obtained in Scheme 8 for 8-3 and 8-4. TBAF desilylation then affords primarily 8-4. Separation of the C-1 isomers can usually be achieved at one or more of the intermediate steps. Thus, the preferred C-1 orientation can be selected for depending on the requirements of the desired final compounds.

SCHEME 9

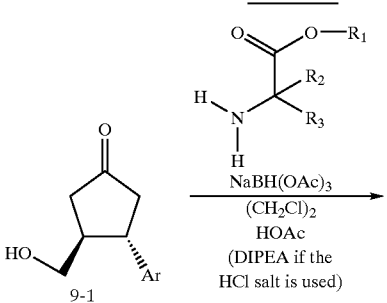

-continued

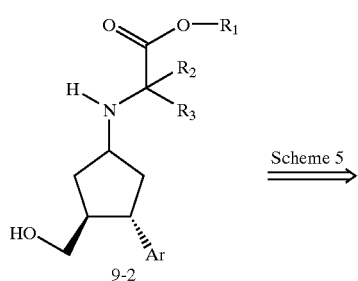
9-2

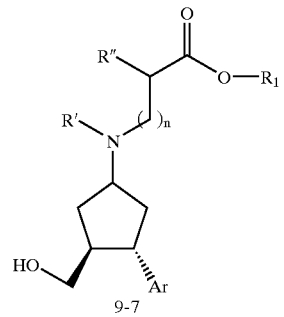
9-7

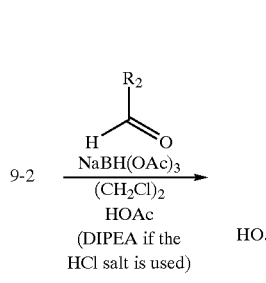
9-2 → (NaBH(OAc)₃, (CH₂Cl)₂, HOAc, DIPEA if the HCl salt is used) → 9-4

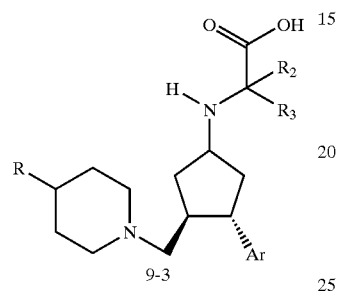
9-3

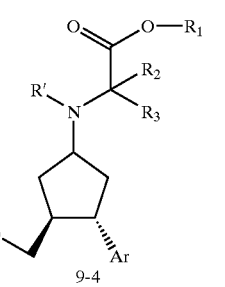
9-4 ⟹ Scheme 5

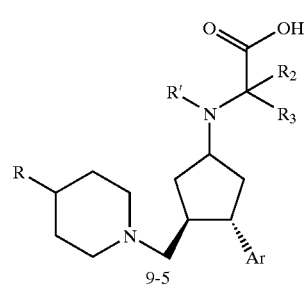
9-5

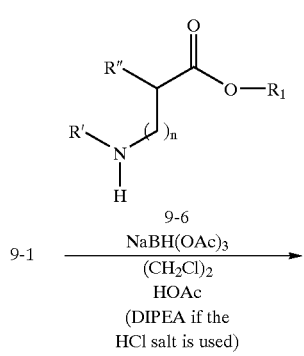
9-1 + 9-6 → (NaBH(OAc)₃, (CH₂Cl)₂, HOAc, DIPEA if the HCl salt is used)

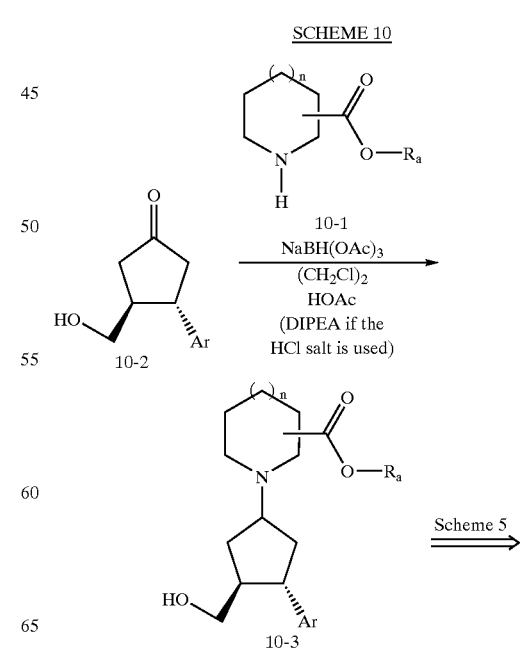

Several other alternative routes for the preparation of some 1,3,4-trisubstituted cyclopentanes within the scope of the instant invention are given in Scheme 9. Reductive alkylation, using for example sodium triacetoxyborohydride or sodium cyanoborohydride, of an amino-acid ester having dialkyl substitution with the ketone-alcohol 9-1 (Scheme 4) gives 9-2 as a mixture of C-1 isomers which may be separated and carried on to the final product(s) 9-3 individually or as a mixture as detailed in Scheme 5. Alternatively, a second reductive alkylation of 9-2 as in Scheme 8 affords 9-4 which may be separable or used as a mixture to give final product(s) 9-5. Also, more extended amino-acid esters, such as a β-alanine ester (9-6, n=1) or 4-aminobutyrate (9-6, n=2), which may also be substituted on the chain or on N, can be employed to give 9-7. These intermediates can then be converted to final product(s) 9-8 as described in Scheme 5 and/or 8.

SCHEME 10

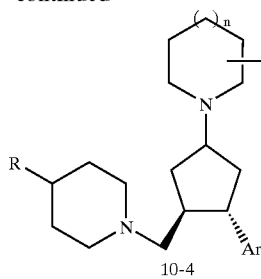

10-4

An alternative route for the preparation of some 1,3,4-trisubstituted cyclopentanes within the scope of the instant invention is given in Scheme 10. Reductive alkylation, using for example sodium triacetoxyborohydride or sodium cyanoborohydride, of a cyclic secondary amino-acid 10-1, such as D- or L-proline t-butyl ester (n=0), β-proline t-butyl ester (n=0), 2-, 3-, and 4-t-butylcarboxypiperidine (n=1), with the ketone-alcohol 10-2 (Scheme 4) gives 10-3 and 10-4 as a mixture of C-1 isomers which may be separated. These intermediates can then be converted to the final product(s) as described in Scheme 5.

SCHEME 11

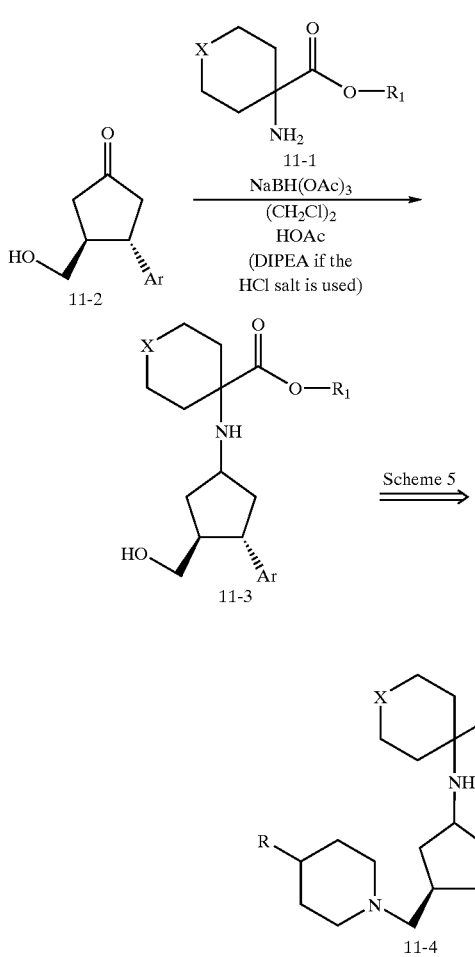

An alternative route for the preparation of some 1,3,4-trisubstituted cyclopentanes within the scope of the instant invention is given in Scheme 11. Reductive alkylation, using for example sodium triacetoxyborohydride or sodium cyanoborohydride, of a cycloalkyl amino-acid 11-1, such as 1-aminocyclopentane carboxylic acid t-butyl ester (X=single bond) or a heterocyclic amino-acid, such as 4-aminomorpholin-2-yl carboxylic acid t-butyl ester (X=O) with the ketone-alcohol 11-2 (Scheme 4) gives a mixture of C-1 isomers which may be separated to give, for example, 11-3. These intermediates can then be converted to the final product(s) such as 11-4 as described in Scheme 5.

SCHEME 12

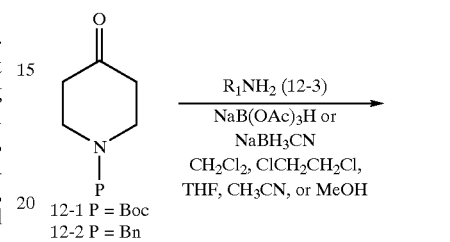

12-1 P = Boc
12-2 P = Bn

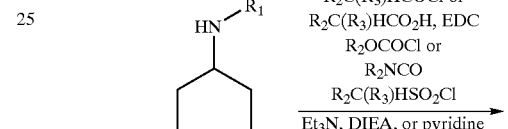

12-4 P = Boc
12-5 P = Bn

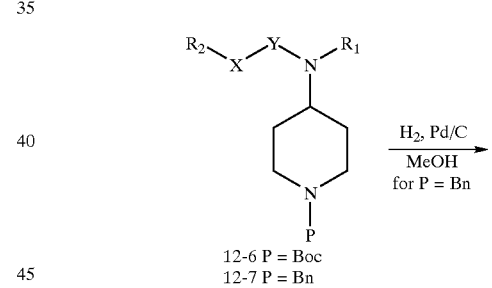

12-6 P = Boc
12-7 P = Bn

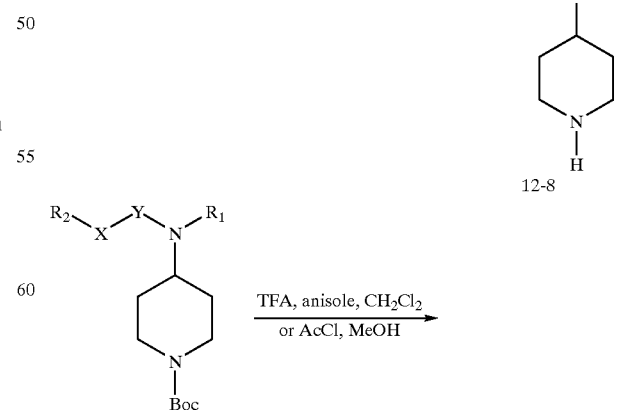

12-6

12-8

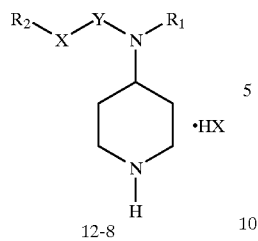

12-8

X = C(R₃)H, O, NH
Y = CO, SO₂

Synthetic routes for the preparation of piperidines bearing a 4-substituent containing an amide, carbamate, urea or sulfonamide functional group are given in Scheme 12. Reductive alkylation of commercially available 12-1 or 12-2 with primary amine 12-3 in the presence of sodium triacetoxyborohydride or sodium cyanoborohydride in a suitable solvent (for example, methylene chloride, 1,2-dichloroethane, THF, acetonitrile, or methanol) provides amines 12-4 or 12-5. Acylation is then carried out with an acyl chloride (or a carboxylic acid plus an activating agent, such as EDC, DCC, or BOP-Cl) to provide 12-6 or 12-7 as an amide. Alternatively, acylation with a chloroformate provides 12-6 or 12-7 as a carbamate. Treatment of 12-4 or 12-5 with an isocyanate affords 12-6 or 12-7 as a urea. Treatment of 12-4 or 12-5 with a sulfonyl chloride affords 12-6 or 12-7 as a sulfonamide. For each of these reactions, an amine base is employed, such as triethylamine, DIEA, pyridine, or 2,6-lutidine. In the case of the benzyl-protected derivative 12-7, hydrogenolysis under standard conditions (for example, hydrogen in the presence of palladium on carbon in methanol or ethanol) provided desired intermediate 12-8. For the N-Boc compound 12-6, exposure to suitable anhydrous acidic conditions (for example, trifluoroacetic acid and anisole in methylene chloride at temperatures from 0–25 degrees C. or HCl in methanol at 0–25 degrees C.) affords the salt of 12-8. This compound is then utilized as the cyclic secondary amine component as shown above in Schemes 3, 4, 5, 6, 8, 9, 10 and 11. Alternatively, if no functionality are present in the alkyl cyclopentane framework that would be adversely effected by the above mentioned chemistry, then 4-piperidone may be attached directly to the alkyl cyclopentane framework described above, and the chemistry described in this paragraph can be carried out equating the alkyl cyclopentane segment to the group 'P' given in Scheme 12, structures 1 through 7.

SCHEME 13

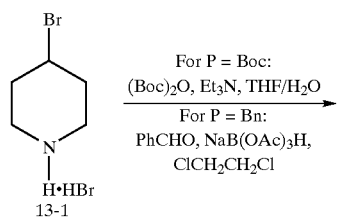

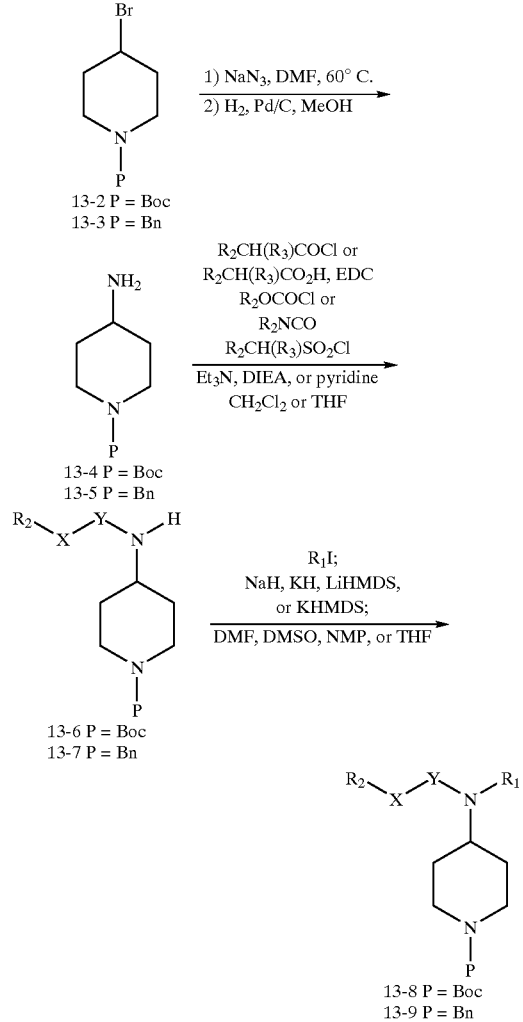

X = C(R₃)H, O, NH
Y = CO, SO₂

Alternate synthetic routes for the preparation of piperidines bearing a 4-substituent containing an amide, carbamate, urea or sulfonamide functional group are given in Scheme 13. Protection of 4-bromopiperidine can be carried out with several protecting groups for nitrogen. For example, using standard conditions, protection with a Boc group gives 13-2, whereas reductive alkylation with benzaldehyde yields the N-benzyl derivative 13-3. Displacement of the bromide with sodium azide in warm to hot DMF provides the 4-azidopiperidine derivative, and reduction of the azide with hydrogen in the presence of a palladium catalyst (for the Boc protected intermediate) or with triphenylphosphine followed by hydrolysis (for N-benzyl protected intermediate) provides the aminopiperidine 13-4 or 13-5. Acylation is then carried out with an acyl chloride (or a carboxylic acid plus an activating agent, such as EDC, DCC, or BOP-Cl) to provide 13-6 or 13-7 as an amide. Alternatively, acylation with a chloroformate provides 13-6 or 13-7 as a carbamate. Treatment of 13-4 or 13-5 with an isocyanate affords 13-6 or 13-7 as a urea. Treatment of 13-4 or 13-5 with a sulfonyl chloride affords 13-6 or 13-7 as a sulfonamide. For each of these reactions, an amine base is employed, such as triethylamine, DIEA, pyridine, or 2,6-lutidine. When X=C(R₃)HCO, OCO, or SO₂ compounds 13-6 and 13-7 may optionally be alkylated by treatment with a base such as sodium hydride, potassium hydride, LiHMDS, KHMDS, or NaHMDS followed by treatment with an alkyl iodide, allyl halide, or propargyl halide. Solvents such as DMF, DMSO, N-methylpyrrolidine or THF are suitable. These procedures provide carbamate, urea, amide or sulfonamidel 3-8 and 13-9. Removal of the protecting groups is then carried out as shown in Scheme 12 above, and the resulting 1-unsubstituted piperidines are then utilized as noted in the descriptions for Schemes 3, 4, 5, 6, 8, 9, 10 and 11.

In some cases the order of carrying out the foregoing reaction schemes may be varied to facilitate the reaction or to avoid unwanted reaction products. The following examples are provided for the purpose of further illustration only and are not intended to be limitations on the disclosed invention.

General

Concentration of solutions was carried out on a rotary evaporator under reduced pressure. Flash chromatography was carried out on silica gel (230–400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC Conditions

HPLC A. Retention time using the following conditions: Column: YMC ODS A, 5μ, 4.6×50 mm; Gradient Eluant: 10:90 to 90:10 v/v $CH_3CN/H_2O$+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5μ4.6×100 mm column; Gradient Eluant: 10:90 to 90:10 v/v $CH_3CN/H_2O$+0.5% TFA over 10 min, hold 2 min; Detection: PDA, 200–400 nm; Flow Rate: 2.25 mL/min.

The following are representative Procedures for the preparation of the piperidines used in the following Examples or which can be substituted for the piperidines used in the following Examples which may not be commercially available.

Procedure 1

4-(N-(t-Butoxycarbonyl)-N-(ethyl)amino)piperidine
Step A: (1-Benzyloxycarbonylpiperidin-4-yl)isocyanate To a solution of 9.72 g (34.8 mmol) of 1-benzyloxycarbonyl-4-carboxypiperidine in 100 mL of methylene chloride was added 2 drops of DME and then slowly 3.34 mL (38.3 mmol) of oxalyl chloride. The reaction was stirred at rt for 1 h (gas evolution had stopped) and the volatiles were removed in vacuo followed by evaporation of a portion of toluene.

The above residue was taken up in 100 mL of acetone and slowly added to a solution of 5.66 g (87 mmol) of sodium azide in 25 mL of water and 25 mL of acetone while stirred in an ice bath. The reaction was stirred at 0° C. for 1.5 h and then diluted with ice water and extracted twice with 2×150 mL of toluene. The organic layers were each washed with a portion of brine, dried over sodium sulfate, combined and concentrated to about 100 mL in vacuo with a minimum of heating. The remaining solution was slowly heated to 85° C. for 1.5 h and then concentrated to dryness in vacuo to afford about 9.5 g of crude title product which can be used directly in subsequent reactions.

Step B: 1-Benzyloxycarbonyl-4-(t-butoxycarbonylamino) piperidine

A solution of 3.2 g (12.3 mmol) of (1-benzyloxycarbonylpiperidin-4-yl)isocyanate from Step A in 25 mL of DMF was slowly added to a suspension of $CuCl_3$ in 25 mL of DMF and 12 mL of t-butanol. The reaction was stirred for 24 h and then diluted with water and extracted twice with 1:1 ether: ethyl acetate. The organic layers were each washed with a portion of water and brine, dried over sodium sulfate, combined and concentrated. The residue was purified by FC eluting with 20% ethyl acetate in hexanes to afford 685 mg of title compound.

$^1$H NMR (400 MHz, $CDCl_3$): δ1.26 (m, 2H), 1.42 (s, 9H), 1.90 (br d, J=12, 2H), 2.90 (br t, 2H), 3.58 (m, 1H), 4.08 (m, 2H), 4.42 (br s, 1H), 5.09 (s, 2H), 5 H).

Step C: 1-Benzyloxycarbonyl-4-(N-(t-butoxycarbonyl-N-(ethyl)amino)piperidine

To a solution of 476 mg (1.42 mmol) of 1-benzyloxycarbonyl-4-(t-butoxycarbonylamino)piperidine from Step B and 0.24 mL (2.8 mmol) of ethyl iodide in 10 mL of DMF was added 85 mg (2.1 mmol) of 60% sodium hydride in mineral oil. The reaction was stirred for 16 h and was then poured into water and extracted three times with ether. The organic layers were each washed with a portion of water and brine, dried over sodium sulfate, combined and concentrated. The residue was purified by FC eluting with 15% ethyl acetate in hexanes to afford 409 mg of title compound.

$^1$H NMR (400 MHz, $CDCl_3$): δ1.06 (t, J=7, 3H), 1.44 (s, 9H), 1.5–1.7 (2 m, 4H), 2.78 (m, 2H), 3.1 (m, 2H), 4.10 (m, 1H), 4.25 (m, 2H), 5.10 (s, 2H), 7.33 (m, 5H).

Step D: 4-(N-(t-Butoxycarbonyl)-N-(ethyl)amino) piperidine

A solution of 400 mg (1.1 mmol) of 1-benzyloxycarbonyl-4-(N-(-t-butoxycarbonyl-N-(ethyl) amino)piperidine from Step C in 4 mL of methanol was hydrogenated with 40 mg of 10% Pd/C under a hydrogen balloon for 16 h. The reaction was filtered and concentrated in vacuo to give the title compound which was used directly in the next step.

Procedure 2

4-(N-Methoxycarbonyl-N-(ethyl)amino)piperidine
Step A: 1-Benzyloxycarbonyl-4-(methoxycarbonylamino) piperidine To a solution of 1.0 g (3.9 mmol) of (1-benzyloxycarbonylpiperidin-4-yl)isocyanate from Procedure 1, Step A in 10 mL of methanol was added 5 mg (cat) of DMAP. The reaction was stirred under nitrogen at rt for 24 h and then poured into water containing 2 mL of 2 N hydrochloric acid and was extracted twice with ethyl acetate. The organic layers were each washed with a portion of brine, dried over sodium sulfate, combined and concentrated to give 1.4 g of the crude title compound which can be used directly in subsequent reactions.

$^1$H NMR (400 MHz, $CDCl_3$): δ1.32 (m, 2H), 1.92 (br d, J=10, 4H), 2.91 (v br t, 2 H), 3.66 (br s, 3H), 4.10 (m, 1H), 4.58 (br s, 1H), 5.09 (s, 2H), 7.33 (m, 5H).

Step B: 1-Benzyloxycarbonyl-4-(N-methoxycarbonyl(N-ethyl)amino)piperidine

To 82 mg (0.28 mmol) of 1-benzyloxycarbonyl-4-(methoxycarbonylamino)piperidine from Step A and 0.045 mL (0.56 mmol) of ethyl iodide in 4 mL of DMF under nitrogen was added 22 mg (0.56 mmol) of 60% sodium hydride in mineral oil. The reaction was stirred at rt for 1 h and was then poured into water containing 1 mL of 2 N hydrochloric acid and extracted twice with ether. The organic layers were each washed with a portion of brine, dried over sodium sulfate, combined and concentrated. The residue was purified by FC eluting with 50% ethyl acetate in hexanes to afford 87 mg of title compound.

$^1$H NMR (400 MHz, CDCl$_3$): δ1.07 (t, J=7, 3H), 1.5–1.8 (m, 4H), 2.79 (m, 2H), 3.15 (m, 2H), 3.68 (s, 3H), 4.10 (m, 1H), 4.26 (m, 2H), 5.10 (s, 2H), 7.34 (m, 5H).

Step C: 4-(N-Methoxycarbonyl-N-(ethyl)amino)piperidine

Using essentially the same procedure as in Procedure 1, Step D, 85 mg (0.27 mmol) of 1-benzyloxycarbonyl-4-(N-(methoxycarbonyl)-N-(ethyl)amino)piperidine from Step B was hydrogenated to afford 37 mg of the title compound.

Procedure 3

4-(Dimethylaminocarbonylamino)piperidine

Step A: 1-Benzyloxycarbonyl-4-(dimethylaminocarbonylamino)piperidine

To 0.83 g (3.2 mmol) of (1-benzyloxycarbonylpiperidin-4-yl)isocyanate from Procedure 1, Step A in 10 mL was added 16 mL (32 mmol) of 2 M dimethylamine in THF. The reaction was stirred under nitrogen at rt for 24 h and then poured into water containing 20 mL of 2 N hydrochloric acid and was extracted twice with ethyl acetate. The organic layers were each washed with a portion of brine, dried over sodium sulfate, combined and concentrated to give 0.95 g of the crude title compound which can be used directly in subsequent reactions.

$^1$H NMR (400 MHz, CDCl$_3$): δ1.25 (m, 2H), 1.95 (br d, J=10, 2H), 2.86 (br s, 6 H+2H), 3.79 (m, 1H), 4.04.25 (m, 3H), 5.09 (s, 2H), 7.35 (m, 5H).

Step B: 4-(Dimethylaminocarbonylamino)piperidine

Using essentially the same procedure as in Procedure 1, Step D, 1.4 g (4.6 mmol) of 1-benzyloxycarbonyl-4-(dimethylaminocarbonylamino)piperidine from Step A was hydrogenated to afford 690 mg of the title compound.

Procedure 4

4-(N-(Benzyloxycarbonyl)-N-(prop-1-yl)amino)piperidine

Step A: 4-Azido-1-t-butoxycarbonylpiperidine

To a solution of 45.3 g (172 mmol) of 4-bromo-1-t-butoxycarbonylpiperidine in 750 mL of DMF was added 22.3 g (343 mmol) of sodium azide and 2.5 g (17 mmol) of sodium iodide. The reaction was stirred at rt for 24 h and then at 60° C. for 4 h. The mixture was poured into water containing 20 mL of sodium bicarbonate and extracted twice with 1:1 ether:hexanes. The organic layers were each washed with a portion of water and brine, dried over sodium sulfate, combined and concentrated. The residue was purified by FC eluting with 5–10% ethyl acetate in hexanes to afford 39 g of title compound having a trace of elimination byproduct.

$^1$H NMR (400 MHz, CDCl$_3$): δ1.43 (s, 9H), 1.52 (m, 2H), 1.85 (m, 2H), 3.07 (m, 2H), 3.55 (m, 1H), 3.78 (m, 2H).

Step B: 4-Amino-1-t-butoxycarbonylpiperidine

A solution of 4.05 g (17.9 mmol) of 4-azido-1-t-butoxycarbonylpiperidine from Step A in 50 mL of methanol was hydrogenated with 350 mg of 10% Pd/C under a hydrogen balloon for 16 h when the reaction was complete by TLC (10% ethyl acetate in hexanes). The catalyst was filtered off and the volatiles removed in vacuo to give 3.5 g of title compound which was used directly in subsequent reactions.

Step C: 4-Benzyloxycarbonylamino-1-t-butoxycarbonylpiperidine

To a solution of 1.2 g (6.0 mmol) 4-amino-1-t-butoxycarbonylpiperidine from Step B in 40 mL of methylene chloride was added 3.15 mL (18 mmol) of DIPEA and 1.03 mL (7.2 mmol) of benzyl chloroformate while cooled in an ice bath. After 0.5 h the reaction was quenched with aqueous sodium carbonate and extracted three times with methylene chloride. The organic layers were each washed with a portion of brine, dried over sodium sulfate, combined and concentrated. The residue was purified by FC eluting with 25% ethyl acetate in hexanes to afford 1.94 g of title compound.

$^1$H NMR (400 MHz, CDCl$_3$): δ1.26 (m, 2H), 1.42 (s, 9H), 1.90 (br d, J=12, 2H), 2.90 (br t, 2H), 3.58 (m, 1H), 4.08 (m, 2H), 4.42 (br s, 1H), 5.09 (s, 2H), 7.33 (m, 5 H).

Step D: 4-(N-(Benzyloxycarbonyl)-N-((prop-1-yl)amino)-1-t-butoxycarbonylpiperidine To 110 mg (0.32 mmol) 4-benzyloxycarbonylamino-1-t-butoxycarbonylpiperidine from Step C and 0.16 mL (1.6 mmol) of n-propyl iodide in 2 mL of DMF under nitrogen was added 26 mg (0.65 mmol) of 60% sodium hydride in mineral oil. The reaction was stirred at rt for 16 h and was then poured into water and extracted twice with ether. The organic layers were each washed with a portion of brine, dried over sodium sulfate, combined and concentrated. The residue was purified by FC eluting with 20% ethyl acetate in hexanes to afford 90 mg of title compound.

Step E: 4-(N-(Benzyloxycarbonyl)-N-(prop-1-yl)amino)piperidine hydrochloride salt To a solution of 2.4 mmol of HCl in 2 mL of methanol (prepared by the addition of 0.17 mL of acetyl chloride at 0° C. and stirring for 10 min) was added 90 mg of 4-(N-(benzyloxycarbonyl)-N-(prop-1-yl)amino)-1-t-butoxycarbonylpiperidine. The mixture was stirred at rt for 16 h at which time the reaction was complete by TLC (20% ethyl acetate in hexanes) and was evaporated to dryness in vacuo to afford 75 mg of the title compound as the hydrochloride salt.

Procedure 5

4-(N-(Benzyloxycarbonyl)-N-(allyl)amino)piperidine hydrochloride

Step A: 4-(N-(Benzyloxycarbonyl)-N-(allyl)amino)-1-(t-butoxycarbonyl)piperidine

Sodium hydride (47 mg of 60% oil dispersion, 1.2 mmol) was added to a solution of 4-(benzyloxycarbonylamino)-1-(t-butoxycarbonyl)piperidine (200 mg, 0.598 mmol) from Procedure 4, Step C and allyl bromide (0.251 mL, 351 mg, 2.9 mmol) in 2.0 mL of DMF, and the reaction was stirred overnight at rt. The reaction mixture was poured into 20 mL of water and extracted with 3×20 mL of ethyl ether. The combined organic layers were washed with 30 mL of brine, dried over sodium sulfate, and evaporated. The crude product was purified by flash column chromatography on silica gel, eluting with 20% ethyl acetate in hexane, to give 246 mg of the title compound as a viscous oil.

Mass spectrum (ESI): m/z=275 (M-99, 100%).

Step B: 4-(N-(Benzyloxycarbonyl)-N-(allyl)amino)piperidine hydrochloride

Acetyl chloride (0.467 mL, 516 mg, 6.57 mmol) was added to 2.0 mL of methanol at 0° C. and the mixture was stirred for 10 min to give a solution of HCl. 4-(N-(Benzyloxycarbonyl)allylamino)-1-(t-butoxycarbonyl)piperidine from Step A (123 mg, 0.33 mmol) was then added and the resulting solution was stirred for 1 h at 0° C. and 1 h at rt. The solution was evaporated to give the title compound as a crystalline solid in quantitative yield.

¹H NMR (400 MHz, CD₃OD): δ7.39–7.28 (m, 5H), 5.84 (ddt, 1H, J=17, 10, 5 Hz), 5.21–5.10 (m, 4H), 4.10–3.98 (m, 1H), 3.90 (d, 2H, J=5 Hz), 3.43 (br d, 2 H, J=13 Hz), 3.04 (br t, 2H, J 13 Hz), 2.18–2.02 (m, 2H), 1.93 (d, 2H, J=13 Hz).

Mass spectrum (CI): m/z=275 (M+1, 100%).

Procedure 6

4-(N-(4-Nitrobenzyloxycarbonyl)-N-(allyl)amino) piperidine hydrochloride

Step A: 1-(t-Butoxycarbonyl)-4-(N-(4-nitrobenzyloxycarbonyl)-N-(allyl)amino)piperidine Allylamine (0.45 mL, 0.34 g, 6.0 mmol), acetic acid (0.300 mL, 315 mg, 5.24 mmol), and 3 Å molecular sieves (2.00 g) were added to a solution of 1-(t-butoxycarbonyl)-4-piperidone (1.00 g, 5.01 mmol) in 14 n L of 1,2-dichloroethane. After stirring 0.5 h at rt, sodium triacetoxyborohydride (1.62 g, 7.6 mmol) was added in two portions 5 min apart. After an additional 3 h, the mixture was partitioned between 30 mL of ethyl acetate and 20 mL of saturated aqueous sodium bicarbonate. The aqueous layer was extracted with 30 mL of ethyl acetate and the organic layers were washed in succession with 20 mL of brine, combined, dried over sodium sulfate, and evaporated to give 1.20 g of crude 4-(allylamino)-1-(t-butoxycarbonyl) piperidine as a yellow syrup.

A portion of the crude 4-(allylamino)-1-(t-butoxycarbonyl)piperidine (400 mg, 1.66 mmol) was dissolved in 10 mL of dichloromethane and treated with N,N-diisopropylethylamine (0.700 mL, 519 mg, 4.0 mmol) and 4-nitrobenzyl chloroformate (392 mg, 1.82 mmol). After stirring 3 h at rt, the mixture was diluted with 30 mL of ethyl acetate and washed with 15 mL each of 2 N aqueous HCl, saturated aqueous sodium bicarbonate, and brine. The organic layer was dried over sodium sulfate, and evaporated. The residue was purified by flash column chromatography on silica gel, eluting with 30% ethyl acetate in hexane, to give 572 mg of the title compound as a colorless syrup.

¹H NMR (400 MHz, CDCl₃): δ8.22 (d, 2H, J=8 Hz), 7.50 (d, 2H, J=8 Hz), 5.80 (ddt, 1H, J=17, 10, 5 Hz), 5.23 (s, 2H), 5.18–5.09 (m, 2H), 4.27–4,08 (m, 3H), 3.89–3.79 (m, 2H), 2.79–2.66 (m, 2H), 1.74–1.52 (m, 4H), 1.46 (s, 9H).

Mass spectrum (ESI): m/z=420 (M+1, 27%), 437 (M+1+ NH₃, 100%).

Step B: 4-(N-(4-Nitrobenzyloxycarbonyl)-N-(allyl)amino) piperidine hydrochloride The title compound was prepared according to the procedure of Procedure 4, Step E, replacing 4-(N-(benzyloxycarbonyl)-N-(ethyl)amino)-1-(t-butoxycarbonyl) piperidine with 1-(t-butoxycarbonyl)-4-(N-(4-nitrobenzyloxycarbonyl)-N-(allyl)amino)piperidine.

¹H NMR(400MHz, CD₃OD): δ8.24 (d,2H,J=8 Hz), 7.60 (d,2H,J=8 Hz), 5.87 (ddt, 1H, J=17, 10, 5 Hz), 5.27 (s, 2H), 5.23–5.13 (m, 2H), 4.14–3.94 (m, 1 H), 3.94 (d, 2H, J=5 Hz), 3.45 (d, 2H, J=13 Hz), 3.06 (t, 2H, J=13 Hz), 2.20–2.03 (m, 2H), 2.02–1.90 (m, 2H).

Mass spectrum (ESI): m/z=320 (M+1, 93%).

Procedure 7

The following substituted piperidines were prepared following the procedures described in Procedure 2 but substituting the appropriate alcohol and/or alkylating agent in Step A and B.

4-(N-(Methoxycarbonyl)-N-(hex-1-yl)amino)piperidine
4-(N-(Methoxycarbonyl)-N-(3,5,5-trimethylhex-1-yl) amino)piperidine
4-(N-(Ethoxycarbonyl)-N-(cyclohexylmethyl)amino) piperidine Procedure 8

The following substituted piperidines were prepared following the procedures described in Procedure 4 but substituting the appropriate alkyl bromide or iodide for n-propyl iodide in Step D.

4-(N-(Benzyloxycarbonyl)-N-(ethyl)amino)piperidine hydrochloride
4-(N-(Benzyloxycarbonyl)-N-(2-methylprop-1-yl)amino) piperidine hydrochloride
4-(N-(Benzyloxycarbonyl)-N-(ethyl)amino)piperidine hydrochloride
4-(N-(Benzyloxycarbonyl)-N-(prop-2-yl)amino)piperidine hydrochloride
4-(N-(Benzyloxycarbonyl)-N-(cyclopropylmethyl)amino) piperidine hydrochloride
4-(N-(Benzyloxycarbonyl)-N-(1-methylprop-1-yl)amino) piperidine hydrochloride Procedure 9

The following substituted piperidines were prepared following the procedures described in Procedure 6 but substituting the appropriate alkyl amine and/or acylating agent in Step A.

4-(N-(3-Nitrobenzyloxycarbonyl)-N-(propargyl)amino) piperidine hydrochloride
4-(N-(2-Nitrobenzyloxycarbonyl)-N-(propargyl)amino) piperidine hydrochloride
4-(N-(4-Nitrobenzylaminocarbonyl)-N-(allyl)amino) piperidine hydrochloride
4-(N-(3-Nitrobenzylaminocarbonyl)-N-(allyl)amino) piperidine hydrochloride
4-(N-(2-Nitrobenzylaminocarbonyl)-N-(allyl)amino) piperidine hydrochloride
4-(N-(4-Nitrobenzylcarbonyl)-N-(allyl)amino)piperidine hydrochloride
4-(N-(3-Nitrobenzylcarbonyl)-N-(allyl)amino)piperidine hydrochloride
4-(N-(4-Nitrobenzyloxycarbonyl)-N-(propargyl)amino) piperidine hydrochloride
4-(N-(Benzyloxycarbonyl)-N-(prop-1-yl)amino)piperidine hydrochloride
4-(N-(Phenylcarbonyl)-N-(prop-1-yl)amino)piperidine hydrochloride
4-(N-(Benzylcarbonyl)-N-(prop-1-yl)amino)piperidine hydrochloride
4-(N-(Cyclohexyloxycarbonyl)-N-(prop-1-yl)amino) piperidine hydrochloride
4-(N-(2-Phenyleth-1-yloxycarbonyl)-N-(prop-1-yl)amino) piperidine hydrochloride
4-(N-(3-Phenylprop-1-yloxycarbonyl)-N-(prop-1-yl)amino) piperidine hydrochloride
4-(N-(4-Phenylbenzyloxycarbonyl)-N-(prop-1-yl)amino) piperidine hydrochloride
4-(N-(2-Naphthylmethyloxycarbonyl)-N-(prop-1-yl)amino) piperidine hydrochloride
4-(N-(1-Naphthylmethyloxycarbonyl)-N-(prop-1-yl)amino) piperidine hydrochloride
4-(N-(4-Methylbenzyloxycarbonyl)-N-(prop-1-yl)amino) piperidine hydrochloride
4-(N-(4-Methylbenzyloxycarbonyl)-N-(prop-1-yl)amino) piperidine hydrochloride
4-(N-(Butyloxycarbonyl)-N-(prop-1-yl)amino)piperidine hydrochloride 4-(N-(Benzylaminocarbonyl)-N-(prop-1-yl)amino) piperidine hydrochloride Procedure 10

The following set of 70 substituted piperidines were prepared as their di-TFA salts following the procedures described in Procedure 6 but substituting the appropriate alkyl amine and acylating agent in Step A and using TFA at rt in Step B.

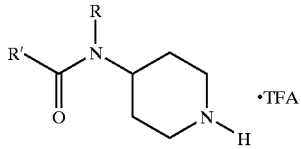

R=
  Methyl
  Ethyl
  n-Propyl
  n-Butyl
  Allyl
  Cyclopropylmethyl
  2-Methylcycloprop-1-yl
R'=
  Benzyloxy
  4-Nitrobenzyloxy
  2-Phenyleth-1-yloxy
  2-(4-Nitrophenyl)eth-1-yloxy
  Benzylamino
  4-Nitrobenzylamino
  2-Phenyleth-1-yl
  2-(4-Nitrophenyl)eth-1-yl
  Phenoxymethyl
  4-Nitrophenoxymethyl

EXAMPLE 1

N-(1-(SR)-3-(SR)-((4-(N-(Benzylaminocarbonyl)-N-(prop-1-yl)amino)piperidin-1-yl)methyl)-4-(SR)-phenylcyclopent-1-yl)glycine di-hydrochloride salt and N-(1-(RS)-3-(SR)-((4-(N-(benzylaminocarbonyl)-N-(prop-1-yl)amino) piperidin-1-yl)methyl)-4-(SR)-phenylcyclopent-1-yl) glycine di-hydrochloride salt Step A: Methyl (+-)-trans-4-methylene-2-phenylcyclopentanoate A mixture of methyl trans-cinnamate (5.0 g, 31 mmol), tetrakis(triphenylphosphine) palladium(0) (2.6 g, 2.3 mmol), 1,2-bis(diphenylphosphino)ethane (0.70 g, 1.8 mmol) and 2-((trimethylsilyl)methyl)-2-propen-1-yl acetate (6.90 g, 37 mmol) in THF (60 mL) under argon was heated to reflux for 4 h. An additional aliquot of 2-((trimethylsilyl)methyl)-2-propen-1-yl acetate (3.40 g) was added and the reaction was continued for another 16 h. The volatiles were then removed in vacuo and the residue was purified by FC (10% ethyl acetate in hexanes) to afford the title compound (6.2 g).

NMR (CDCl$_3$) δ: 2.52 (m, 1H), 2.68 (m, 1H), 2.75–2.9 (m, 2H), 2.95 (ddd, 1H), 3.45 (ddd, 1H), 3.57 (s, 3H), 4.92 (m, 2H), 7.15–7.3 (m, 5H).

Step B: (+-)-trans-1-Hydroxymethyl-4-methylene-2-phenylcyclopentane

To a solution of methyl (+-)-trans-4-methylene-2-phenylcyclopentanoate (5.0 g, 23 mmol) from Step A in THF (30 mL) under nitrogen was added dropwise over 10 min 1M lithium aluminum hydride (LAH) in THF (23 mL). After 2 h at rt, the excess LAH was quenched by dropwise addition of ethyl acetate and the reaction was then poured into dilute aq. HCl. The mixture was extracted twice with ether and the organic layers were washed with brine, dried over sodium sulfate, combined and concentrated. The residue was purified by FC (20–30% ethyl acetate in hexanes) to afford the title product (4.5 g) as a white solid.

Step C: (+-)-trans-4-Methylene-2-phenylcyclopentanecarboxaldehyde

To a solution of oxalyl chloride (1.16 mL, 13.3 mmol) in methylene chloride (50 mL) at −70° C. was added dropwise DMSO (1.88 mL, 26.6 mmol). After 15 min, a solution of (+-)-trans-1-hydroxymethyl-4-methylene-2-phenylcyclopentane from Step B (1.0 g, 5.3 mmol) in methylene chloride (10 mL) was added. The reaction was stirred at −70° C. for 1.5 h and then DIPEA (9.25 mL, 53 mmol) in methylene chloride (10 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (20% ethyl acetate in hexanes) to give the title product (0.88 g) after vacuum drying.

Step D: 1-Methylene-3-(SR)-((4-(N-(benzylaminocarbonyl)-N-(prop-1-yl)amino)piperidin-1-yl)methyl)-4-(SR)-phenylcyclopentane To a solution of (+-)-trans-4-methylene-2-phenylcyclopentanecarboxaldehyde from Step C (880 mg, 4.7 mmol) in 1,2-dichloroethane (50 mL) was added 4-(N-(benzylaminocarbonyl)-(N-prop-1-yl)amino)piperidine hydrochloride (1.62 g, 5.2 mmol) and DIPEA (1.0 mL, 5.7 mmol). After 15 min, sodium triacetoxyborohydride (2.0 g, 9.5 mmol) was added and the reaction was stirred at rt for 4 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with 60% ethyl acetate in hexanes to give the title product (1.8 g) as the free amine. MS (NH$_3$/ESI): m/z 448 (M +1).

Step E: 3-(SR)-((4-(N-(Benzylaminocarbonyl)-N-(prop-1-yl)amino)piperidin-1-yl)methyl)-4-(SR)-phenylcyclopentan-1-one To a solution of 1-methylene-3-(SR)-((4-(N-(benzylaminocarbonyl)-N-(prop-1-yl)amino)piperidin-1-yl)methyl)-4-(SR)-phenylcyclopentane from Step D (1.8 g, 4.0 mmol) in methanol (50 mL) was added 1M hydrogen chloride in ether (6.0 mL, 6.0 mmol). The solution was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to rt over 16 h. The volatiles were removed in vacuo and the residue was purified by FC (ethyl acetate, then 1% DIPEA in ethyl acetate) to give the title compound (1.13 g).

Step F: N-(1-(SR)-3-(SR)-((4-(N-(Benzylaminocarbonyl)-N-(prop-1-yl)amino)piperidin-1-yl)methyl)-4-(SR)-phenylcyclopent-1-yl)glycine t-butyl ester (higher R$_f$) and N-(1-(RS)-3-(SR)-((4-(N-(benzylaminocarbonyl)-N-(prop-1-yl)amino)piperidin-1-yl)methyl)-4-(SR)-phenylcyclopent-1-yl)glycine t-butyl ester (lower R$_f$)

To a solution of 3-(SR)-((4-(N-(benzylaminocarbonyl)-N-(prop-1-yl)amino)piperidin-1-yl)methyl)-4-(SR)- phenylcyclopentan-1-one (52 mg, 0.12 mmol) from Step E, glycine t-butyl ester hydrochloride (60 mg, 0.36 mmol) and DIPEA (0.063 mL, 0.36 mmol) in 1,2-dichloroethane (2 mL) at rt was added sodium triacetoxyborohydride (100 mg, 0.47 mmol). The reaction was stirred at rt for 16 h and was then diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 75% ethyl acetate in hexanes to give separation of the two C-1 diastereomeric racemic title products as the free amines. The stereochemistry for each was assigned based on the results of Example 6, 7 and 8.

(higher $R_f$): MS (NH$_3$/ESI): m/z 563 (M+1).

(lower $R_f$): MS (NH$_3$/ESI): m/z 563 (M+1).

Step G: N-(1-(SR)-3-(SR)-((4-(N-(Benzylaminocarbonyl)-N-(prop-1-yl)amino)piperidin-1-yl)methyl)4-(SR)-phenylcyclopent-1-yl)glycine di-hydrochloride salt (from higher $R_f$) and N-(1-(RS)-3-(SR)-((4-(N-(benzylaminocarbonyl)-N-(prop-1-yl)amino)piperidin-1-yl)methyl)4-(SR)-phenylcyclopent-1-yl)glycine di-hydrochloride salt (from lower $R_f$)

The individual diastereomers from Step F were each taken up in 1:1 methylene chloride:ether (2 mL) and 1M hydrogen chloride in ether (1 mL) was added. After 3 days at rt the volatiles were removed under nitrogen to give the title racemic compounds as white solids.

(from higher $R_f$): MS (NH$_3$/ESI): m/z 507 (M+1).

(from lower $R_f$): MS (NH$_3$/ESI): m/z 507 (M+1).

EXAMPLE 2

N-Methyl-N-(1-(SR)-3-(SR)-((4-(N-(benzylaminocarbonyl)-N-(prop-1-yl)amino)piperidin-1-yl)methyl)4-(SR)-phenylcyclopent-1-yl)glycine di-hydrochloride salt and N-methyl-N-(1-(RS)-3-(SR)-((4-(N-(benzylaminocarbonyl)-N-(prop-1-yl)amino)piperidin-1-yl)methyl)-4-(SR)-phenylcyclopent-1-yl)glycine di-hydrochloride salt Using essentially the same procedures as in Example 1, Step F and G, but substituting N-methyl glycine t-butyl ester hydrochloride in Step F, the two individual diastereomeric racemic title compounds were obtained but the stereochemistries for each were not assigned.

(Each isomer): MS (NH$_3$/ESI): m/z 521 (M+1).

EXAMPLE 3

N-(1-(SR and RS)-3-(SR)-((4-(N-(Benzylaminocarbonyl)-N-(prop-1-yl)amino)piperidin-1-yl)methyl)-4-(SR)-phenylcyclopent-1-yl)-D-alanine di-hydrochloride salt and N-(1-(RS and SR)-3-(RS)-((4-(N-(benzylaminocarbonyl)-N-(prop-1-yl)amino)piperidin-1-yl)methyl)4-(RS)-phenylcyclopent-1-yl)-D-alanine di-hydrochloride salt Using essentially the same procedures as in Example 1, Step F and G, but substituting D-alanine t-butyl ester hydrochloride in Step F, partial separation of the four possible diastereomeric title compounds into three fractions was achieved but the purities and stereochemistries for each were not assigned.

(Each isomer): MS (NH$_3$/ESI): m/z 521 (M+1).

EXAMPLE 4

N-(1-(SR and RS)-3-(SR)-((4-(N-(Benzylaminocarbonyl)-N-(prop-1-yl)amino)piperidin-1-yl)methyl)-4-(SR)-phenylcyclopent-1-yl)-L-alanine di-hydrochloride salt and N-(1-(RS and SR)-3-(RS)-((4-(N-(benzylaminocarbonyl)-N-(prop-1-yl)amino)piperidin-1-yl)methyl)-4-(RS)-phenylcyclopent-1-yl)-L-alanine di-hydrochloride salt Using essentially the same procedures as in Example 1, Step F and G, but substituting L-alanine t-butyl ester hydrochloride in Step F, partial separation of the four possible diastereomeric title compounds into three fractions was achieved but the purities and stereochemistries for each were not assigned.

(Each isomer): MS (NH$_3$/ESI): m/z 521 (M+1).

EXAMPLE 5

N-(1-(SR and RS)-3-(SR)-((4-(N-(Benzylaminocarbonyl)-N-(prop-1-yl)amino)piperidin-1-yl)methyl)-4-(SR)-phenylcyclopent-1-yl)-L-phenylalanine di-hydrochloride salt and N-(1-(RS and SR)-3-(RS)-((4-(N-(benzylaminocarbonyl)-N-(prop-1-yl)amino)piperidin-1-yl)methyl)-4-(RS)-phenylcyclopent-1-yl)-L-phenylalanine di-hydrochloride salt Using essentially the same procedures as in Example 1, Step F and G, but substituting L-phenylalanine t-butyl ester hydrochloride in Step F, partial separation of the four possible diastereomeric title compounds into two fractions was achieved but the purities and stereochemistries for each were not assigned.

(Each isomer): MS (NH$_3$/ESI): m/z 597 (M+1).

EXAMPLE 6

N-(-(S)-3-(R)-((4-(N-(4-Nitrobenzyloxycarbonyl)-N-(allyl)amino)piperidin-1-yl)methyl)-4-(R)-phenylcyclopent-1-yl)-L-leucine (Isomer 6A), N-(1-(S)-3-(S)-((4-(N-(4-nitrobenzyloxycarbonyl)-N-(allyl)amino)piperidin-1-yl)methyl)-4-(S)-phenylcyclopent-1-yl)-L-leucine (Isomer 6B), N-(1-(R)-3-(S)-((4-(N-(4-nitrobenzyloxycarbonyl)-N-(allyl)amino)piperidin-1-yl)methyl)-4-(S)-phenylcyclopent-1-yl)-L-leucine (Isomer 6C) and N-(1-(R)-3-(R)-((4-(N-(4-nitrobenzyloxycarbonyl)-N-(allyl)amino)piperidin-1-yl)methyl)-4-(R)-phenylcyclopent-1-yl)-L-leucine (Isomer 6D) di-TFA salts Step A: (+−)-trans4-Methylene-2-phenylcyclopentanoic acid To a solution of methyl (+−)-trans-4-methylene-2-phenylcyclopentanoate prepared as in Example 1, Step A (28.4 g, 131 mmol) in methanol (400 mL) was added 5N sodium hydroxide (131 mL, 656 mmol). The reaction was heated at 65° C. for 1 h then cooled and concentrated. The residue was diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+−)-trans-1-Hydroxymethyl-4-methylene-2-phenylcyclopentane

To a solution of (+−)-trans-4-methylene-2-phenylcyclopentanoic acid (26 g, 129 mmol) from Step A in THF (600 mL) under nitrogen at −10° C. was added dropwise over 15 min 1M lithium aluminum hydride (LAH) in THF (193 mL, 193 mmol). After 16 h at rt, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title product (23.8 g) as an oil.

Step C: (+−)-trans-1-Hydroxymethyl-4-oxo-2-phenylcyclopentane

Into a solution of (+−)-trans-1-hydroxymethyl-4-methylene-2-phenylcyclopentane from Step B (22.7 g, 121 mmol) in methanol (200 mL) cooled in a dry ice/acetone bath was bubbled ozone until the blue color persisted. The excess ozone was removed with a stream of nitrogen and then dimethylsulfide (20 mL) was added. After 10 min, the bath was removed and the reaction was allowed to warm to rt over 16 h. The volatiles were removed in vacuo and the residue was purified by FC (15–30% ethyl acetate in hexanes) to give the title compound (22.1 g).

Step D: (+−)-trans-4-Oxo-2-phenylcyclopentanecarboxaldehyde

To a solution of oxalyl chloride (1.15 mL, 13.1 mmol) in methylene chloride (30 mL) at −70° C. was added dropwise DMSO (1.87 mL, 26.3 mmol). After 15 min, a solution of (+−)-trans-1-hydroxymethyl-4-oxo-2-phenylcyclopentane from Step C (1.0 g, 5.26 mmol) in methylene chloride (10 mL) was added. The reaction was stirred at −70° C. for 1.5 h and then DIPEA (9.25 mL, 53 mmol) in methylene chloride (10 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (30% ethyl acetate in hexanes) to give the title product (0.9 g) after vacuum drying.

Step E: 3-(SR)-((4-(N-(4-Nitrobenzyloxycarbonyl)-N-(allyl)amino)piperidin-1-yl)methyl)4-(SR)-phenylcyclopentan-1-one di-hydrochloride salt To a solution of (+−)-trans4-oxo-2-phenylcyclopentanecarboxaldehyde from Step D (327 mg, 1.74 mmol) in 1,2-dichloroethane (20 mL) was added 4-(N-(4-nitrobenzyloxycarbonyl)(N-allyl)amino)piperidine hydrochloride (667 mg, 1.9 mmol) and DIPEA (0.36 mL, 2.1 mmol). After 5 min, sodium triacetoxyborohydride (740 mg, 3.5 mmol) was added and the reaction was stirred at rt for 4 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with a gradient of 35 to 75% ethyl acetate in hexanes to give the title product (365 mg) as the free amine. This was taken up in ether and 1M hydrogen chloride in ether (0.5 mL) was added to form the di-hydrochloride salt. The volatiles were removed in vacuo to give the title salt.

MS (NH$_3$/ESI): m/z 492 (M+1).

Step F: N-(1-(S)-3-(R)-((4-(N-(4-Nitrobenzyloxycarbonyl)-N-(allyl)amino)piperidin-1-yl)methyl)-4-(R)-phenylcyclopent-1-yl)-L-leucine t-butyl ester (Isomer A), N-(1-(S)-3-(S)-((4-(N-(4-nitrobenzyloxycarbonyl)-N-(allyl)amino)piperidin-1-yl)methyl)-4-(S)-phenylcyclopent-1-yl)-L-leucine t-butyl ester (Isomer B), N-(1-(R)-3-(S)-((4-(N-(4-nitrobenzyloxycarbonyl)-N-(allyl)amino)piperidin-1-yl)methyl)-4-(S)-phenylcyclopent-1-yl)-L-leucine t-butyl ester (Isomer C) and N-(1-(R)-3-(R)-((4-(N-(4-nitrobenzyloxycarbonyl)-N-(allyl)amino)piperidin-1-yl)methyl)-4-(R)-phenylcyclopent-1-yl)-L-leucine t-butyl ester (Isomer D)

To a solution of 3-(SR)-((4-(N-(4-nitrobenzyloxycarbonyl)-N-(allyl)amino)piperidin-1-yl)methyl)-4-(SR)-phenylcyclopentan-1-one (52 mg, 0.10 mmol) from Step E, L-leucine t-butyl ester hydrochloride (65 mg, 0.29 mmol) and DIPEA (0.069 mL, 0.40 mmol) in 1,2-dichloroethane (2 mL) at rt was added sodium triacetoxyborohydride (41 mg, 0.20 mmol). The reaction was stirred at rt for 16 h and was then diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting first with 75% ethyl acetate in hexanes to give partial separation of the four diastereomeric title products. Prep TLC was repeated with 40% ethyl acetate in hexanes for each band to give clean highest R$_f$ product (Isomer A), a mixture of the middle R$_f$ products (Isomers B and C), and clean lowest R$_f$ product (Isomer D) as the free amines.

(higher R$_f$): HPLC/MS (ESI): m/z 663 (M+1).

(middle R$_f$): HPLC/MS (ESI): m/z 663 (M+1) (2 isomers seen).

(lower R$_f$): HPLC/MS (ESI): m/z 663 (M+1).

Step G: N-(1-(S)-3-(R)-((4-(N-(4-Nitrobenzyloxycarbonyl)-N-(allyl)amino)piperidin-1-yl)methyl)-4-(R)-phenylcyclopent-1-yl)-L-leucine (Isomer 6A), N-(1-(S)-3-(S)-((4-(N-(4-nitrobenzyloxycarbonyl)-N-(allyl)amino)piperidin-1-yl)methyl)4-(S)-phenylcyclopent-1-yl)-L-leucine (Isomer 6B), N-(1-(R)-3-(S)-((4-(N-(4-nitrobenzyloxycarbonyl)-N-(allyl)amino)piperidin-1-yl)methyl)-4-(S)-phenylcyclopent-1-yl)-L-leucine (Isomer 6C) and N-(1-(R)-3-(R)-((4-(N-(4-nitrobenzyloxycarbonyl)-N-(allyl)amino)piperidin-1-yl)methyl)-4-(R)-phenylcyclopent-1-yl)-L-leucine (Isomer 6D) di-TFA salts The 2 individual diastereomers and the mixed diastereomers from Step F were each taken up in 1:1 methylene chloride:ether (2 mL) and 1M hydrogen chloride in ether (1 mL) was added. After 3 days at rt the volatiles were removed under nitrogen to give the title compounds as white solids. These were analyzed by HPLC (Advantage 4.6×150 mm C-18 column, using a gradient of 10% A:90% B to 35% A:65% B over 30 min; A=0.5% TFA in water, B=0.5% TFA in acetonitrile) and purified by Prep HPLC (Combi Prep 20×50 mm C-18). Evaporation of the clean fractions to dryness afforded the title compounds as their di-TFA salts.

Isomer A (from highest R$_f$): HPLC/MS (ESI): m/z 607 (M+1), R$_t$=25.5 min

Isomer B (from middle R$_f$): HPLC/MS (ESI): m/z 607 (M+1), R$_t$=25.2 min.

Isomer C (from middle R$_f$): HPLC/MS (ESI): m/z 607 (M+1), R$_t$=25.9 min.

Isomer D (from lowest R$_f$): HPLC/MS (ESI): m/z 607 (M+1), R$_t$=25.2 min.

EXAMPLE 7

N-(1-(R)-3-(S)-((4-(N-(4-Nitrobenzyloxycarbonyl)-N-(allyl)amino)piperidin-1-yl)methyl)-4-(S)-phenylcyclopent-1-yl)-D-leucine (Isomer 7E), N-(1-(R)-3-(R)-((4-(N-(4-nitrobenzyloxycarbonyl)-N-(allyl)amino)piperidin-1-yl)methyl)-4-(R)-phenylcyclopent-1-yl)-D-leucine (Isomer 7F), N-(1-(S)-3-(R)-((4-(N-(4-nitrobenzyloxycarbonyl)-N-(allyl)amino)piperidin-1-yl)methyl)-4-(R)-phenylcyclopent-1-yl)-D-leucine (Isomer 7G) and N-(1-(S)-3-(S)-((4-(N-(4-nitrobenzyloxycarbonyl)-N-(allyl)amino)piperidin-1-yl)methyl)4-(S)-phenylcyclopent-1-yl)-D-leucine (Isomer 7H) di-TFA salts Using essentially the same procedures as in Example 6, Step F and G, but substituting D-leucine t-butyl ester hydrochloride in Step F, the four title diastereomers were obtained which were enantiomeric to those of Example 6.

Isomer E (from highest $R_f$): HPLC/MS (ESI): m/z 607 (M+1), $R_t$=25.5 min

Isomer F (from middle $R_f$): HPLC/MS (ESI): m/z 607 (M+1), $R_t$=25.2 min.

Isomer G (from middle $R_f$): HPLC/MS (ESI): m/z 607 (M+1), $R_t$=25.9 min.

Isomer H (from lowest $R_f$): HPLC/MS (ESI): m/z 607 (M+1), $R_t$=25.2 min.

EXAMPLE 8

N-(1-(S)-3-(S)-((4-(N-(4-Nitrobenzyloxycarbonyl)-N-(allyl)amino)piperidin-1-yl)methyl)-4-(S)-phenylcyclopent-1-yl)-L-leucine (Isomer 6B) and N-(1-(S)-3-(S)-((4-(N-(4-nitrobenzyloxycarbonyl)-N-(allyl)amino)piperidin-1-yl)methyl)-4-(S)-phenylcyclopent-1-yl)-D-leucine (Isomer 7H) di-TFA salts Step A: (+−)-trans-4-Methylene-2-phenylcyclopentanoic acid To a solution of methyl (+−)-trans-4-methylene-2-phenylcyclopentanoate prepared as in Example 1, Step A (28.4 g, 131 mmol) in methanol (400 mL) was added 5N sodium hydroxide (131 mL, 656 mmol). The reaction was heated at 65° C. for 1 h then cooled and concentrated. The residue was diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+)-trans-4-Methylene-2-phenylcyclopentanoic acid, (S)-(−)-α-methylbenzylamine salt and (−)-trans4-methylene-2-phenylcyclopentanoic acid, (R)-(+)-α-methylbenzylamine salt The crude (+−)-trans4-methylene-2-phenylcyclopentanoic acid from Step A (assumed 131 mmol) was taken up in 2-propanol (400 mL), warmed to 80° C. and treated with (S)-(−)-α-methylbenzylamine (8.45 mL, 66 mmol). The mixture was stirred while allowed to cool to rt over 16 h and was then cooled to −10° C. for 1 h. The salt was filtered, washed with a small amount of ether to remove 2-propanol and air dried to give 6.442 g of salt. This was recrystallized twice from 2-propanol to give the title salt (4.713 g), $[\alpha]_D$=+56 (MeOH, c=0.20).

The combined mother liquors from above were concentrated and the residue was taken up in water, acidified with 2M hydrochloric acid and extracted twice with methylene chloride. The organic layers were each washed with brine, dried over sodium sulfate, combined and concentrated in vacuo. The residue was taken up in 2-propanol (400 mL), warmed to 80° C. and treated with (R)-(+)-α-methylbenzylamine (9.1 mL, 70 mmol). The mixture was stirred while allowed to cool to rt over 16 h and was then cooled to −10° C. for 1 h. The salt was filtered, washed with a small amount of ether to remove 2-propanol and air dried to give 8.22 g of salt. This was recrystallized from 2-propanol to give the title salt (6.31 g), $[\alpha]_D$=55 (MeOH, c=0.21).

Step C: (+)-trans-4-Methylene-2-phenylcyclopentanoic acid and (−)-trans-4-methylene-2-phenylcyclopentanoic acid Method A The (+)-trans-4-methylene-2-phenylcyclopentanoic acid, (S)-(−)-α-methylbenzylamine salt from Step B (4.7 g) was suspended in methylene chloride and water and acidified with 2M hydrochloric acid and extracted twice with methylene chloride. The organic layers were each washed with brine, dried over sodium sulfate, combined and concentrated in vacuo to give the title (+) acid (3.1 g), $[\alpha]_D$=+101 (MeOH, c=0.135).

Similarly, the (−)-trans4-methylene-2-phenylcyclopentanoic acid, (R)-(+)-α-methylbenzylamine salt (6.3 g) was converted to the free (−)-title acid (4.23 g), $[\alpha]_D$=−103 (MeOH, c=0.23).

Method B

Step B1: 1-(S)-(((S)-(−)-4-Benzyl-2-oxazolidin-1-yl)carbonyl)-3-methylene-2-(S)-phenylcyclopentane (higher $R_f$) and 1-(R)-(((S)-(−)4-benzyl-2-oxazolidin-1-yl)carbonyl)-3-methylene-2-(R)-phenylcyclopentane (lower $R_f$)

A solution of (+−)-trans4-methylene-2-phenylcyclopentanoic acid (47.5 g, 235 mmol) in ether (1 L) and TEA (36 mL, 260 mmol) was cooled to −10° C. Trimethylacetyl chloride (31.8 mL, 260 mmol) was then added slowly and after stirring at −10° C. for 10 min, the reaction was allowed to warm to 10° C. over 1 h. The reaction was then recooled to −60° C.

To the above solution at −60° C. was added via a canula a solution of (S)-(−)-4-benzyl-2-oxazolidinone (45.8 g, 260 mmol) in THF (500 mL) which had been treated at −50° C. with 2.5 M n-butyl lithium (103 nL, 257 mmol) and aged at −50° C. for 45 min. The reaction was allowed to warm to rt over 16 h. The reaction was diluted with ether (1 L) and quenched with sat'd aqueous ammonium chloride (1 L). The layers were separated and the aqueous layer was reextracted with a second portion of ether. The organic layers were each washed twice with 2N hydrochloric acid, twice with 1N sodium hydroxide and brine, dried over sodium sulfate, combined and concentrated. The residue was purified by chromatography (20% ethyl acetate in hexanes) to give the two diastereomeric products, higher $R_f$ (18.4 g) and lower $R_f$ (17.7 g).

Step B2: (+)-trans-4-Methylene-2-phenylcyclopentanoic acid

A solution of 1-(S)-(((S)-(−)-4-benzyl-2-oxazolidin-1-yl)carbonyl)-3-methylene-2-(S)-phenylcyclopentane (higher $R_f$ product from Step B 1) (20.9 g, 58 mmol) in a 3:1 mixture of THF: water (1 L) was cooled to 5° C. Hydrogen peroxide (30%, 39.5 mL, 350 mmol) and lithium hydroxide (4.85 g, 106 mmol) were added and the reaction was stirred for 3.5 h. The excess peroxide was quenched by dropwise addition of sodium sulfite (60 g) in water (1 L) over 1.5 h while maintaining the temperature below 5° C. After stirring for 2 additional hours, most of the THF was removed in vacuo and the aqueous layer was washed 3 times with methylene chloride. The aqueous layer was acidified to pH=2 with conc. HCl and reextracted twice with methylene chloride. The organic layers were washed with brine, dried and concentrated to give the (+) title product, $[\alpha]_D$=+100.5 (MeOH, c=0.207).

Step D: (+)-trans-1-Hydroxymethyl-4-methylene-2-phenylcyclopentane and (−)-trans-1-hydroxymethyl4-methylene-2-phenylcyclopentane Method A A solution of (+)-trans-4-methylene-2-phenylcyclopentanoic acid from Step C (4.15 g, 20.5 mmol) in THF (100 mL) under nitrogen was cooled to −7° C. and 1M LAH in THF (31 mL, 31 mmol) was added dropwise over 15. The reaction was allowed to warm to rt over 16 h. The excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title (+) product (3.93 g), $[\alpha]_D$=+50 (MeOH, c=0.20).

Similarly, the (−)-trans-4-methylene-2-phenylcyclopentanoic acid from Step C (4.23 g) was converted to the title (−) alcohol (3.75 g), $[\alpha]_D$=−51 (MeOH, c=0.2).

Method B

Prep-HPLC of (+−)-trans-4-methylene-2-phenylcyclopentanoic from Example 1, Step B using a Chiracel OD column (5–10% isopropanol in hexanes) affords good separation of the title (−) enantiomer as the first eluting band and the (+) enantiomer as the second eluting band.

Step E: (+)-trans-1-t-Butyldimethylsilyloxymethyl-4-methylene-2-phenylcyclopentane and (−)-trans-1-t-butyldimethylsilyloxymethyl-4-methylene-2-phenylcyclopentane To a solution of (+)-trans-1-hydroxymethyl4-methylene-2-phenylcyclopentane from Step D (3.9 g, 21 mmol) in methylene chloride (50 mL) was added t-butyldimethylsilyl chloride (4.7 g, 31 mmol) and DIPEA (7.3 mL, 42 mmol). The reaction was stirred at rt for 16 h, poured into dilute aq. HCl and extracted twice with ether. The organic layers were washed with brine, dried over sodium sulfate, combined and concentrated. The residue was purified by FC (100% hexanes) to afford the title product (5.6 g) as a oil, $[\alpha]_D$=+42.3 (MeOH, c=0.18).

Similarly, (−)-trans-1-hydroxymethyl-4methylene-2-phenylcyclopentane from Step D (3.75 g) was converted to the title (−) silylether (5.5 g), $[\alpha]_D$=−44.4 (MeOH, c=0.18).

Step F: (+)-trans-1-Hydroxymethyl-4-oxo-2-phenylcyclopentane and (−)-trans-1-hydroxymethyl-4-oxo-2-phenylcyclopentane Method A A solution of (+)-trans-1-t-butyldimethylsilyloxymethyl-4-methylene-2-phenylcyclopentane from Step E (4.6 g, 15 mmol) in methanol (100 mL) was cooled to −70° C. in a dry-ice acetone bath and ozone was bubbled through until a blue color persisted which was discharged with a stream of nitrogen. Dimethylsulfide (10 mL) was added and after 15 min, the reaction was allowed to warm to rt over 16 h. Since by TLC (20% ethyl acetate in hexanes) indicated that there was significant loss of the silyl as well as dimethylketal formation, the methanol was mostly remove in vacuo. The residue was diluted with water and treated with sulfuric acid (6 mL) and stirred for 2 h. The mixture was extracted twice with ethyl acetate and the organic layers were washed with brine (containing some sodium bicarbonate), dried over sodium sulfate, combined and concentrated. The residue was purified by FC (15–30% ethyl acetate in hexanes) to give the (+) title ketone/alcohol (2.87 g), $[\alpha]_D$=−96 (MeOH, c=0.2).

Similarly, (−)-trans-1-t-butyldimethylsilyloxymethyl-4-methylene-2-phenylcyclopentane from Step E (4.4 g) was converted to the title (−) ketone/alcohol (2.8 g), $[\alpha]_D$=+97 (MeOH, c=0.2).

Method B

The title compounds can also be obtained directly from (+)-trans-1-hydroxymethyl-4-methylene-2-phenylcyclopentane and (−)-1-hydroxymethyl-4-methylene-2-phenylcyclopentane by ozonolysis as above. Thus, (+)-trans-1-hydroxymethyl-4-methylene-2-phenylcycclopentane (3.7 gm, 20 mmol) afforded from (+)-trans-1-hydroxymethyl-4-oxo-2-phenylcyclopentane (3.5 g).

Step G: 1-(S)-Benzylamino-3-(S)-hydroxymethyl-4-(S)-phenylcyclopentane and 1-(R)-benzylamino-3-(S)-hydroxymethyl-4-(S)-phenylcyclopentane To a solution of (+)-trans-1-hydroxymethyl4-oxo-2-phenylcyclopentane from Step F (1.19 g, 6.3 mmol) in 1,2-dichloroethane (25 mL) was added benzylamine (1.3 mL, 12 mmol) and acetic acid (0.75 mL, 13 mmol). After 10 min, sodium triacetoxyborohydride (2.65 g, 12.5 mmol) was added in portions and the reaction was stirred at rt for 16 hr. The reaction was quenched into dilute aq. sodium carbonate and the mixture was extracted twice with ethyl acetate. The organic layers were washed with brine, dried over sodium sulfate, combined and concentrated. The residue was purified by FC (5–10% methanol in methylene chloride) to separate the title products (1.6 g) as a mixture of C-1isomers.

Step H: 1-(S)-t-Butoxycarbonylamino-3-(S)-hydroxymethyl-4-(S)-phenylcyclopentane (Higher $R_f$ isomer) and 1-(R)-t-butoxycarbonylamino-3-(S)-hydroxymethyl-4-(S)-phenylcyclopentane (Lower $R_f$ isomer)

To a solution of 1-(S)-benzylamino-3-(S)-hydroxymethyl-4-(S)-phenylcyclopentane and 1-(R)-benzylamino-3-(S)-hydroxymethyl-4-(S)-phenylcyclopentane from Step G (1.6 g, 5.6 mmol) in methanol (40 mL) was added 20% palladium hydroxide (300 mg, 50% by wt water) and ammonium formate (7.0 g, 111 mmol). The reaction was heated at 60° C. for 6 h and rt for 16 h. The reaction was filtered and concentrated. The residue was taken up in water and the aqueous layer was made basic with 2N sodium hydroxide and extracted twice with methylene chloride. The organic layers were washed with brine, dried over sodium sulfate, combined and concentrated to afford crude amino-alcohol.

The above product was taken up in methylene chloride (25 mL), cooled in an ice bath and DIPEA (2.9 mL, 17 mmol) and di-t-butyl dicarbonate (1.28 g, 5.8 mmol) were added. After 16 h, the reaction was poured into dilute aq. HCl and extracted twice with methylene chloride. The organic layers were washed with brine, dried over sodium sulfate, combined and concentrated. The residue was purified by FC (30–40% ethyl acetate in hexanes) to afford separation of the two title compounds.

Higher $R_f$:

NMR (CDCl$_3$) δ: 1.43 (s, 9H), 1.45 (m, 1H), 1.9–2.1 (m, 2H), 2.17 (m, 1H), 2.40 (m, 1H), 3.01 (q, 1H), 3.59 (dABq, 2H), 4.20 (br m, 1H), 5.00 (br s, 1H), 17.15–7.3 (m, 5H).

Lower $R_f$:

NMR (CDCl$_3$) δ: 1.43 (s, 9H), 1.58 (ddd, 1H), 1.78.1 (ddd, 1H), 2.02 (m, 1H), 2.29 (m, 1H), 2.47 (ddd, 1H), 2.76 (ddd, 1H), 3.54 (dABq, 2H), 4.06 (br m, 1H) 4.62 (br s, 1H), 7.15–7.3 (m, 5H).

Step I: 1-(S)-t-Butoxycarbonylamino-3-(S)-formyl-4-(S)-phenylcyclopentane (Higher $R_f$ isomer) and 1-(R)-t-butoxycarbonylamino-3-(S)-formyl-4-(S)-phenylcyclopentane (Lower $R_f$ isomer)

To a solution of oxalyl chloride (0.145 mL, 1.67 mmol) in methylene chloride (10 mL) at −70° C. was added dropwise DMSO (0.24 mL, 3.3 mmol). After 15 min, a solution of 1-(S)-t-butoxycarbonylamino-3-(S)-hydroxymethyl-4-(S)-phenylcyclopentane (Higher $R_f$ isomer from Step F) (194 mg, 0.66 mmol) in methylene chloride (5 mL) was added. The reaction was stirred at −70° C. for 1.5 h and then DIPEA (1.2 mL, 6.6 mmol) in methylene chloride (5 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (15% ethyl acetate in hexanes) to give the title product (155 mg) after vacuum drying.

Using essentially the same procedure as above, material derived from the lower isomer from Step H (0.189 g, 0.6 mmol) was also converted to the lower $R_f$ title compound (175 mg).

Step J: 1-(S)-(t-Butoxycarbonylamino)-3-(S)-((4-(N-(4-nitrobenzyloxycarbonyl)-N-(allyl)amino)piperidin-1-yl)methyl)-4-(S)-phenylcyclopentane (Higher $R_f$ isomer) and 1-(R)-(t-butoxycarbonylamino)-3-(S)-((4-(N-(4-nitrobenzyloxycarbonyl)-N-(allyl)amino)piperidin-1-yl)methyl)-4-(S)-phenylcyclopentane (Lower $R_f$ isomer)

To a solution of 1-((S)-(t-butoxycarbonylamino)-3-(S)-(formyl)-4-(S)-phenylcyclopentane (from Step I, derived from Higher $R_f$ isomer in Step G) (155 mg, 0.54 mmol) in 1,2-dichloroethane (5 mL) was added 4-(N-(4-nitrobenzyloxycarbonyl)(N-allyl)amino)piperidine hydrochloride (210 mg, 0.59 mmol) and DIPEA (0.12 mL, 0.64 mmol). After 15 min, sodium triacetoxyborohydride (230 mg, 1.1 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 5% methanol in methylene chloride to give the title product (280 mg) as the free amine.

MS (NH$_3$/ESI): m/z 593 (M+1).

Using essentially the same procedure as above, material derived from the lower isomer from Step H–I (0.175 g, 0.6 mmol) was also converted to the lower $R_f$ title compound (275 mg).

Step K: 1-(S)-(Amino)-3-(S)-((4-(N-(4-nitrobenzyloxycarbonyl)-N-(allyl)amino)piperidin-1-yl)methyl)4-(S)-phenylcyclopentane di-hydrochloride salt (Higher $R_f$ isomer) and 1-(R)-(amino)-3-(S)-((4-(N-(4-nitrobenzyloxycarbonyl)-N-(allyl)amino)piperidin-1-yl)methyl)-4-(S)-phenylcyclopentane di-hydrochloride salt (Lower $R_f$ isomer)

A solution of hydrogen chloride (4.6 mmol) in methanol was prepared by addition of acetyl chloride (0.325 mL, 4.6 mmol) to methanol (10 mL) and aging for 15 min. To this was added 1-(S)-(t-butoxycarbonylamino)-3-(S)-((4-(N-(4-nitrobenzyloxycarbonyl)-N-(allyl)amino)piperidin-1-yl)methyl)-4-(S)-phenylcyclopentane (Higher $R_f$ isomer from Step J) (270 mg, 0.46 mmol). After 16 h, the volatiles were removed in vacuo to dryness to give the title compound as the di-hydrochloride salt (248 mg).

Using essentially the same procedure as above, material derived from the lower isomer from Step H–J (0.250 g, 0.42 mmol) was also converted to the lower $R_f$ title compound (235 mg).

Step L: N-(1-(S)-3-(S)-((4-(N-(4-Nitrobenzyloxycarbonyl)-N-(allyl)amino)piperidin-1-yl)methyl)-4-(S)-phenylcyclopent-1-yl)-L-leucine (Isomer 6B) and N-(1-(S)-3-(S)-((4-(N-(4-nitrobenzyloxycarbonyl)-N-(allyl)amino)piperidin-1-yl)methyl)4-(S)-phenylcyclopent-1-yl)-D-leucine (Isomer 7H) di-TFA salts To a solution of 1-(S)-(amino)-3-(S)-((4-(N-(4-nitrobenzyloxycarbonyl)-N-(allyl)amino)piperidin-1-yl)methyl)4-(S)-phenylcyclopentane di-hydrochloride salt (derived from the higher $R_f$ isomer in Steps H–K) (20 mg, 0.045 mmol), 4-methyl-2-oxo-valeric acid (15 mg, 0.11 mmol) and DIPEA (0.016 mL, 0.09 mmol) in 1,2-dichloroethane (2 mL) was added sodium triacetoxyborohydride (29 mg, 0.135 mmol). The reaction was stirred at 50° C. for 10 h and then at rt for another 16 h. It was then quenched with aq sodium carbonate and extracted three times with ethyl acetate. The organic layers were each washed with brine, dried over sodium sulfate, combined and concentrated in vacuo. The residue was purified by Prep TLC eluting with 10% methanol in methylene chloride to give the title products (8 mg) as a mixture of the free amines. HPLC analysis as in Example 6 and 7 gave only a single band corresponding to Isomers B (and enantiomeric Isomer F) and H (and enantiomeric Isomer D) which co-elute.

HPLC/MS (ESI): m/z 593 (M+1).

EXAMPLE 9

N-(1-(R)-3-(S)-((4-(N-(4-Nitrobenzyloxycarbonyl)-N-(allyl)amino)piperidin-1-yl)methyl)-4-(S)-phenylcyclopent-1-yl)-L-leucine (Isomer 7E) and N-(1-(R)-3-(S)-((4-(N-(4-nitrobenzyloxycarbonyl)-N-(allyl)amino)piperidin-1-yl)methyl)-4-(S)-phenylcyclopent-1-yl)-D-leucine (Isomer 6C) di-TFA salts Using essentially the same procedure as in Example 8, Step L, but substituting 1-(R)-(amino)-3-(S)-((4-(N-(4-nitrobenzyloxycarbonyl)-N-(allyl)amino)piperidin-1-yl)methyl)-4-(S)-phenylcyclopentane di-hydrochloride salt (derived from the lower $R_f$ isomer in Steps H–K) (20 mg, 0.045 mmol), the two title compounds were prepared. HPLC analysis of the crude products as in Example 6 and 7 indicated two peaks. In this case the diastereomers were separable on Prep TLC (10% methanol in methylene chloride). HPLC analysis as in Example 6 and 7 now gave only a single peak for each sample from the Prep TLC. The higher band corresponded to Isomer E (and enantiomeric Isomer A) and the lower band corresponded to Isomer C (and enantiomeric Isomer G) which are distinct in the HPLC. The di-TFA salts were prepared by evaporation from 0.5% TFA in acetonitrile.

Higher Isomer E: HPLC/MS (ESI): m/z 593 (M+1).

Lower Isomer C: HPLC/MS (ESI): m/z 593 (M+1).

EXAMPLE 10

Using essentially the same procedure as in Example 6, Steps F and G, but substituting L-valine t-butyl ester hydrochloride in Step F, the following diastereomers were obtained after a combination of Prep TLC and HPLC separation.

N-(1-(S)-3-(R)-((4-(N-(4-Nitrobenzyloxycarbonyl)-N-(allyl)amino)piperidin-1-yl)methyl)-4-(R)- phenylcyclopent-1-yl)-L-valine di-TFA salt (Isomer A), HPLC/MS (ESI): m/z 579 (M+1).

N-(1-(S)-3-(S)-((4-(N-(4-nitrobenzyloxycarbonyl)-N-(allyl) amino)piperidin-1-yl)methyl)-4-(S)-phenylcyclopent-1-yl)-L-valine di-TFA salt (Isomer B), HPLC/MS (ESI): m/z 579 (M+1).

N-(1-(R)-3-(S)-((4-(N-(4-nitrobenzyloxycarbonyl)-N-(allyl)amino)piperidin-1-yl)methyl)-4-(S)-phenylcyclopent-1-yl)-L-valine di-TFA salt (Isomer C) HPLC/MS (ESI): m/z 579 (M+1).

N-(1(R)-3-(R)-((4-(N-(4-nitrobenzyloxycarbonyl)-N-(allyl) amino)piperidin-1-yl)methyl)-4-(R)-phenylcyclopent-1-yl)-L-valine di-TFA salt (Isomer D) HPLC/MS (ESI): m/z 579 (M+1).

EXAMPLE 11

Using essentially the same procedure as in Example 6, Steps F and G, but substituting L-isoleucine t-butyl ester hydrochloride in Step F, the following diastereomers were obtained after a combination of Prep TLC and BPLC separation.

N-(1-(S)-3-(R)-((4-(N-(4-Nitrobenzyloxycarbonyl)-N-(allyl)amino)piperidin-1-yl)methyl)-4-(R)-phenylcyclopent-1-yl)-L-isoleucine di-TFA salt (Isomer A), HPLC/MS (ESI): m/z 593 (M+1).

N-(1-(S)-3-(S)-((4-(N-(4-nitrobenzyloxycarbonyl)-N-(allyl) amino)piperidin-1-yl)methyl)-4-(S)-phenylcyclopent-1-yl)-L-isoleucine di-TFA salt (Isomer B), HPLC/MS (ESI): m/z 593 (M+1).

N-(1-(R)-3-(S)-((4-(N-(4-nitrobenzyloxycarbonyl)-N-(allyl)amino)piperidin-1-yl)methyl)4-(S)-phenylcyclopent-1-yl)-L-isoleucine di-TFA salt (Isomer C) HPLC/MS (ESI): m/z 593 (M+1).

N-(1-(R)-3-(R)-((4-(N-(4-nitrobenzyloxycarbonyl)-N-(allyl)amino)piperidin-1-yl)methyl)-4-(R)-phenylcyclopent-1-yl)-L-isoleucine di-TFA salt (Isomer D) HPLC/MS (ESI): m/z 593 (M+1).

EXAMPLE 12

Using essentially the same procedure as in Example 6, Steps F and G, but substituting L-phenylglycine t-butyl ester hydrochloride in Step F, the following diastereomers were obtained after a combination of Prep TLC and HPLC separation.

N-(1-(S)-3-(R)-((4-(N-(4-Nitrobenzyloxycarbonyl)-N-(allyl)amino)piperidin-1-yl)methyl)-4-(R)-phenylcyclopent-1yl)-L-phenyglycine di-TFA salt (Isomer A), HPLC/MS (ESI): m/z 627 (M+1).

N-(1-(S)-3-(S)-((4-(N-(4-nitrobenzyloxycarbonyl)-N-(allyl) amino)piperidin-1-yl)methyl)4-(S)-phenylcyclopent-1-yl)-L-phenylglycine di-TFA salt (Isomer B), HPLC/MS (ESI): m/z 627 (M+1).

N-(1-(R)-3-(S )-((4-(N-(4-nitrobenzyloxycarbonyl)-N-(allyl)amino)piperidin-1-yl)methyl)-4-(S)-phenylcyclopent-1-yl)-L-phenylglycine di-TFA salt (Isomer C) HPLC/MS (ESI): m/z 627 (M+1).

N-(1-(R)-3-(R)-((4-(N-(4-nitrobenzyloxycarbonyl)-N-(allyl)amino)piperidin-1-yl)methyl)-4-(R)-phenylcyclopent-1-yl)-L-phenylglycine di-TFA salt (Isomer D) HPLC/MS (ESI): m/z 627 (M+1).

EXAMPLE 13

Using essentially the same procedure as in Example 6, Steps F and G, but substituting L-cyclohexylglycine t-butyl ester hydrochloride in Step F, the following diastereomers were obtained after a combination of Prep TLC and HPLC separation.

N-(1-(S)-3-(R)-((4-(N-(4-Nitrobenzyloxycarbonyl)-N-(allyl)amino)piperidin-1-yl)methyl)-4-(R)-phenylcyclopent-1-yl)-L-cyclohexylglycine di-TFA salt (Isomer A), HPLC/MS (ESI): m/z 633 (M+1).

N-(1-(S)-3-(S)-((4-(N-(4-nitrobenzyloxycarbonyl)-N-(allyl) amino)piperidin-1-yl)methyl)-4-(S)-phenylcyclopent-1-yl)-L-cyclohexylglycine di-TFA salt (Isomer B), HPLC/MS (ESI): m/z 633 (M+1).

N-(1-(R)-3-(S)-((4-(N-(4-nitrobenzyloxycarbonyl)-N-(allyl)amino)piperidin-1-yl)methyl)4-(S)-phenylcyclopent-1-yl)-L-cyclohexylglycine di-TFA salt (Isomer C) HPLC/MS (ESI): m/z 633 (M+1).

N-(1-(R)-3 -(R)-((4-(N-(4-nitrobenzyloxycarbonyl)-N-(allyl)amino)p peridin-1-yl)methyl)-4-(R)-phenylcyclopent-1-yl)-L-cyclohexylglycine di-TFA salt (Isomer D) HPLC/MS (ESI): m/z 633 (M+1).

EXAMPLE 14

Using essentially the same procedures as in Example 6, Steps E, F and G, but substituting 4-(N-(4-nitrobenzylaminocarbonyl)(N-ethyl)amino)piperidine hydrochloride in Step E and L-cyclohexylglycine t-butyl ester hydrochloride in Step F and TFA in place of HCl in ether in Step G, the following diastereomers were obtained after a combination of Prep TLC and HPLC separation. The relative TLC and HPLC retention times of these ureas was the same as the above carbamates.

N-(1-(S)-3-(R)-((4-(N-(4-Nitrobenzylaminocarbonyl)-N-(ethyl) amino)piperidin-1-yl)methyl)-4-(R)-phenylcyclopent-1-yl)-L-cyclohexylglycine di-TFA salt (Isomer A), HPLC/MS (ESI): m/z 620 (M+1).

N-(1-(S)-3-(S)-((4-(N-(4-nitrobenzylaminocarbonyl)-N-(ethyl)amino)piperidin-1-yl)methyl)-4-(S)-phenylcyclopent-1-yl)-L-cyclohexylglycine di-TFA salt (Isomer B), HPLC/MS (ESI): m/z 620 (M+1).

N-(1-(R)-3-(S)-((4-(N-(4-nitrobenzylaminocarbonyl)-N-(ethyl)amino)piperidin-1-yl)methyl)-4-(S)-phenylcyclopent-1-yl)-L-cyclohexylglycine di-TFA salt (Isomer C) HPLC/MS (ESI): m/z 620 (M+1).

N-(1-(R)-3-(R)-((4-(N-(4-nitrobenzylaminocarbonyl)-N-(ethyl)amino)piperidin-1-yl)methyl)-4-(R)-phenylcyclopent-1-yl)-L-cyclohexylglycine di-TFA salt (Isomer D) HPLC/MS (ESI): m/z 620 (M+1).

EXAMPLE 15

Using essentially the same procedures as in Example 6, Steps E, F and G, but substituting 4-(N-(4-nitrobenzylaminocarbonyl)(N-methyl)amino)piperidine hydrochloride in Step E and L-cyclohexylglycine t-butyl ester hydrochloride in Step F and TFA in place of HCl in ether in Step G, the following diastereomers were obtained after a combination of Prep TLC and HPLC separation. The relative TLC and HPLC retention times of these ureas was the same as the above carbamates.

N-(1-(S)-3-(R)-((4-(N-(4-Nitrobenzylaminocarbonyl)-N-(methyl)amino)piperidin-1-yl)methyl)-4-(R)-phenylcyclopent-1-yl)-L-cyclohexylglycine di-TFA salt (Isomer A), HPLC/MS (ESI): m/z 606 (M+1).

N-(1-(S)-3-(S)-((4-(N-(4-nitrobenzylaminocarbonyl)-N-(methyl)amino)piperidin-1-yl)methyl)4-(S)-phenylcyclopent-1-yl)-L-cyclohexylglycine di-TFA salt (Isomer B), HPLC/MS (ESI): m/z 606 (M+1).

N-(1-(R)-3-(S)-((4-(N-(4-nitrobenzylaminocarbonyl)-N-(methyl)amino)piperidin-1-yl)methyl)-4-(S)-phenylcyclopent-1-yl)-L-cyclohexylglycine di-TFA salt (Isomer C) HPLC/MS (ESI): m/z 606 (M+1).

N-(1-(R)-3-(R)-((4-(N-(4-nitrobenzylaminocarbonyl)-N-(methyl)amino)piperidin-1-yl)methyl)-4-(R)-phenylcyclopent-1-yl)-L-cyclohexylglycine di-TFA salt (Isomer D) HPLC/MS (ESI): m/z 606 (M+1).

EXAMPLE 16

N-(1-(R)-3-(S)-((4-(N-(4-Trifluoromethylbenzyloxycarbonyl)-N-(prop-1-yl)amino)piperidin-1-yl)methyl)-4-(S)-phenylcyclopent-1-yl)-D-leucine di-TFA salt and N-(1-(S)-3-(S)-((4-(N-(4-trifluoromethylbenzyloxycarbonyl)-N-(prop-1-yl)amino)piperidin-1-yl)methyl)4-(S)-phenylcyclopent-1-yl)-D-leucine di-TFA salt Step A: (1-(R)-3-(S)-(Hydroxymethyl)-4-(S)-phenylcyclopent-1-yl)-D-leucine (Higher $R_f$) and (1-(S)-3-(S)-(hydroxymethyl)-4-(S)-phenylcyclopent-1-yl)-D-leucine (lower $R_f$)
Method A To a solution of (+)-trans-1-hydroxymethyl-4-oxo-2-phenylcyclopentane from Example 8, Step F (250 mg, 1.32 mmol), D-leucine t-butyl ester hydrochloride (370 mg, 2.0 mmol) and DIPEA (0.36 mL, 2.0 mmol) in 1,2-dichloroethane (10 mL) was added sodium triacetoxyborohydride (840 mg, 4.0 mmol). The reaction was stirred at rt for 4 h and was then quenched with aq sodium carbonate and extracted three times with ethyl acetate. The organic layers were each washed with brine, dried over sodium sulfate, combined and concentrated in vacuo. The residue was purified by FC eluting with a gradient of 5–25% ethyl acetate in hexanes to give the higher $R_f$ 1-(R) title compound as the major product (280 mg) and the lower $R_f$ 1-(S) as the minor product (160 mg mixed fractions).
Method B To a solution of (+–)-trans-1-hydroxymethyl-4-oxo-2-phenylcyclopentane from Example 8, Step F (3.3 g, 16 mmol) in methylene chloride (100 mL) was added t-butyldimethylsilyl chloride (11 g, 49 mmol) and DIPEA (22 mL, 74 mmol). The reaction was stirred at rt for 16 h, poured into dilute aq. HCl and extracted twice with ether. The organic layers were washed with brine, dried over sodium sulfate, combined and concentrated. The residue was purified by FC (5% ethyl acetate in hexanes) to afford of (+)-trans-1-t-butyldimethylsilyloxymethyl-4-oxo-2-phenylcyclopentane (6.3 g) as a oil, $[\alpha]_D$=+97 (MeOH, c=0.2).

To a solution of (+)-trans-1-t-butyldimethylsilyloxymethyl-4-oxo-2-phenylcyclopentane from above (1.0 g, 3.28 mmol), D-leucine t-butyl ester hydrochloride (2,2 g, 3.0 mmol) and DIPEA (1.8 mL, 10.2 mmol) in 1,2-dichloroethane (20 mL) was added sodium triacetoxyborohydride (2.1 g, 10 mmol). The reaction was stirred at rt for 5 h and was then quenched with aq sodium carbonate and extracted three times with ethyl acetate. The organic layers were each washed with brine, dried over sodium sulfate, combined and concentrated in vacuo. The residue was purified by FC eluting with 5% ethyl acetate in hexanes to give the higher $R_f$ 1-(R) title compound as the minor product and the lower $R_f$ 1-(S) as the major product (1.35 g as a mixture).

To a solution of the above product (1.35 g, 2.85 mmol) in THF (10 mL) was 1M TBAF in THF (4.3 mL, 4.3 mmol). The reaction was stirred at rt for 16 h and the concentrated. The residue was purified by FC eluting with 20–25% ethyl acetate in hexanes to give the higher $R_f$ 1-(R) title compound as the minor product (33 mg pure) and the lower $R_f$ 1-(S) as the major product (202 mg pure, 0.70 g as a mixture).

Step B: (1-(R)-3-(S)-(Formyl)-4-(S)-phenylcyclopent-1-yl)-D-leucine (Higher $R_f$) and (1-(S)-3-(S)-(formyl)-4-(S)-phenylcyclopent-1-yl)-D-leucine (lower $R_f$)
Method A To a solution of oxalyl chloride (0.100 mL, 1.1 mmol) in methylene chloride (20 mL) at –70° C. was added dropwise DMSO (2.2 mL, 5.0 mmol). After 15 min, a solution of (1-(R)-3-(S)-(hydroxymethyl)-4-(S)-phenylcyclopent-1-yl)-D-leucine (Higher $R_f$ from Step A, Method A) (160 mg, 0.44 mmol) containing 1 eq. of 1M HCl in ether in methylene chloride (5 mL) was added. The reaction was stirred at –70° C. for 1.5 h and then DIPEA (0.77 mL, 4.5 mmol) in methylene chloride (5 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (20% ethyl acetate in hexanes) to give the higher $R_f$ title product (38 mg) after vacuum drying.
Method B To a solution of (1-(R)-3-(S)-(hydroxymethyl)-4-(S)-phenylcyclopent-1-yl)-D-leucine (mixture of higher and lower $R_f$ from Step A, Method A) (142 mg, 0.39 mmol) in methylene chloride (10 mL) was added TPAP (6.9 mg, 0.020 mmol) and N-methylmorholine (70 mg, 0.60 mmol). The reaction was stirred under nitrogen at rt for 1 h and was then concentrated. The residue was purified by FC (25% ethyl acetate in hexanes) to give the title products (108 mg) after vacuum drying.

Step C: N-(1-(R)-3-(S)-((4-(N-(4-Trifluoromethylbenzyloxycarbonyl)-N-(prop-1-yl)amino)piperidin-1-yl)methyl)-4-(S)-phenylcyclopent-1-yl)-D-leucine t-butyl ester (higher $R_f$) and N-(1-(S)-3-(S)-((4-(N-(4-trifluoromethylbenzyloxycarbonyl)-N-(prop-1-yl)amino)piperidin-1-yl)methyl)-4-(S)-phenylcyclopent-1-yl)-D-leucine t-butyl ester (lower $R_f$)

To a solution of (1-(R)-3-(S)-(formyl)4-(S)-phenylcyclopent-1-yl)-D-leucine (higher $R_f$) and (1-(S)-3-(S)-(formyl)-4-(S)-phenylcyclopent-1-yl)-D-leucine (lower $R_f$) (from Step B, Method B) (9 mg, 0.025 mmol) in 1,2-dichloroethane (1 mL) was added 4-N-(4-trifluoromethylbenzyloxycarbonyl)-N-(prop-1-yl)amino)piperidine hydrochloride (12 mg, 0.032 mmol) and DIPEA (0.006 mL, 0.033 mmol). After 15 min, sodium triacetoxyborohydride (11 mg, 0.051 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 60% ethyl acetate in hexanes to give the title products (4 mg and 6 mg) as the free amines. (Each isomer): HPLC/MS (ES): m/z 688 (M+1).

Step D: N-(1-(R)-3-(S)-((4-(N-(4-Trifluoromethylbenzyloxycarbonyl)-N-(prop-1-yl)amino)piperidin- 1-yl)methyl)-4-(S)-phenylcyclopent-1-yl)-D-leucine di-TFA salt (derived from higher $R_f$) and N-(1-(S)-3-(S)-((4-(N-(4-trifluoromethylbenzyloxycarbonyl)-N-(prop-1-yl)amino)piperidin-1-yl)methyl)-4-(S)-phenylcyclopent- 1-yl)-D-leucine di-TFA salt (derived from lower $R_f$)

Each the products from Step C were taken up in TFA (5 mL) and aged at rt for 16 h. The volatiles were removed under a stream of nitrogen to afford the title products as the di-TFA salts.

HPLC/MS (ES): m/z 632 (M+1).

EXAMPLE 17

N-(1-(R)-3-(S)-((4-(N-(4-Methylbenzyloxycarbonyl)-N-(prop-1-yl)amino)piperidin-1-yl)methyl)-4-(S)-phenylcyclopent-1-yl)-D-leucine di-TFA salt and N-(1-(S)-3-(S)-((4-(N-(4-methylbenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(4-methylbenzyloxycarbonyl)-N-(prop-1-yl)amino)piperidine hydrochloride in Step C, the two diastereomeric title compounds were prepared.

(Each isomer): HPLC/MS (ESI): m/z 578 (M+1).

EXAMPLE 18

N-(1-(R)-3-(S)-((4-(N-(2-Fluorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(2-fluorobenzyloxycarbonyl)-N-(prop-1-yl)amino)piperidine hydrochloride in Step C, the title compound was prepared.

HPLC/MS (ESI): m/z 582 (M+1).

EXAMPLE 19

N-(1-(R)-3-(S)-((4-(N-(3-Fluorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(3-fluorobenzyloxycarbonyl)-N-(prop-1-yl)amino)piperidine hydrochloride in Step C, the compound was prepared.

HPLC/MS (ESI): m/z 582 (M+1).

EXAMPLE 20

N-(1-(R)-3-(S)-((4-(N-(4-Fluorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(4-fluorobenzyloxycarbonyl)-N-(prop-1-yl)amino)piperidine hydrochloride in Step C, the title compound was prepared.

HPLC/MS (ESI): m/z 582 (M+1).

EXAMPLE 21

N-(1-(R)-3-(S)-((4-(N-(3,4-Difluorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(3,4-di-fluorobenzyloxycarbonyl)-N-(prop-1-yl)amino)piperidine hydrochloride in Step C, the title compound was prepared.

HPLC/MS (ESI): m/z 600 (M+1).

EXAMPLE 22

N-(1-(R)-3-(S)-((4-(N-(3,5-Difluorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(3,5-di-fluorobenzyloxycarbonyl)-N-(prop-1-yl)amino)piperidine hydrochloride in Step C, the title compound was prepared.

HPLC/MS (ESI): m/z 600 (M+1).

EXAMPLE 23

N-(1-(R)-3-(S)-((4-(N-(2,4-Difluorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(2,4-di-fluorobenzyloxycarbonyl)-N-(prop-1-yl)amino)piperidine hydrochloride in Step C, the title compound was prepared.

HPLC/MS (ESI): m/z 600 (M+1).

EXAMPLE 24

N-(1-(R)-3-(S)-((4-(N-(4-Chlorobenzyloxycarbonyl)-N-(prop-1-yl)amino)piperidin-1-yl)methyl)-4-(S)-phenylcyclopent-1-yl)-D-leucine di-TFA salt Using essentially the same procedures as in Example 16, Step C and D, but substituting 4-(N-(4-chlorobenzyloxycarbonyl)-N-(prop-1-yl)amino)piperidine hydrochloride in Step C, the title compound was prepared.

HPLC/MS (ESI): m/z 598 (M+1).

EXAMPLE 25

N-(1-(R)-3-(S)-((4-(N-(4-Fluorobenzyloxycarbonyl)-N-(prop-1-yl)amino)piperidin-1-yl)methyl)4-(S)-phenylcyclopent-1-yl)-D-cyclobutylalanine di-TFA salt, N-(1-(R)-3-(S)-((4-(N-(4-fluorobenzyloxycarbonyl)-N-(prop-1-yl)amino)piperidin-1-yl)methyl)4-(S)-phenylcyclopent-1-yl)-L-cyclobutylalanine di-TFA salt and N-(1-(S)-3-(S)-((4-(N-(4-fluorobenzyloxycarbonyl)-N-(prop-1-yl)amino)piperidin-1-yl)methyl)-4-(S)-phenylcyclopent-1-yl)-D-cyclobutylalanine di-TFA salt Using essentially the same procedures as in Example 16, but substituting D/L-cyclobutylalanine t-butyl ester in Step A, the lower 3 products from Step A in Step B, and 4-(N-(4-fluorobenzyloxycarbonyl)-N-(prop-1-yl)amino) piperidine hydrochloride in Step C (separation of all three diastereomers by Prep TLC, 75% ethyl acetate in hexanes), the three diastereomeric title compounds were prepared.

(Each isomer): HPLC/MS (ESI): m/z 594 (M+1).

EXAMPLE 26

N-(1-(R)-3-(S)-((4-(N-(4-Chlorobenzyloxycarbonyl)-N-(prop-1-yl)amino)piperidin-1-yl)methyl)-4-(S)-phenylcyclopent-1-yl)-D-cyclobutylalanine di-TFA salt, N-(1-(R)-3-(S)-((4-(N-(4-chlorobenzyloxycarbonyl)-N-(prop-1-yl)amino)piperidin-1-yl)methyl)-4-(S)-phenylcyclopent-1-yl)-L-cyclobutylalanine di-TFA salt and N-(l-(S)-3-(S)-((4-(N-(4-chlorobenzyloxycarbonyl)-N-(prop-1-yl)amino)piperidin-1-yl)methyl)-4-(S)-phenylcyclopent-1-yl)-D-cyclobutylalanine di-TFA salt Using essentially the same procedures as in Example 16, but substituting D/L-cyclobutylalanine t-butyl ester in Step A, the lower 3 products from Step A in Step B, and 4-(N-(4-chlorobenzyloxycarbonyl)-N-(prop-1-yl)amino) piperidine hydrochloride in Step C (separation of all three diastereomers by Prep TLC, 75% ethyl acetate in hexanes), the three diastereomeric title compounds were prepared.

(Each isomer): HPLC/MS (ESI): m/z 610 (M+1).

EXAMPLE 27

N-(1-(R)-3-(S)-((4-(N-(3,4-Difluorobenzyloxycarbonyl)-N-(prop-1-yl)amino) piperidin-1-yl)methyl)-4-(S)-phenylcyclopent-1-yl)-D-cyclobutylalanine di-TFA salt, N-(1-(R)-3-(S)-((4-(N-(3,4-difluorobenzyloxycarbonyl)-N-(prop-1-yl)amino)piperidin-1-yl)methyl)-4-(S)-phenylcyclopent-1-yl)-L-cyclobutylalanine di-TFA salt and N-(1-(S)-3-(S)-((4-(N-(3,4-difluorobenzyloxycarbonyl)-N-(prop-1-yl)amino) piperidin-1-yl)methyl)-4-(S)-phenylcyclopent-1-yl)-D-cyclobutylalanine di-TFA salt Using essentially the same procedures as in Example 16, but substituting D/L-cyclobutylalanine t-butyl ester in Step A, the lower 3 products from Step A in Step B, and 4-(N-(3,4-difluorobenzyloxycarbonyl)-N-(prop-1-yl) amino)piperidine hydrochloride in Step C (separation of all three diastereomers by Prep TLC, 75% ethyl acetate in hexanes), the three diastereomeric title compounds were prepared.

(Each isomer): HPLC/MS (ESI): m/z 612 (M+1).

EXAMPLE 28

N-(1-(R)-3-(S)-((4-(N-(4-Nitrobenzyloxycarbonyl)-N-(allyl)amino)piperidin-1-yl)methyl)-4-(S)-phenylcyclopent-1-yl)-D-cyclohexylglycine di-TFA salt and N-(1-(S)-3-(S)-((4-(N-(4-nitrobenzyloxycarbonyl)-N-(allyl)amino)piperidin-1-yl)methyl)-4-(S)-phenylcyclopent-1-yl)-D-cyclohexylglycine di-TFA salt Using essentially the same procedures as in Example 16, but substituting D-cyclohexylglycine t-butyl ester in Step A, the mixture of products from Step A in Step B, and 4-(N-(4-nitrobenzyloxycarbonyl)-N-(allyl)amino)piperidine hydrochloride in Step C (separation of the two diastereomers by Prep TLC, 75% ethyl acetate in hexanes), the two diastereomeric title compounds were prepared.

(Each isomer): HPLC/MS (ESI): m/z 633 (M+1).

EXAMPLE 29

N-(1-(R)-3-(S)-((4-(N-(4-Fluorobenzyloxycarbonyl)-N-(prop-1-yl)amino)piperidin-1-yl)methyl)-4-(S)-phenylcyclopent-1-yl)-D-cyclohexylglycine di-TFA salt and N-(1-(S)-3-(S)-((4-(N-(4-fluorobenzyloxycarbonyl)-N-(prop-1-yl)amino) piperidin-1-yl)methyl)4-(S)-phenylcyclopent-1-yl)-D-cyclohexylglycine di-TFA salt Using essentially the same procedures as in Example 16, but substituting D-cyclohexylglycine t-butyl ester in Step A, the mixture of products from Step A in Step B, and 4-(N-(4-fluorobenzyloxycarbonyl)-N-(prop-1-yl)amino) piperidine hydrochloride in Step C (separation of the two diastereomers by Prep TLC, 75% ethyl acetate in hexanes), the two diastereomeric title compounds were prepared.

(Each isomer): HPLC/MS (ESI): m/z 608 (M+1).

EXAMPLE 30

N-(1-(R)-3-(S)-((4-(N-(4-Chlorobenzyloxycarbonyl)-N-(prop-1-yl)amino) piperidin-1-yl)methyl)-4-(S)-phenylcyclopent-1-yl)-D-cyclohexylglycine di-TFA salt and N-(1-(S)-3-(S)-((4-(N-(4-chlorobenzyloxycarbonyl)-N-(prop-1-yl)amino)piperidin-1-yl)methyl)-4-(S)-phenylcyclopent-1-yl)-D-cyclohexylglycine di-TFA salt Using essentially the same procedures as in Example 16, but substituting D-cyclohexylglycine t-butyl ester in Step A, the mixture of products from Step A in Step B, and 4-(N-(4-chlorobenzyloxycarbonyl)-N-(prop-1-yl)amino) piperidine hydrochloride in Step C (separation of the two diastereomers by Prep TLC, 75% ethyl acetate in hexanes), the two diastereomeric title compounds were prepared.

(Each isomer): HPLC/MS (ESI): m/z 624 (M+1).

EXAMPLE 31

N-(1-(R)-3-(S)-((4-(N-(3,4-Difluorobenzyloxycarbonyl)-N-(prop-1-yl)amino) piperidin-1-yl)methyl)-4-(S)-phenylcyclopent-1-yl)-D-cyclohexylglycine di-TFA salt and N-(1-(S)-3-(S)-((4-(N-(3,4-difluorobenzyloxycarbonyl)-N-(prop-1-yl)amino)piperidin-1-yl)methyl)-4-(S)-phenylcyclopent-1-yl)-D-cyclohexylglycine di-TFA salt Using essentially the same procedures as in Example 16, but substituting D-cyclohexylglycine t-butyl ester in Step A, the mixture of products from Step A in Step B, and 4-(N-(3,4-difluorobenzyloxycarbonyl)-N-(prop-1-yl)amino) piperidine hydrochloride in Step C (separation of the two diastereomers by Prep TLC, 75% ethyl acetate in hexanes), the two diastereomeric title compounds were prepared.

(Each isomer): HPLC/MS (ESI): m/z 626 (M+1).

EXAMPLE 32

N-(1-(R)-3-(S)-((4-(N-(3-Fluorobenzyloxycarbonyl)-N-(prop-1-yl)amino)piperidin-1-yl)methyl)-4-(S)-phenylcyclopent-1-yl)-D-cyclohexylglycine di-TFA salt and N-(1-(S)-3-(S)-((4-(N-(3-fluorobenzyloxycarbonyl)-N-(prop-1-yl)amino) piperidin-1-yl)methyl)4-(S)-phenylcyclopent-1-yl)-D-cyclohexylglycine di-TFA salt Using essentially the same procedures as in Example 16, but substituting D-cyclohexylglycine t-butyl ester in Step A, the mixture of products from Step A in Step B, and 4-(N-(3-fluorobenzyloxycarbonyl)-N-(prop-1-yl)amino) piperidine hydrochloride in Step C (separation of the two diastereomers by Prep TLC, 75% ethyl acetate in hexanes), the two diastereomeric title compounds were prepared.

(Each isomer): HPLC/MS (ESI): m/z 608 (M+1).

EXAMPLE 33

N-(1-(R)-3-(S)-((4-(N-(4-Chlorobenzyloxycarbonyl)-N-(prop-1-yl)amino) piperidin-1-yl)methyl)-4-(S)-(3-fluorophenyl) cyclopent-1-yl)-(R)-cyclohexylglycine di-hydrochloride salt Step A: Methyl (+−)-trans-4-methylene-2-(3-fluorophenyl) cyclopentanoate A mixture of methyl trans-3-fluorocinnamate (41.25 g, 229 mmol), tetrakis(triphenylphosphine) palladium(0) (18.5 g, 16 mmol), 1,2-bis(diphenylphosphino)ethane (5.5 g, 13.7 mmol) and 2-((trimethylsilyl)methyl)-2-propen-1-yl acetate (42.66 g, 229 mmol) in THF (300 mL) under nitrogen was heated to reflux for 6 h and then stirred at rt for 16 h. The reaction was diluted with hexane and filtered to remove yellow precipitate. The volatiles were then removed in vacuo and the residue was purified by FC (3 to 5% ethyl acetate in hexanes) to afford the title compound (45 g).

NMR (CDCl$_3$) δ: 2.52 (m, 1H), 2.68 (m, 1H), 2.8–2.9 (m, 2H), 2.95 (ddd, 1H), 3.45 (ddd, 1H), 3.63 (s, 3H), 4.96 (m, 2H), 6.9–7.0 (m, 2H), 7.03 (d, 1H), 7.2–7.3 (m, 1H).

Step B: (+−)-trans4-Methylene-2-(3-fluorophenyl)cyclopentanoic acid

To a solution of methyl (+−)-trans-4-methylene-2-(3-fluoro)phenylcyclopentanoate prepared as in Example 33, Step A (47 g, 200 mmol) in methanol (500 mL) was added 5N sodium hydroxide (200 mL, 1000 mmol). The reaction was stirred at rt for 60 h then concentrated in vacuo. The residue was taken up in water, acidified with 2M hydrochloric acid and extracted twice with methylene chloride. The organic layers were each washed with brine, dried over sodium sulfate, combined and concentrated in vacuo to give the crude title acid (40.8 g) which was used directly in Step C.

Step C: (+)-trans-1-Hydroxymethyl-4-methylene-2-(3-fluorophenyl)cyclopentane and (−)-trans-1-hydroxymethyl-4-methylene-2-(3-fluorophenyl)cyclopentane A solution of (+−)-trans-4-methylene-2-(3-fluorophenyl)cyclopentanoate (5.2 g, 23.6 mmol) from Step B in THF (100 mL) was cooled to 0° C. under nitrogen and 1M lithium aluminum hydride (LAH) in THF (35.4 mL) was added dropwise over 10 min. The reaction was stirred at rt for 16 h, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (25% ethyl acetate in hexanes) to afford the racemic title product (4.1 g) as a an oil. Chiral Prep HPLC on a 2 cm×25 cm Chiracel OD column eluting with 5% isopropanol in hexanes (25 injections) afforded the (−)-enantiomer, $[\alpha]_D$=−45.5 (MeOH, c=0.9), as the first eluting peak ($R_t$=17.5 min) and the (+)-enantiomer (1.87 g), $[\alpha]_D$=+45.0 (MeOH, c=1.0), as the second peak ($R_t$=22.0 min).

NMR (CDCl$_3$) δ: 2.2–2.35 (m, 2H), 2.5 (m, 1H), 2.65–2.85 (m, 2H), 2.9 (m, 1H), 3.51 and 3.68 (dABq, 2H), 4.93 (m, 2H), 6.9-7.0 (m, 2H), 7.06 (d, 1H), 7.3–7.4 (m, 1H).

Step D: (+)-trans-3-Hydroxymethyl-4-(3-fluorophenyl)cyclopentanone

A solution of (+)-trans-1-hydroxymethyl-4-methylene-2-(3-fluorophenyl)cyclopentane from Step C (1.87 g, 9.0 mmol) in methanol (75 mL) was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to rt over 2 h. The mixture was treated with 10 drops of sulfuric acid (c) in water (2 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (50% ethyl acetate in hexanes) to give the title compound (1.87 g) ), $[\alpha]_D$=+132 (MeOH, c=1.2),.

NMR (CDCl$_3$) δ: 2.3–2.45 (m, 2H), 2.5 (m, 1H), 2.61 and 2.77 (dABq, 2H), 2.28 (ddd, 1H), 3.61 and 3.75 (dABq, 2H), 6.9–7.0 (m, 2H), 7.06 (d, 1H), 7.3–7.4 (m, 1H).

Step E: N-(1-(R)-3-(S)-Hydroxymethyl-4-(S)-phenylcyclopent-1-yl)-(R)-cyclohexylglycine t-butyl ester To a solution of (+)-trans-3-hydroxymethyl-4-(3-fluorophenyl)cyclopentanone from Step D (500 mg, 2.4 mmol) in 1,2-dichloroethane (25 mL) was added (R)-cyclohexylglycine t-butyl ester (0.61 g, 2.88 mmol) and acetic acid (0.15 mL, 2.64 mmol). After 15 min, sodium triacetoxyborohydride (1.0 g, 4.8 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with 30% ethyl acetate in hexanes to give the product (936 mg) as clean major higher $R_f$ title compound (425 mg) plus a mixture of C-1 isomers (511 mg) as the free amines.

Step F: N-(1-(R)-3-(S)-Formyl-4-(S)-phenylcyclopent-1-yl)-(R)-cyclohexylglycine t-butyl ester To a solution of (1-(R)-3-(S)-(hydroxymethyl)-4-(S)-phenylcyclopent-1-yl)-L-cyclohexylglycine (higher $R_f$ from Step E) (162 mg, 0.4 mmol) in methylene chloride (5 mL) was added TPAP (7 mg, 0.020 mmol) and N-methylmorholine (70 mg, 0.60 mmol). The reaction was stirred under nitrogen at rt for 1 h and was then concentrated. The residue was purified by FC (15% ethyl acetate in hexanes) to give the title product (115 mg) after vacuum drying.

Step G: N-(1-(R)-3-(S)-((4-(N-(4-Chlorobenzyloxycarbonyl)-N-(prop-1-yl)amino)piperidin-1-yl)methyl)4-(S)-(3-fluorophenyl)cyclopent-1-yl)-(R)-cyclohexylglycine t-butyl ester To a solution of N-(1-(R)-3-(S)-formyl4-(S)-phenylcyclopent-1-yl)-(R)-cyclohexylglycine t-butyl ester (15 mg, 0.036 mmol) from Step F in 1,2-dichloroethane (2 niL) was added 4-N-(4-chlorobenzyloxycarbonyl)-N-(prop-1-yl)amino)piperidine hydrochloride (15 mg, 0.043 mmol) and DIPEA (0.008 mL, 0.047 mmol). After 15 min, sodium triacetoxyborohydride (15 mg, 0.072 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 75% ethyl acetate in hexanes to give the title product as the free amine.

Step H: N-(1-(R)-3-(S)-((4-(N-(4-Chlorobenzyloxycarbonyl)-N-(prop-1-yl)amino)piperidin-1-yl)methyl)-4-(S)-(3-fluorophenyl)cyclopent-1-yl)-(R)-cyclohexylglycine di-hydrochloride salt The N-(1-(R)-3-(S)-((4-(N-(4-chlorobenzyloxycarbonyl)-N-(prop-1-yl)amino)piperidin-1-yl)methyl)-4-(S)-(3-fluorophenyl)cyclopent-1-yl)-(R)-cyclohexylglycine t-butyl ester from Step F was taken up in TFA (2 mL) and aged at rt for 16 h. The volatiles were evaporated under a stream of nitrogen. The residue was taken up in methanol and adsorbed onto a 500 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, addition of excess 1M hydrogen chloride in ether and evaporation to dryness.

HPLC/MS (ESI): m/z 642 (M+1).

EXAMPLE 34

Using essentially the same procedure as in Example 33, Steps G and H, but substituting the appropriate 4-substituted piperidine, the following compounds were prepared.

EXAMPLE 34A

N-(1-(R)-3-(S)-((4-(N-(3-Fluorobenzyloxycarbonyl)-
N-(prop-1-yl)amino)piperidin-1-yl)methyl)4-(S)-(3-
fluorophenyl)cyclopent-1-yl)-(R)-cyclohexylglycine
di-hydrochloride salt HPLC/MS (ESI): m/z 626 (M+1).

EXAMPLE 34B

N-(1-(R)-3-(S)-((4-(N-(3,4-
Difluorobenzyloxycarbonyl)-N-(prop-1-yl)amino)
piperidin-1-yl)methyl)-4-(S)-(3-fluorophenyl)
cyclopent-1-yl)-(R)-cyclohexylglycine di-
hydrochloride salt HPLC/MS (ESI): m/z 644 (M+1).

EXAMPLE 40

N-(2-Methylprop-1-yl)-N-(1-(SR)-3-(SR)-((4-(N-(4-
nitrobenzyloxycarbonyl)-N-(allyl)amino)piperidin-1-
yl)methyl)-4-(SR)-phenylcyclopent-1-yl)glycine di-
hydrochloride salt Step A: 1-(SR)-Benzyloxycarbonylamino-3-(SR)-
hydroxymethyl-4-(SR)-phenylcyclopentane (Higher $R_f$
isomer) and 1-(RS)-benzyloxycarbonylamino-3-(SR)-
hydroxymethyl-4-(SR)-phenylcyclopentane (Lower $R_f$
isomer)

Using essentially the same procedure as in Example 8, Step H, but using benzyl chloroformate in place of di-t-butyl dicarbonate, 1-(SR and RS)-benzylamino-3-(SR)-hydroxymethyl-4-(SR)-phenylcyclopentane (13 g) was converted to the title compounds. Prep LC (30% ethyl acetate in hexanes) afforded pure minor, higher $R_f$ product (4.0 g), then a mixture and finally pure major, lower $R_f$ product (6.6 g).

Step B: 1-(SR)-Benzyloxycarbonylamino-3-(SR)-t-butyldimethylsilyloxymethyl-4-(SR)-phenylcyclopentane (Higher $R_f$ isomer) and 1-(RS)-benzyloxycarbonylamino-3-(SR)-t-butyldimethylsilyloxymethyl4-(SR)-phenylcyclopentane (Lower $R_f$ isomer)

To a solution of 1-(SR)-benzyloxycarbonylamino-3-(SR)-hydroxymethyl-4-(SR)-phenylcyclopentane (Higher $R_f$ isomer from Step A) (3.96 g, 12.2 mmol) in methylene chloride (100 mL) was added DIPEA (6.4 mL, 37 mmol) and t-butyldimethylsilyl chloride (2.0 g, 13.4 mmol). The reaction was stirred at rt for 16 h when a second portion of t-butyldimethylsilyl chloride (1.0 g, 6.7 mmol) was added. After a further 24 h, the reaction was diluted with methylene chloride and poured into dilute hydrochloric acid. The layers were separated and the organic layer was washed with brine containing sodium bicarbonate, dried over sodium sulfate and concentrated. The residue was purified by FC (5 to 40% ethyl acetate in hexanes) to give the title compound (4.7 g). After eluting with 75% ethyl acetate in hexanes, recovered starting material was obtained.

In a similar way, 1-(RS)-benzyloxycarbonylamino-3-(SR)-hydroxymethyl-4-(SR)-phenylcyclopentane (lower $R_f$ isomer from Step A) (6.6 g, 20.3 mmol) was converted to the lower $R_f$ title compound (7.7 g) and recovered starting material.

Step C: 1-(SR)-N-(2-Methylprop-2-en-1-yl)-N-(benzyloxycarbonyl)amino-3-(SR)-t-butyldimethylsilyloxymethyl-4-(SR)-phenylcyclopentane (Higher $R_f$ isomer) and 1-(RS)- N-(2-methylprop-2-en-1-yl)-N-(benzyloxycarbonyl)amino -3-(SR)-t-butyldimethylsilyloxymethyl-4-(SR)-phenylcyclopentane (Lower $R_f$ isomer)

To a solution of 1-(SR)-benzyloxycarbonylamino-3-(SR)-t-butyldimethylsilyloxymethyl-4-(SR)-phenylcyclopentane (Higher $R_f$ isomer from Steps A-B) (500 mg, 1.14 mmol) and 1-bromo-2-methylprop-2-ene (0.175 mL, 1.7 mmol) in DMF (10 mL) was added at rt in portions over 10 min 60% sodium hydride in mineral oil (68 mg, 1.7 mmol). After 3 h, the reaction was diluted with ether and quenched into water. The layers were separated and the organic layer was washed with brine containing sodium bicarbonate, dried over sodium sulfate and concentrated. The residue was purified by FC (5 to 10% ethyl acetate in hexanes) to give the title compound (0.32 g).

NMR (CDCl$_3$): δ–0.06 (s, 3H), –0.05 (s, 3H), 0.84 (s, 9H), 1.54 (s, 3H), 1.65–1.8 (m, 3H), 1.95–2.2 (m, 3H), 2.8–3.0 (M, 1H), 3.3-3.45 (m, 1H), 3.45–3.5 (m, 1H), 3.7–3.9 (m, 2H), 4.80 (d, 2H), 5.14 (br s, 2H), 7.15 (m, 2H), 7.25 (m, 5H), 7.34 m, 3H).

In a similar way, 1-(RS)-benzyloxycarbonylamino-3-(SR)-t-butyldimethylsilyloxymethyl-4-(SR)-phenylcyclopentane (lower $R_f$ isomer from Step A–B) (1.0 g, 2.3 mmol) was converted to the lower $R_f$ title compound (0.55 g).

Step D: 1-(SR)-N-(2-Methylprop-1-yl)amino-3-(SR)-t-butyldimethylsilyloxymethyl-4-(SR)-phenylcyclopentane (Higher $R_f$ isomer) and 1-(RS)-N-(2-methylprop-1-yl)amino-3-(SR)-t-butyldimethylsilyloxymethyl-4-(SR)-phenylcyclopentane (Lower $R_f$ isomer)

To a solution of 1-(SR)-N-(2-methylprop-2-en-1-yl)-N-(benzyloxycarbonyl)amino-3-(SR)-t-butyldimethylsilyloxymethyl-4-(SR)-phenylcyclopentane (Higher $R_f$ isomer from Steps A–C) (320 mg, 0.65 mmol) in methanol (5 mL) was added 10% Pd/C (50 mg) and a drop of DIPEA. The mixture was hydrogenated at 40 psi for 2 h. The reaction was filtered and the filtrate was concentrated. The residue of title compound was used directly in Step E.

NMR (CDCl$_3$): δ–0.05 (s, 3H), –0.04 (s, 3H), 0.84 (s, 9H), 0.89 (s, 3H), 0.91 (s, 3 H), 1.35 (ddd, 1H), 1.73 (hept, 1H), 1.93 (m, 2H), 2.15 (m, 1H), 2.25 (m, 1H), 2.38 (d, 2H), 2.96 (q, 1H), 3.28 (m, 1H), 3.49 (dABq, 2H), 7.15 (m, 3H), 7.24 (m, 2H).

In a similar way, 1-(RS)-N-(2-methylprop-2-en-1-yl)-N-(benzyloxycarbonyl)amino -3-(SR)-t-butyldimethylsilyloxymethyl-4-(SR)-phenylcyclopentane (lower $R_f$ isomer from Step A–C) (0.55 g, 1.1 mmol) was converted to the lower $R_f$ title compound (0.475 g).

Step E: N-(2-Methylprop-1-yl)-N-(1-(SR)-3-(SR)-t-butyldimethylsilyloxymethyl-4-(SR)-phenylcyclopent-1-yl)-glycine (Higher $R_f$ isomer) and N-(2-methylprop-1-yl)-N-(1-(RS)-3-(SR)-t-butyldimethylsilyloxymethyl-4-(SR)-phenylcyclopent-1-yl)-glycine (Lower $R_f$ isomer)

A solution of 1-(SR)-N-(2-methylprop-1-yl)amino-3-(SR)-t-butyldimethylsilyloxymethyl-4-(SR)-phenylcyclopentane (Higher $R_f$ isomer from Steps A–D) (0.65 mmol), t-butyl bromoacetate (125 mg, 0.65 mmol) and DIPEA (1.1 mL, 6.5 mmol) in acetonitrile (15 mL) was stirred at rt for 16 h. The reaction was diluted with aqueous sodium carbonate and extracted three times with ethyl acetate. The organic layers were washed with brine containing sodium bicarbonate, dried over sodium sulfate, combined and concentrated. The residue was purified by FC (50% ethyl acetate in hexanes) to give impure product and recovered starting material (135 mg). The impure product fractions were repurified by FC (5% ethyl acetate in hexanes) to afford the title higher $R_f$ compound (0.13 g). The recovered starting material was recycled using the same procedure but doing the reaction at 50 ° C. for 16 h to afford additional title compound (140 mg).

NMR (CDCl₃): δ −0.05 (s, 3H), −0.04 (s, 3H), 0.84 (s, 9H), 0.86 (d, 3H), 0.88 (d, 3 H), 1.44 (s, 9H), 1.70 (hept, 1H), 1.95 (m, 1H), 2.00 (m, 1H), 2.08 (m, 2H), 2.38 (dABq, 2H), 2.90 (m, 1H), 3.26 (ABq, 2H), 3.49 (dABq, 2H), 3.5–3.6 (m, 1H), 7.15 (m,3H),7.24 (m,2H).

In a similar way, but doing the reaction at 50 ° C. for 20 h, 1-(RS)-N-(2-methylprop-1-yl)amino-3-(SR)-t-butyldimethylsilyloxymethyl-4-(SR)-phenylcyclopentane (lower $R_f$ isomer from Steps A–D) (0.375 mg) was converted to the lower $R_f$ title compound (0.435 g).

Step F: N-(2-Methylprop-1-yl)-N-(1-(SR)-3-(SR)-hydroxymethyl-4-(SR)-phenylcyclopent-1-yl)-glycine (Higher $R_f$ isomer) and N-(2-methylprop-1-yl)-N-(1-(RS)-3-(SR)-hydroxymethyl-4-(SR)-phenylcyclopent-1-yl)-glycine (Lower $R_f$ isomer)

A solution of N-(2-methylprop-1-yl)-N-(1-(SR)-3-(SR)-t-butyldimethylsilyloxymethyl-4-(SR)-phenylcyclopent-1-yl)-glycine (Higher $R_f$ isomer from Steps A–E) (270 mg, 0.57 mmol) and 1M TBAF in THF (0.85 mL, 0.85 mmol) in THF (5 mL) was stirred at rt for 1 h. The reaction was concentrated and the residue was purified by FC (20% ethyl acetate in hexanes) to give the title higher $R_f$ product (140 mg).

In a similar way, N-(2-methylprop-1-yl)-N-(1-(RS)-3-(SR)-t-butyldimethylsilyloxymethyl-4-(SR)-phenylcyclopent-1-yl)-glycine (Lower $R_f$ isomer from Steps A–E) (0.435 mg) was converted to the lower $R_f$ title compound (0.300 mg).

Step G: N-(2-Methylprop-1-yl)-N-(1-(SR)-3-(SR)-formyl-4-(SR)-phenylcyclopent-1-yl)-glycine (Higher $R_f$ isomer) and N-(2-methylprop-1-yl)-N-(1-(RS)-3-(SR)-formyl-4-(SR)-phenylcyclopent-1-yl)-glycine (Lower $R_f$ isomer)

Using essentially the same procedure as in Example 1, Step C, N-(2-methylprop-1-yl)-N-(1-(SR)-3-(SR)-hydroxymethyl4-(SR)-phenylcyclopent-1-yl)-glycine (Higher $R_f$ isomer from Steps A–F) (140 mg, 0.39 mmol) was oxidized to the title compound (100 mg).

In a similar way, N-(2-methylprop-1-yl)-N-(1-(RS)-3-(SR)-hydroxymethyl-4-(SR)-phenylcyclopent-1-yl)-glycine (Lower $R_f$ isomer from Steps A–F) (0.150 mg) was converted to the lower $R_f$ title compound (0.140 mg).

Step H: N-(2-Methylprop-1-yl)-N-(1-(SR)-3-(SR)-((4-(N-(4-nitrobenzyloxycarbonyl)-N-(allyl)amino)piperidin-1-yl)methyl)-4-(SR)-phenylcyclopent-1-yl)glycine t-butyl ester (higher $R_f$ isomer)

To a solution of N-(2-methylprop-1-yl)-N-(1-(SR)-3-(SR)-formyl-4-(SR)-phenylcyclopent-1-yl)-glycine (Higher $R_f$ isomer from Steps A–G) (25 mg, 0.070 mmol) in 1,2-dichloroethane (2 mL) was added 4-(N-(4-nitrobenzyloxycarbonyl)-(N-allyl)amino)piperidine hydrochloride (40 mg, 0.11 mmol) and DIPEA (0.020 mL, 0.11 mmol). After 15 min, sodium triacetoxyborohydride (45 mg, 0.21 mmol) was added and the reaction was stirred at rt for 4 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 5% methanol in methylene chloride to give the title product (65 mg) as the free amine.

Step I: N-(2-Methylprop-1-yl)-N-(1-(SR)-3-(SR)-((4-(N-(4-nitrobenzyloxycarbonyl)-N-(allyl)amino)piperidin-1-yl)methyl)4-(SR)-phenylcyclopent-1-yl)glycine di-TFA salt A solution of N-(2-methylprop-1-yl)-N-(1-(SR)-3-(SR)-((4-(N-(4-nitrobenzyloxycarbonyl)-N-(allyl)amino) piperidin-1-yl)methyl)-4-(SR)-phenylcyclopent-1-yl) glycine t-butyl ester (higher $R_f$ isomer from Steps A–H) in TFA (4 mL) was heated at 50° C. for 4 h and then the volatiles were removed under a stream of nitrogen. An additional 2×3 mL of methylene chloride were evaporated to afford the title compound as the di-TFA salt (95 mg).

HPLCIMS (ESI): m/z 607 (M+1).

Using essentially the same procedure as in Example 40, Steps H and I, but substituting the appropriate 4-substituted piperidine in Step H, the following compounds were prepared.

EXAMPLE 41

N-(2-Methylprop-1-yl)-N-(1-(SR)-3-(SR)-((4-(N-(4-nitrobenzylaminocarbonyl)-N-(ethyl)amino) piperidin-1-yl)methyl)-4-(SR)-phenylcyclopent-1-yl) glycine di-TFA salt HPLC/MS (ESI): m/z 594 (M+1).

EXAMPLE 42

N-(2-Methylprop-1-yl)-N-(1-(SR)-3-(SR)-((4-(N-(4-nitrobenzylaminocarbonyl)-N-(allyl)amino) piperidin-1-yl)methyl)-4-(SR)-phenylcyclopent-1-yl) glycine di-TFA salt HPLC/MS (ESI): m/z 606 (M+1).

Using essentially the same procedure as in Example 40, Steps H and I, but substituting the lower $R_f$ aldehyde from Steps A–G and the appropriate 4-substituted piperidine in Step H, the following compounds were prepared.

EXAMPLE 43

N-(2-Methylprop-1-yl)-N-(1-(RS)-3-(SR)-((4-(N-(4-nitrobenzylaminocarbonyl)-N-(ethyl)amino) piperidin-1-yl)methyl)-4-(SR)-phenylcyclopent-1-yl) glycine di-TFA salt HPLC/MS (ESI): m/z 594 (M+1).

EXAMPLE 44

N-(2-Methylprop-1-yl)-N-(1-(RS)-3-(SR)-((4-(N-(4-nitrobenzyloxycarbonyl)-N-(allyl)amino)piperidin-1-yl)methyl)-4-(SR)-phenylcyclopent-1-yl)glycine di-TFA salt HPLC/MS (ESI): m/z 607 (M+1).

EXAMPLE 45

N-(2-Methylprop-1-yl)-N-(1-(RS)-3-(SR)-((4-(N-(phenylaminocarbonyl)-N-(prop-1-yl)amino) piperidin-1-yl)methyl)-4-(SR)-phenylcyclopent-1-yl) glycine di-TFA salt HPLC/MS (ESI): m/z 549 (M+1).

EXAMPLE 46

N-(Cyclobutylmethyl)-N-(1-(R)-3-(S)-((4-(N-(4-fluorobenzyloxycarbonyl)-N-(prop-1-yl)amino) piperidin-1-yl)methyl)-4-(S)-phenylcyclopent-1-yl) glycine di-HCl salt Step A: N-(1-(R)-3-(S)-Hydroxymethyl)-4-(S)-phenylcyclopent-1-yl)glycine and N-(1-(S)-3-(S)-Hydroxymethyl)-4-(S)-phenylcyclopent-1-yl)glycine To a solution of (+)-trans-3-hydroxymethyl-4-phenylcyclopentan-1-one from Example 8, Step F, Method B (180 mg, 0.96 mmol), glycine t-butyl ester hydrochloride (241 mg, 1.44 mmol) and DIPEA (0.25 mL, 1.44 mmol) in 1,2-dichloroethane (6 mL) was added sodium triacetoxyborohydride (284 mg, 1.92 mmol). The reaction was stirred at rt for 16 h and was then diluted with aq. sodium bicarbonate and extracted three times with methylene chloride. The organic layers were each washed with brine, dried over sodium sulfate, combined and concentrated in vacuo. The residue was purified by FC (50–100% ethyl acetate in hexanes) to give the title product (196 mg) as a 2:1 mixture of C-1 free amine isomers.

NMR (CDCl$_3$): δ1.48 (s, 9H), 1.6–1.7 (m, 1.3H), 1.8–2.0 (2 m, 1.7H), 2.23 ddd, 0.3H), 2.3–2.45 (m, 2H), 2.68 (ddd, 0.7H), 3.2–3.4 (2 m and 2 s, 3H), 3.45–3.65 (dABq (major) and d (minor), 2H), 3.96 (d, 1H), 7.2–7.35 (m, 5H).

Step B: N-(Cyclobutylmethyl)-N-(1-(R)-3-(S)-hydroxymethyl)-4-(S)-phenylcyclopent-1-yl)glycine (major, higher R$_f$) and N-(cyclobutylmethyl)-N-(1-(S)-3-(S)-hydroxymethyl)-4-(S)-phenylcyclopent-1-yl)glycine (minor, lower R$_f$)

To a solution of N-(1-(R and S)-3-(S)-hydroxymethyl)4-(S)-phenylcyclopent-1-yl)glycine from Step A (180 mg, 0.59 mmol), cyclobutylaldehyde (27 mg, 0.32 mmol) and DIPEA (0.25 mL, 1.5 mmol) in 1,2-dichloroethane (6 mL) was added sodium triacetoxyborohydride (175 mg, 1.2 mmol). The reaction was stirred at rt for 16 h and was then diluted with aq. sodium bicarbonate and extracted three times with methylene chloride. The organic layers were each washed with brine, dried over sodium sulfate, combined and concentrated in vacuo. The residue was purified by Prep TLC (30% ethyl acetate in hexanes) to give the title 1-(R) product (45 mg pure, 31 mg mixture with the 1-(S) diastereomer) as the higher R$_f$ C-1 isomer. (Major, higher isomer): NMR (CDCl$_3$): δ1.49 (s, 9H), 1.6–1.85 (m, 4H), 1.85–1.95 (m, 2H), 2.0–2.15 (m, 2H), 2.24 (p, 1H), 2.2.33 (m, I H), 2.53 (hept, 1H), 2.7–2.8 (m, 3H), 3.31 (s, 2H), 3.4–3.5 (m, 1H), 3.48 and 3.61 (dABq, 2H), 7.24 (tt, 1H), 7.25–7.35 (m, 4H).

Repurification of the mixture on Prep TLC afforded a sample of pure 1-(S) minor, lower R$_f$ isomer.

(Minor, lower isomer): NMR (CDCl$_3$): δ1.47 (s, 9H), 1.6–1.75 (m, 3H), 1.75–1.85 (m, 1H), 1.9–2.0 (m, 1H), 2.05–2.25 (m, 4H), 2.3 (m, 1H), 2.54 (hept, 1H), 2.78 (ddd, 2H), 3.09 (q, 1H), 3.35 (ABq, 2H), 3.55 (m, 1H), 3.61 (dABq, 2H), 7.24 tt, 1H), 7.25–7.35 (m, 4H).

Step C: N-(Cyclobutylmethyl)-N-(1-(R)-3-(S)-formyl)-4-(S)-phenylcyclopent-1-yl)glycine Using essentially the same procedure as in Example 1, Step C, N-(cyclobutylmethyl)-N-(1-(R)-3-(S)-hydroxymethyl)4-(S)-phenylcyclopent-1-yl)glycine (higher R$_f$ isomer from Steps B) (45 mg, 0.12 mmol) was oxidized to the title compound (56 mg crude without purification).

Step D: N-(Cyclobutylmethyl)-N-(1-(R)-3-(S)-((4-(N-(4-fluorobenzyloxycarbonyl)-N-(prop-1-yl)amino)piperidin-1-yl)methyl)-4-(S)-phenylcyclopent-1-yl)glycine t-butyl ester To a solution of N-(cyclobutylmethyl)-N-(1-(R)-3-(S)-formyl)-4-(S)-phenylcyclopent-1-yl)glycine (higher R$_f$ isomer from Steps B–C) (22 mg, 0.059 mmol) in 1,2-dichloroethane (1 mL) was added 4-(N-(4-fluorobenzyloxycarbonyl)-N-(prop-1-yl)amino)piperidine hydrochloride (29 mg, 0.089 mmol) and DIPEA (0.015 mL, 0.089 mmol). After 15 min, sodium triacetoxyborohydride (18 mg, 0.12 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 30% ethyl acetate in hexanes to give the title product (23 mg) as the free amine.

Step E: N-(Cyclobutylmethyl)-N-(1-(R)-3-(S)-((4-(N-(4-fluorobenzyloxycarbonyl)-N-(prop-1-yl)amino)piperidin-1-yl)methyl)-4-(S)-phenylcyclopent-1-yl)glycine di-HCl salt A solution of N-(cyclobutylmethyl)-N-(1-(R)-3-(S)-((4-(N-(4-fluorobenzyloxycarbonyl)-N-(prop-1-yl)amino) piperidin-1-yl)methyl)-4-(S)-phenylcyclopent-1-yl)glycine t-butyl ester (higher R$_f$ isomer from Steps B–D) in TFA (4 mL) was stirred at rt for 16 h and then the volatiles were removed under a stream of nitrogen. An additional 2×3 mL of toluene were evaporated and the residue was purified by Prep TLC (95:5:1:1 methylene chloride:methanol:water:NH$_4$OH). The free amine (5 mg) was taken up in methylene chloride and excess 1M hydrogen chloride in ether was added. The mixture was evaporated to dryness to afford the title compound as the di-HCl salt (5.3 mg).

HPLC/MS (ESI): m/z 594 (M+1).

EXAMPLE 47

N-(Cyclopropylmethyl)-N-(1-(R)-3-(S)-((4-(N-(4-fluorobenzyloxycarbonyl)-N-(prop-1-yl)amino) piperidin-1-yl)methyl)-4-(S)-phenylcyclopent-1-yl) glycine di-HCl salt Using essentially the same procedure as in Example 46, Steps B–E, but substituting cyclopropylaldehyde in Step B, the title compound was prepared.

HPLC/MS (ESI): m/z 580 (M+1).

EXAMPLE 48

N-(Cyclobutylmethyl)-N-(1-(S)-3-(S)-((4-(N-(4-fluorobenzyloxycarbonyl)-N-(prop-1-yl)amino) piperidin-1-yl)methyl)-4-(S)-phenylcyclopent-1-yl) glycine di-HCl salt Using essentially the same procedure as in Example 46, Steps B–E, but substituting the lower R$_f$ product from Step B in Steps C–E, the title compound could be prepared.

EXAMPLE 49

N-(Cyclopropylmethyl)-N-(1-(S)-3-(S)-((4-(N-(4-fluorobenzyloxycarbonyl)-N-(prop-1-yl)amino) piperidin-1-yl)methyl)-4-(S)-phenylcyclopent-1-yl) glycine di-HCl salt Using essentially the same procedure as in Example 46, Steps B–E, but substituting cyclopropyl aldehyde in Step B and using the lower R$_f$ product from Step B in Steps C–E, the title compound was prepared.

HPLC/MS (ESI): m/z 580 (M+1).

EXAMPLE 50

N-(Cyclohexyl)-N-(1-(S)-3-(S)-((4-(N-(4-fluorobenzyloxycarbonyl)-N-(prop-1-yl)amino) piperidin-1-yl)methyl)-4-(S)-phenylcyclopent-1-yl) glycine di-HCl salt Step A: N-(1-(S)-3-(S)-t-Butyldimethylsilyloxymethyl)-4-(S)-phenylcyclopent-1-yl)glycine (major, higher R$_f$) and N-(1-(R)-3-(S)-t-butyldimethylsilyloxymethyl)-4-(S)-phenylcyclopent-1-yl)glycine (minor, lower R$_f$)

To a solution of (+)-trans-3-t-butyldimethylsilyloxymethyl-4-phenylcyclopentan-1-one from Example 16, Step A, Method B (332 mg, 1.1 mmol), glycine t-butyl ester hydrochloride (275 mg, 1.64 mmol) and DIPEA (0.285 mL, 1.64 mmol) in 1,2-dichloroethane (13 mL) was added sodium triacetoxyborohydride (323 mg, 2.18 mmol). The reaction was stirred at rt for 16 h and was then diluted with aq. sodium bicarbonate and extracted three times with methylene chloride. The organic layers were each washed with brine, dried over sodium sulfate, combined and concentrated in vacuo. The residue was purified by FC (10% ethyl acetate in hexanes) to give the title product (437 mg) as a 2.6:1 mixture of C-1 free amine isomers.
(Note: The product C-1 isomer ratio here with the silyl ether is opposite to that of Example 46 with the free alcohol. Also, note that the relative retention on TLC of the NH intermediates are opposite that of the N-alkylation products of Step B.) Careful FC (5% ethyl acetate in hexanes) of an initial sample afforded the separated isomers.

(Major, higher isomer): NMR (CDCl$_3$): δ–0.05 (s, 3H), –0.04 (s, 3H), 0.87 (s, 9H), 1.42 (m, 1H), 1.50 (s, 9H), 1.98 (dd, 2H), 2.17 (m, 1H), 2.27 (dt, 1H), 3.00 (q, 1 H), 3.3–3.4 (m and s, 3H), 3.45 and 3.60 (dABq, 2H), 7.15–7.25 (m, 3H), 7.25–7.35 (m, 2H).

(Minor, lower isomer): NMR (CDCl$_3$): δ–0.05 (s, 3H), –0.04 (s, 3H), 0.87 (s, 9H), 1.50 (s, 9H), 1.62 (dt, 1H), 1.75 (ddd, 1H), 1.95 (dt, 1H), 2.25–2.4 (2 m, 2H), 2.85 (m, 1H), 3.22 (m, 1H), 3.34 (s, 2H), 3.42 and 3.54 (dABq, 2H), 7.24 (tt, 1H), 7.25–7.35 (m, 4H).

Step B: N-(Cyclohexyl)-N-(1-(S)-3-(S)-hydroxymethyl)-4-(S)-phenylcyclopent-1-yl)glycine (lower, major R$_f$ ) and N-(cyclohexyl)-N-(1-(R)-3-(S)-hydroxymethyl)-4-(S)-phenylcyclopent-1-yl)glycine (higher, minor R$_f$ )

To a solution of N-(1-(R and S)-3-(S)-t-butyldimethylsilyloxymethyl)-4-(S)-phenylcyclopent-1-yl) glycine from Step A (437 mg, 1.04 mmol), cyclohexanone (0.650 mL, 6.24 mmol) and DIPEA (0.272 mL, 1.56 mmol) in 1,2-dichloroethane (10 mL) was added sodium triacetoxyborohydride (693 mg, 0.68 mmol). The reaction was stirred at rt for 16 h when additional cyclohexanone (0.600 mL) and sodium triacetoxyborohydride (300 mg) were added. After a further 48 h, the reaction was complete by HPLC/MS and was diluted with aq. sodium bicarbonate and extracted three times with methylene chloride. The organic layers were each washed with brine, dried over sodium sulfate, combined and concentrated in vacuo. The residue (2 g) was used directly in the following desilylation.

The residue from above was taken up in THF (10 mL) and 1M TBAF in THF (5 mL, 5.0 mmol) was added. The reaction was stirred at rt for 6 h and was then poured into aq. sodium bicarbonate and extracted three times with ethyl acetate. The organic layers were each washed with brine, dried over sodium sulfate, combined and concentrated in vacuo. The residue was purified by FC and Prep TLC (40% ethyl acetate in hexanes) to give the title (R) product (114 mg) as the minor, higher R$_f$ band and the title (S) product (235 mg) as the major, lower R$_f$ band.

(Major, higher isomer): NMR (CDCl$_3$): δ1.1–1.4 (m, 5H), 1.48 (s, 9H), 1.5–1.7 (m, 2H), 1.7–2.0 (m, 5H), 2.17 (m, 1H), 2.31 (m, 1H), 2.65–2.8 (m, 2H), 3.24 (Abq, 2H), 3.45–3.55 (m, 2H), 3.6–3.7 (m, 2H), 7.24 (tt, 1H), 7.25–7.35 (m, 4H).

(Minor, lower isomer): NMR (CDCl$_3$): δ1.1–1.4 (m, 5H), 1.48 (s, 9H), 1.6–1.7 (m, 2H), 1.7–2.0 (m, 5H), 2.17 (m, 2H), 2.25 (m, 1H), 2.75 (m, 1H), 3.10 (q, 1H), 3.25 (Abq, 2H), 3.55–3.65 (m, and ABq, 3H), 7.24 (tt, 1H), 7.25–7.35 (m, 4H).

Step C: N-(Cyclohexyl)-N-(1-(S)-3-(S)-formyl)-4-(S)-phenylcyclopent-1-yl)glycine Using essentially the same procedure as in Example 1, Step C, N-(cyclohexyl)-N-(1-(S)-3-(S)-hydroxymethyl)-4-(S)-phenylcyclopent-1-yl)glycine (lower R$_f$ isomer from Step B) (75 mg, 0.19 mmol) was oxidized to the title compound (84 mg crude without purification).

Step D: N-(Cyclohexyl)-N-(1-(R)-3-(S)-((4-(N-(4-fluorobenzyloxycarbonyl)-N-(prop-1-yl)amino)piperidin-1-yl)methyl)-4-(S)-phenylcyclopent-1-yl)glycine t-butyl ester To a solution of N-(cyclohexyl)-N-(1-(S)-3-(S)-formyl)4-(S)-phenylcyclopent-1-yl)glycine (lower R$_f$ isomer from Steps B–C) (16 mg, 0.041 mmol) in 1,2-dichloroethane (1 mL) was added 4-(N-(4-fluorobenzyloxycarbonyl)-N-(prop-1-yl)amino)piperidine hydrochloride (15 mg, 0.045 mmol) and DIPEA (0.011 mL, 0.062 mmol). After 15 min, sodium triacetoxyborohydride (18 mg, 0.12 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 80% ethyl acetate in hexanes to give the title product (14 mg) as the free amine.

Step E: N-(Cyclohexyl)-N-(1-(R)-3-(S)-((4-(N-(4-fluorobenzyloxycarbonyl)-N-(prop-1-yl)amino)piperidin-1-yl)methyl)-4-(S)-phenylcyclopent-1-yl)glycine di-HCl salt A solution of N-(cyclohexyl)-N-(1-(R)-3-(S)-((4-(N-(4-fluorobenzyloxycarbonyl)-N-(prop-1-yl)amino)piperidin-1-yl)methyl)4-(S)-phenylcyclopent-1-yl)glycine t-butyl ester (lower R$_f$ isomer from Steps B–D) in TFA (1 mL) was stirred at rt for 16 h and then the volatiles were removed under a stream of nitrogen. The residue was taken up in methanol and adsorbed onto a 500 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, addition of excess 1M hydrogen chloride in ether and evaporation to dryness.

HPLC/MS (ESI): m/z 608 (M+1).

EXAMPLE 51

N-(1-(R)-3-(S)-((4-(N-(4-Fluorobenzyloxycarbonyl)-N-(prop-1-yl)amino)piperidin-1-yl)methyl)-4-(S)-phenylcyclopent-1-yl)-D-proline di-HCl salt Using essentially the same procedure as in Example 46, but substituting D-proline t-butyl ester in Step A, omitting Step B, and using the higher R$_f$ product from Step A in Steps C–E, the title compound could be prepared.

EXAMPLE 52

N-(1-(S)-3-(S)-((4-(N-(4-Fluorobenzyloxycarbonyl)-N-(prop-1-yl)amino)piperidin-1-yl)methyl)-4-(S)-phenylcyclopent-1-yl)-D-proline di-HCl salt Using essentially the same procedure as in Example 46, but substituting D-proline t-butyl ester in Step A, omitting Step B, and using the lower R$_f$ product from Step A in Steps C–E, the title compound could be prepared.

EXAMPLE 53

N-(1-(R)-3-(S)-((4-(N-(4-Fluorobenzyloxycarbonyl)-N-(prop-1-yl)amino)piperidin-1-yl)methyl)-4-(S)-phenylcyclopent-1-yl)-L-proline di-HCl salt Using essentially the same procedure as in Example 46, but substituting L-proline t-butyl ester in Step A, omitting Step B, and using the higher R$_f$ product from Step A in Steps C–E, the title compound could be prepared.

EXAMPLE 54

N-(1-(S)-3-(S)-((4-(N-(4-Fluorobenzyloxycarbonyl)-N-(prop-1-yl)amino)piperidin-1-yl)methyl)-4-(S)-phenylcyclopent-1-yl)-D-proline di-HCl salt Using essentially the same procedure as in Example 46, but substituting L-proline t-butyl ester in Step A, omitting Step B, and using the lower R$_f$ product from Step A in Steps C–E, the title compound could be prepared.

EXAMPLE 55

Using essentially the same procedure as in Example 33, Steps E and H, but substituting the D or L-amino acid t-butyl ester in Step E and/or the appropriate 4-substituted piperidine G, the following compounds were prepared.

EXAMPLE 55A

N-(1-(R)-3-(S)-((4-(N-(4-Nitrobenzyloxycarbonyl)-N-(prop-2-en-1-yl)amino)piperidin-1-yl)methyl)-4-(S)-(3-fluorophenyl)cyclopent-1-yl)-(S)-cyclopropylalanine di-hydrochloride salt HPLC/MS (ESI): m/z 623 (M+1).

EXAMPLE 55B

N-(1-(R)-3-(S)-((4-(N-(4-Chlorobenzyloxycarbonyl)-N-(prop-1-yl)amino)piperidin-1-yl)methyl)4-(S)-(3-fluorophenyl)cyclopent-1-yl)-(S)-cyclopropylalanine di-hydrochloride salt HPLC/MS (ESI): m/z 614, 616 (M+1, M+3).

EXAMPLE 55C

N-(1-(R)-3-(S)-((4-(N-(3,4-Difluorobenzyloxycarbonyl)-N-(prop-1-yl)amino)piperidin-1-yl)methyl)-4-(S)-(3-fluorophenyl)cyclopent-1-yl)-(S)-cyclopropylalanine di-hydrochloride salt HPLC/MS (ESI): m/z 616 (M+1).

EXAMPLE 55D

N-(1-(R)-3-(S)-((4-(N-(3,4-Difluorobenzyloxycarbonyl)-N-(prop-1-yl)amino)piperidin-1-yl)methyl)-4-(S)-(3-fluorophenyl)cyclopent-1-yl)-(R)-valine di-hydrochloride salt HPLC/MS (ESI): m/z 604 (M+1).

EXAMPLE 55E

N-(1-(R)-3-(S)-((4-(N-(3,4-Difluorobenzyloxycarbonyl)-N-(prop-1-yl)amino)piperidin-1-yl)methyl)-4-(S)-(3-fluorophenyl)cyclopent-1-yl)-(R)-leucine di-hydrochloride salt HPLC/MS (ESI): m/z 618 (M+1).

EXAMPLE 55F

N-(1-(R)-3-(S)-((4-(N-(3,4-Difluorobenzyloxycarbonyl)-N-(prop-1-yl)amino)piperidin-1-yl)methyl)-4-(S)-(3-fluorophenyl)cyclopent-1-yl)-(R)-allo-leucine di-hydrochloride salt HPLCIMS (ESI): m/z 618 (M+1).

EXAMPLE 56

N-Methyl-N-(1-(R)-3-(S)-((4-(N-(3,4-difluorobenzyloxycarbonyl)-N-(prop-1-yl)amino)piperidin-1-yl)methyl)-4-(S)-(3-fluorophenyl)cyclopent-1-yl)-(D)-valine di-hydrochloride salt Step A: Methyl (+–)-trans-4-methylene-2-(3-fluorophenyl)cyclopentanoate A mixture of methyl trans-3-fluorocinnamate (41.25 g, 229 mmol), tetrakis(triphenylphosphine) palladium(0) (18.5 g, 16 mmol), 1,2-bis(diphenylphosphino)ethane (5.5 g, 13.7 mmol) and 2-((trimethylsilyl)methyl)-2-propen-1-yl acetate (42.66 g, 229 mmol) in THF (300 mL) under nitrogen was heated to reflux for 6 h and then stirred at rt for 16 h. The reaction was diluted with hexane and filtered to remove yellow precipitate. The volatiles were then removed in vacuo and the residue was purified by FC (3 to 5% ethyl acetate in hexanes) to afford the title compound (45 g).

$^1$H NMR (CDCl$_3$) δ: 2.52 (m, 1H), 2.68 (m, 1H), 2.8–2.9 (m, 2H), 2.95 (ddd, 1H), 3.45 (ddd, 1H), 3.63 (s, 3H), 4.96 (m, 2H), 6.9–7.0 (m, 2H), 7.03 (d, 1H), 7.2–7.3 (m, 1H).

Step B: (+–)-trans-4-Methylene-2-(3-fluorophenyl)cyclopentanoic acid

To a solution of methyl (+–)-trans4-methylene-2-(3-fluoro)phenylcyclopentanoate prepared as in Step A (47 g, 200 mmol) in methanol (500 mL) was added 5N sodium hydroxide (200 mL, 1000 mmol). The reaction was stirred at rt for 60 h then concentrated in vacuo. The residue was taken up in water, acidified with 2M hydrochloric acid and extracted twice with methylene chloride. The organic layers were each washed with brine, dried over sodium sulfate, combined and concentrated in vacuo to give the crude title acid (40.8 g) which was used directly in Step C.

(Note: The title compound can also be prepared in non-racemic form using essentially the same procedures as Example 8, Steps A–D using the chiral oxazolidine intermediate, [α]$_D$=+93 (MeOH, c=1).)

Step C: (+)-trans-1-Hydroxymethyl-4-methylene-2-(3-fluorophenyl)cyclopentane and (–)-trans-1-hydroxymethyl-4-methylene-2-(3-fluorophenyl)cyclopentane A solution of (+–)-trans-4-methylene-2-(3-fluorophenyl)cyclopentanoate (5.2 g, 23.6 mmol) from Step B in THF (100 mL) was cooled to 0° C. under nitrogen and 1M lithium aluminum hydride (LAH) in THF (35.4 mL) was added dropwise over 10 min. The reaction was stirred at rt for 16 h, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (25% ethyl acetate in hexanes) to afford the racemic title product (4.1 g) as a an oil. Chiral Prep HPLC on a 2 cm×25 cm Chiracel OD column eluting with 5% isopropanol in hexanes (25 injections) afforded the (–)-enantiomer, [α]$_D$=–45.5 (MeOH, c=0.9), as the first eluting peak (R$_t$=17.5 min) and the (+)-enantiomer (1.87 g), [α]$_D$=+45.0 (MeOH, c=1.0), as the second peak (R$_t$=22.0 min).

$^1$H NMR (CDCl$_3$) δ: 2.2–2.35 (m, 2H), 2.5 (m, 1H), 2.65–2.85 (m, 2H), 2.9 (m, 1H), 3.51 and 3.68 (dABq, 2H), 4.93 (m, 2H), 6.9–7.0 (m, 2H), 7.06 (d, 1H), 7.3–7.4 (m, 1H).

Step D: (+)-trans-3-Hydroxymethyl-4-(3-fluorophenyl)cyclopentanone

A solution of (+)-trans-1-hydroxymethyl-4-methylene-2-(3-fluorophenyl)cyclopentane from Step C (1.87 g, 9.0 mmol) in methanol (75 mL) was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to rt over 2 h. The mixture was treated with 10 drops of sulfuric acid (c) in water (2 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (50% ethyl acetate in hexanes) to give the title compound (1.87 g), $[\alpha]_D=+132$ (MeOH, c=1.2).

$^1$H NMR (CDCl$_3$) δ: 2.3–2.45 (m, 2H), 2.5 (m, 1H), 2.61 and 2.77 (dABq, 2H), 2.28 (ddd, 1H), 3.61 and 3.75 (dABq, 2H), 6.9–7.0 (m, 2H), 7.06 (d, I H), 7.3–7.4 (m, 1H).

(Note: The (+)-non-racemic title compound was also prepared by essentially the same reduction of non-racemic acid from Step B.)

Step E: N-(1-(R)-3-(S)-Hydroxymethyl4-(S)-(3-fluorophenyl)cyclopent-1-yl)-D-valine t-butyl ester To a solution of (+)-trans-3-hydroxymethyl-4-(3-fluorophenyl)cyclopentanone from Step D (1.0 g, 4.8 mmol) in 1,2-dichloroethane (50 mL) was added D-valine t-butyl ester (0.90 g, 5.2 mmol) and acetic acid (0.330 mL, 5.8 mmol). After 15 min, sodium triacetoxyborohydride (2.0 g, 5.6 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with 30% ethyl acetate in hexanes to give the product (1.62 g) as a mixture of the higher R$_f$ title compound and the C-1 isomer as the free amines.

Step F: N-Methyl-N-(-(R)-3-(S)-hydroxymethyl-4-(S)-(3-fluorophenyl)cyclopent-1-yl)-D-valine t-butyl ester To a solution of N-(1-(R)-3-(S)-hydroxymethyl-4-(S)-(3-fluorophenyl)cyclopent-1-yl)-D-valine t-butyl ester from Step E (1.62, 4.44 mmol) and 37 wt % formaldehyde in water (2.1 mL, 27 mmol) in methanol (35 mL) was added 10% Pd/C (200 mg). After 10 min, the mixture was placed under hydrogen and stirred at atmospheric pressure for 60 h. The catalyst was removed by filtration and the filtrate was evaporated. The residue was purified by FC eluting with a gradient of 15 to 50% ethyl acetate in hexanes to give the higher R$_f$ title product (1.44 g) and the lower C-1 isomer (0.17 g) as the free amines.

Step G: N-Methyl-N-(1-(R)-3-(S)-formyl-4-(S)-(3-fluorophenyl)cyclopent-1-yl)-D-valine t-butyl ester To a solution of oxalyl chloride (0.235 mL, 2.65 mmol) in methylene chloride (10 mL) at −70° C. was added dropwise DMSO (0.385 mL, 5.3 mmol). After 15 min, a solution of N-methyl-N-(1-(R)-3-(S)-hydroxymethyl-4-(S)-(3-fluorophenyl)cyclopent-1-yl)-D-valine t-butyl ester (higher R$_f$ isomer from Step F) (400 mg, 1.05 mmol) in methylene chloride (10 mL) was added. The reaction was stirred at −70° C. for 1 h and then DIPEA (1.8 mL, 11 mmol) in methylene chloride (5 mL) was added dropwise over 5 min. After a further 10 min, the mixture was allowed to warm to rt for 1 h and then diluted with methylene chloride. The layers were separated. The aq. layer was reextracted with a second portion of methylene chloride and the organic layers were each washed with brine, dried over sodium sulfate, combined and concentrated in vacuo. The residue was purified by FC (15% ethyl acetate in hexanes) to give the title product (378 mg) as an oil.

Step H: N-Methyl-N-(1-(R)-3-(S)-((4-(N-(3,4-difluorobenzyloxycarbonyl)-N-(prop-1-yl)amino)piperidin-1-yl)methyl)-4-(S)-(3-fluorophenyl)cyclopent-1-yl)-D-valine t-butyl ester To a solution of N-methyl-N-(l-(R)-3-(S)-formyl-4-(S)-(3-fluorophenyl)cyclopent-1-yl)-D-valine t-butyl ester (35 mg, 0.10 mmol) from Step G in 1,2-dichloroethane (5 mL) was added 4-(N-(3,4-difluorobenzyloxycarbonyl)-N-(prop-1-yl)amino)piperidine hydrochloride (55 mg, 0.15 mmol) and DIPEA (0.025 mL, 0.15 mmol). After 15 min, sodium triacetoxyborohydride (42 mg, 0.2 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 50% ethyl acetate in hexanes to give the title product as the free amine (58 mg).

HPLC/MS (ESI): m/z 674 (M+1).

Step I: N-Methyl -N-(1-(R)-3-(S)-((4-(N- (3,4-difluorobenzyloxycarbonyl)-N-(prop- -yl)amino)piperidin-1-yl)methyl)-4-(S)-(3-fluorophenyl)cyclopent-1-yl)-D-valine tri-hydrochloride salt The N-methyl-N-(1-(R)-3-(S)-((4-(N-(3,4-difluorobenzyloxycarbonyl)-N-(prop-1-yl)amino)piperidin-1-yl)methyl)-4-(S)-(3-fluorophenyl)cyclopent-1-yl)-D-valine t-butyl ester (58 mg, 8.6 mmol) from Step H was taken up in TFA (2 mL) and aged at rt for 16 h. The volatiles were evaporated under a stream of nitrogen. The residue was taken up in methanol and absorbed onto a 1 g Varian SCX ion-exchange resin cartridge. The resin was eluted with 2×5 mL of methanol, then the product was eluted with 2×5 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, adding excess (>3-fold) 1M hydrogen chloride in ether and evaporating to dryness.

HPLC/MS (ESI): m/z 618 (M+1).

EXAMPLE 57

Using essentially the same procedure as in Example 56, Steps H and I, but the appropriate 4-substituted piperidine H, the following compounds can be prepared.

EXAMPLE 57A

N-Methyl -N-(1-(R)-3-(S)-((4-(N-(4-Nitrobenzyloxycarbonyl)-N-(prop-2-en-1-yl)amino) piperidin-1-yl)methyl)-4-(S)-(3-fluorophenyl) cyclopent-1-yl)-(D)-valine di-hydrochloride salt

EXAMPLE 57B

N-Methyl-N-(1-(R)-3-(S)-((4-(N-(4-Chlorobenzyloxycarbonyl)-N-(prop-1-yl)amino) piperidin-1-yl)methyl)-4-(S)-(3-fluorophenyl) cyclopent-1-yl)-(D)-valine di-hydrochloride salt

EXAMPLE 57C

N-Methyl -N-(1-(R)-3-(S)-((4-(N-(3-Fluorobenzyloxycarbonyl)-N-(prop-1-yl)amino) piperidin-1-yl)methyl)4-(S)-(3-fluorophenyl) cyclopent-1-yl)-(D)-valine di-hydrochloride salt

EXAMPLE 57D

N-Methyl-N-(1-(R)-3-(S)-((4-(N-(4-Fluorobenzyloxycarbonyl)-N-(prop-1-yl)amino) piperidin-1-yl)methyl)-4-(S)-(3-fluorophenyl) cyclopent-1-yl)-(D)-valine di-hydrochloride salt HPLC/MS (ESI): m/z 600 (M+1).

EXAMPLE 57E

N-Methyl-N-(1-(R)-3-(S)-((4-(N-(Benzyloxycarbonyl)-N-(prop-1-yl)amino)piperidin-1-yl)methyl)-4-(S)-(3-fluorophenyl)cyclopent-1-yl)-(D)-valine di-hydrochloride salt

EXAMPLE 58

Using essentially the same procedure as in Example 56, Steps E and I, but substituting a D or L-amino acid t-butyl ester in Step E, and/or skipping or using formaldehyde or acetaldehyde in Step F, and/or a different 4-substituted piperidine (from those prepared in Procedures 1–10) in Step H, a variety of other compounds within the scope of this patent can be prepared.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

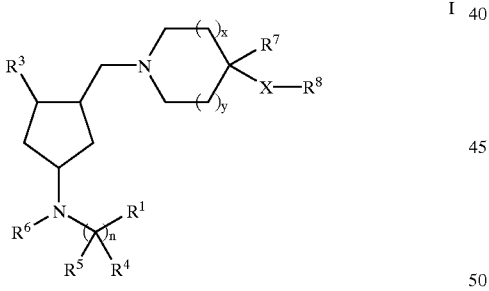

wherein:

X is —($C_{0-2}$ alkyl)-Y—($C_{0-6}$ alkyl)-,
where the alkyl is unsubstituted or substituted with 1–7 substituents where the substituents are independently selected from:
(a) halo,
(b) hydroxy,
(c) —O—$C_{1-3}$ alkyl, and
(d) trifluoromethyl,
where Y is selected from: —$NR^9(CO)O$— and —$NR^9(CO)NR^{10}$—,
where $R^9$ is independently selected from: hydrogen, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
and where $R^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl,
or where $R^9$ and $R^{10}$ may be joined together to form a 5–8 membered ring which may be unsubstituted or substituted with halo, $C_{1-3}$ alkyl, and $C_{1-3}$ alkoxy;

$R^1$ is selected from:
(1) —$CO_2H$,
(2) —$NO_2$,
(3) -tetrazolyl,
(4) -hydroxyisoxazole,
(5) —$SO_2NHCO$—($C_{0-3}$ alkyl)-$R^9$, and
(6) —$P(O)(OH)_2$;

$R^3$ is selected from the group consisting of:
phenyl and heterocycle, which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$, $R^5$ and $R^6$ are independently selected from:
hydrogen, $C_{1-10}$ alkyl, $C_{3-8}$ cycloalkyl, $C_{2-10}$ alkenyl, $C_{2-10}$ alkynyl, phenyl, —($C_{1-6}$ alkyl)-phenyl, —($C_{1-6}$ alkyl)-$C_{3-8}$ cycloalkyl, naphthyl, biphenyl, and heterocycle, which is unsubstituted or substituted with 1–7 of $R^{11}$ where $R^{11}$ is independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$,
or where $R^4$ and $R^5$ may be joined together to form a 3–8 membered saturated ring which may be unsubstituted or substituted with 1–7 of $R^{11}$,
or where $R^5$ and $R^6$ may be joined together to form a 3–8 membered saturated ring which may be unsubstituted or substituted with 1–7 of $R^{11}$;

$R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) hydroxy, and
(4) halo;

$R^8$ is selected from:
hydrogen, phenyl, naphthyl, biphenyl, and heterocycle, which is unsubstituted or substituted with 1–7 of $R^{12}$ where $R^{12}$ is independently selected from:
(a) halo,
(b) cyano,
(c) hydroxy, (d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, —$CO_2(C_{1-6}$ alkyl), phenyl, trifluoromethyl, and —$NR^9R^{10}$, (e) —O—$C_{1-6}$ alkyl, which is unsubstituted or substituted with 1–5 of $R^{13}$, (f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$;

n is an integer selected from 1, 2, 3 and 4;

x is an integer selected from 0, 1 and 2, and y is an integer selected from 0, 1 and 2, with the proviso that the sum of x and y is 2;

and pharmaceutically acceptable salts thereof and individual diastereomers thereof.

2. A compound of claim 1, wherein $R^1$ is selected from:
(1) —$CO_2H$,
(2) —$NO_2$,
(3) -tetrazolyl,
(4) -hydroxyisoxazole, and
(5) —$P(O)(OH)_2$;
and pharmaceutically acceptable salts thereof and individual diastereomers thereof.

3. A compound of claim 1, wherein $R^1$ is selected from:
(1) —$CO_2H$, and
(2) -tetrazolyl;
and pharmaceutically acceptable salts thereof and individual diastereomers thereof.

4. A compound of claim 3, wherein $R^1$ is —$CO_2H$;
and pharmaceutically acceptable salts thereof and individual diastereomers thereof.

5. A compound of claim 1, wherein $R^3$ is selected from the group consisting of phenyl and thienyl, which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl;
and pharmaceutically acceptable salts thereof and individual diastereomers thereof.

6. A compound of claim 5, wherein $R^3$ is unsubstituted phenyl, (3-fluoro)phenyl or 3-thienyl;
and pharmaceutically acceptable salts thereof and individual diastereomers thereof.

7. A compound of claim 1, wherein $R^4$ is hydrogen or $C_{1-6}$ alkyl;
and pharmaceutically acceptable salts thereof and individual diastereomers thereof.

8. A compound of claim 7, wherein $R^4$ is hydrogen;
and pharmaceutically acceptable salts thereof and individual diastereomers thereof.

9. A compound of claim 1, wherein $R^5$ is selected from hydrogen, $C_{1-6}$ alkyl, $C_{3-8}$ cycloalkyl, $C_{1-6}$ alkyl-$C_{3-8}$ cycloalkyl, and phenyl;
and pharmaceutically acceptable salts thereof and individual diastereomers thereof.

10. A compound of claim 9, wherein $R^5$ is selected from isopropyl, isobutyl, sec-butyl, and cyclohexyl;
and pharmaceutically acceptable salts thereof and individual diastereomers thereof.

11. A compound of claim 1, wherein $R^6$ is selected from hydrogen, $C_{1-6}$ alkyl, $C_{3-8}$ cycloalkyl, $C_{1-6}$ alkyl-$C_{3-8}$ cycloalkyl, and phenyl;
and pharmaceutically acceptable salts thereof and individual diastereomers thereof.

12. A compound of claim 11, wherein $R^6$ is selected from hydrogen, methyl, n-butyl, t-butyl, isobutyl, sec-butyl, —$CH_2$-cyclopropyl, —$CH_2$-cyclobutyl, and cyclohexyl;
and pharmaceutically acceptable salts thereof and individual diastereomers thereof.

13. A compound of claim 1, wherein $R^7$ is hydrogen, fluoro, hydroxy or $C_{1-6}$ alkyl;
and pharmaceutically acceptable salts thereof and individual diastereomers thereof.

14. A compound of claim 13, wherein $R^7$ is hydrogen;
and pharmaceutically acceptable salts thereof and individual diastereomers thereof.

15. A compound of claim 1, wherein X is: —Y—($C_{0-4}$ alkyl)-,
where the alkyl is unsubstituted,
where Y is selected from —$NR^9(CO)O$— and —$NR^9(CO)NR^{10}$—,
where $R^9$ is independently selected from hydrogen, $C_{1-10}$ alkyl, $C_{2-10}$ alkenyl, and $C_{1-6}$ alkyl-$C_{3-6}$ cycloalkyl, and
where $R^{10}$ is independently selected from hydrogen and $C_{1-6}$ alkyl, or where $R^9$ and $R^{10}$ may be joined together to form a 5–8 membered ring which is unsubstituted;
and pharmaceutically acceptable salts thereof and individual diastereomers thereof.

16. A compound of claim 15, wherein X is selected from —$NR^9(CO)O$—, —$NR^9(CO)OCH_2$—, —$NR^9(CO)NHCH_2$— and —$NR^9(CO)NH$—,
where $R^9$ is independently selected from methyl, ethyl, n-propyl, allyl, and —$CH_2$-cyclopropyl;
and pharmaceutically acceptable salts thereof and individual diastereomers thereof.

17. A compound of claim 1, wherein $R^8$ is phenyl which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) tetrazolyl,
(h) $C_{1-6}$ alkyl, which is unsubstituted or substituted with phenyl, and
(i) —O—$C_{1-6}$ alkyl;
and pharmaceutically acceptable salts thereof and individual diastereomers thereof.

18. A compound of claim 17, wherein $R^8$ is selected from phenyl, 4-chlorophenyl, 2-fluorophenyl, 3-fluorophenyl, 4-fluorophenyl, 2,4-difluorophenyl, 3,4-difluorophenyl, 3,5-difluorophenyl, 4-methylphenyl, 3-nitrophenyl, 4-nitrophenyl, and 4-trifluoromethylphenyl.

19. A compound of claim 1, wherein n is an integer which is 1;

and pharmaceutically acceptable salts thereof and individual diastereomers thereof.

20. A compound of claim 1, wherein x is an integer which is 1 and y is an integer which is 1;

and pharmaceutically acceptable salts thereof and individual diastereomers thereof.

21. A compound of claim 1, which is selected from the group consisting of:

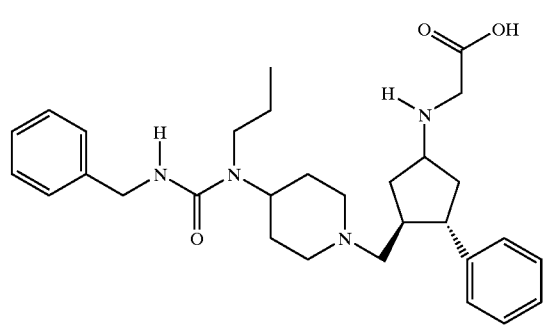

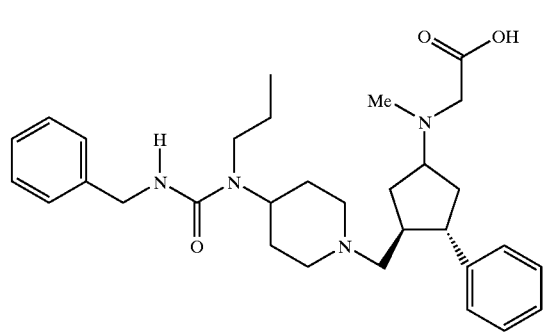

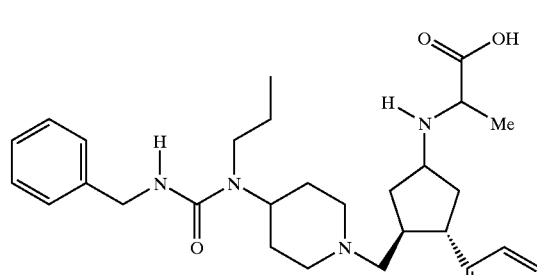

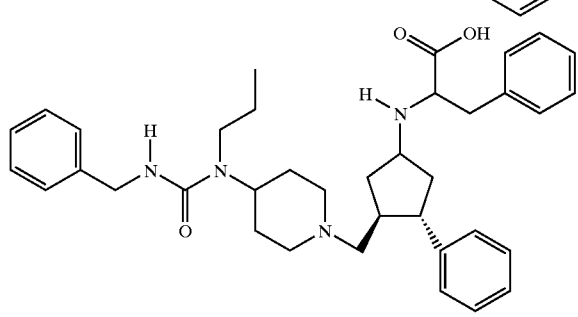

-continued

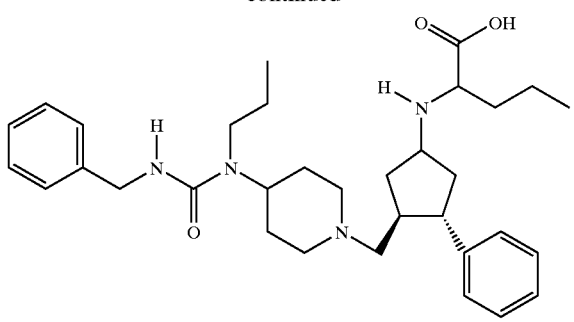

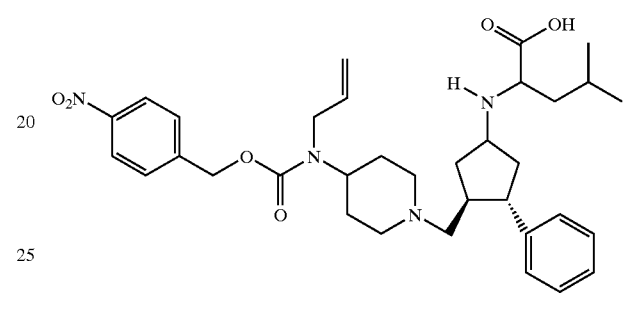

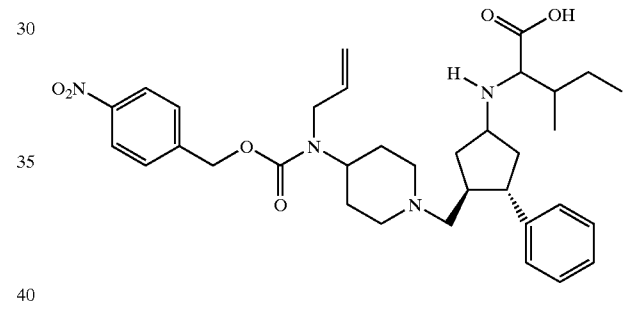

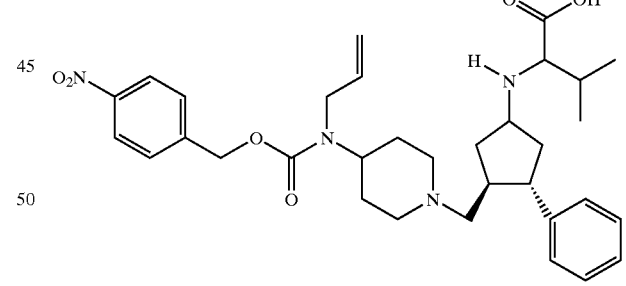

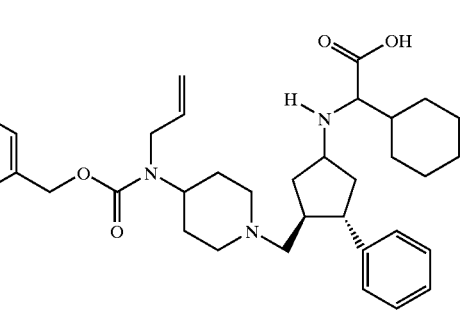

103
-continued
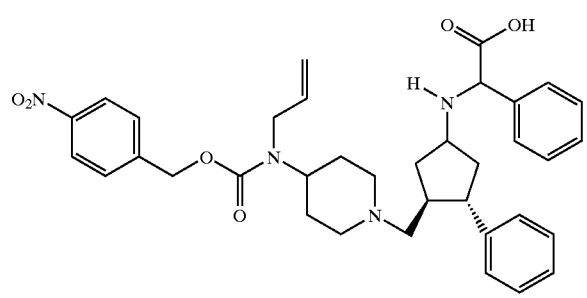
104
-continued
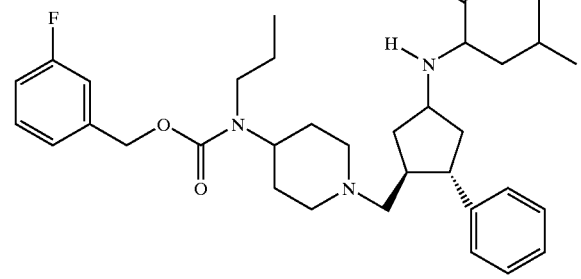
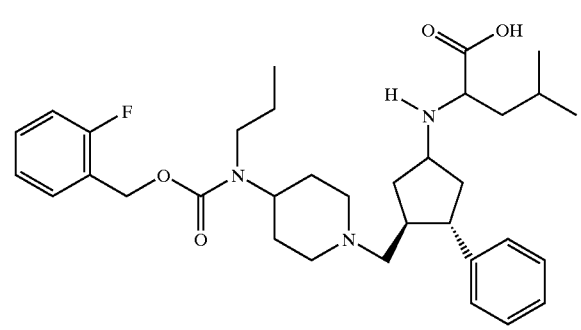
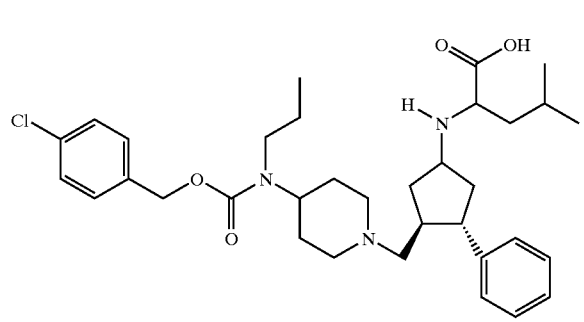
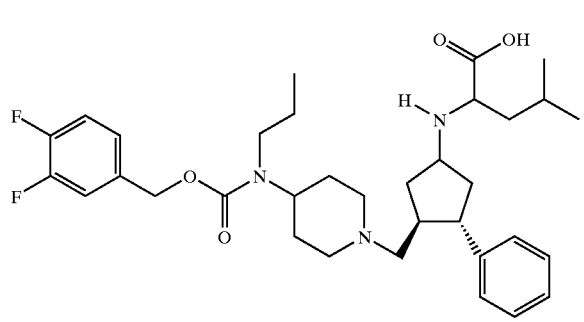
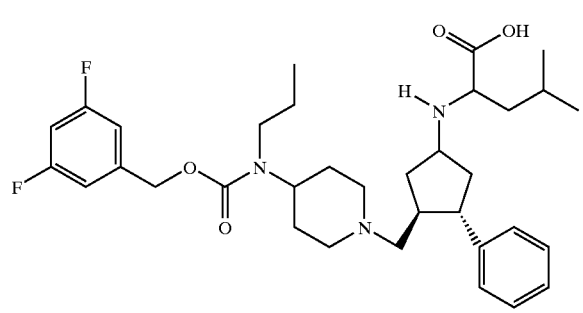

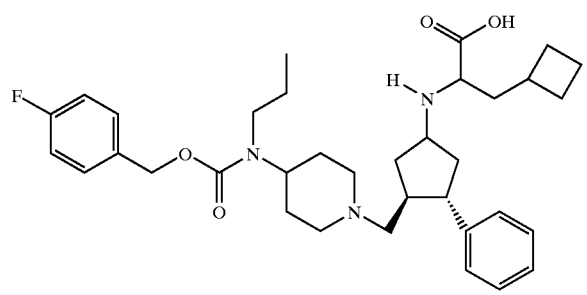
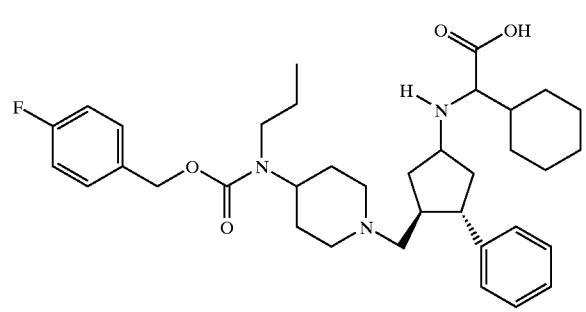
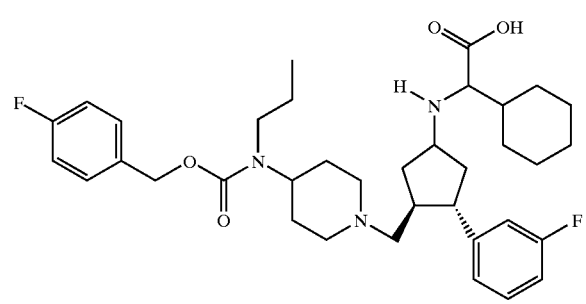
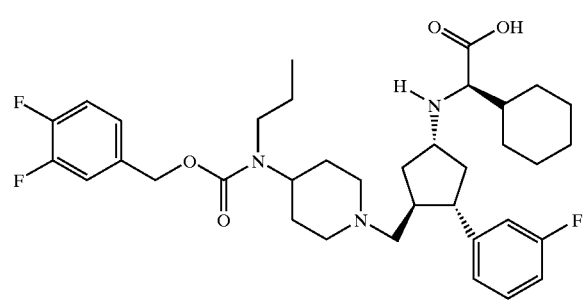
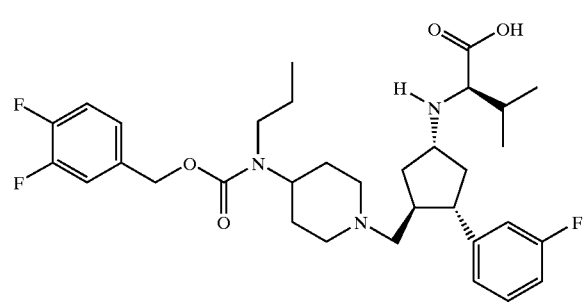
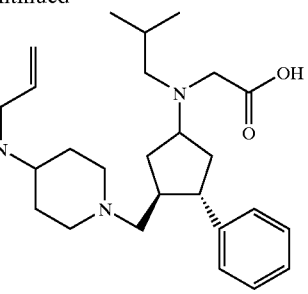
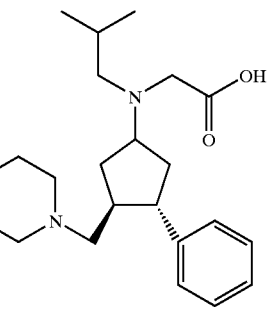
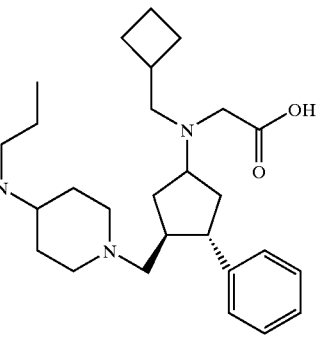
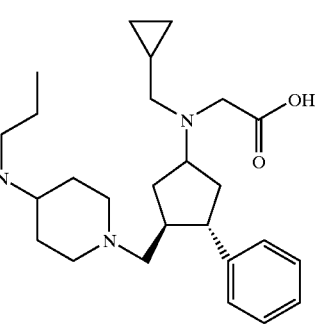
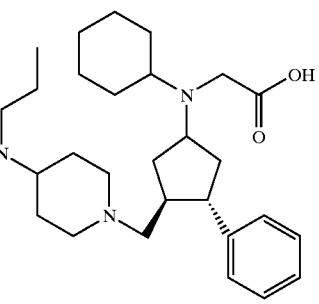

-continued

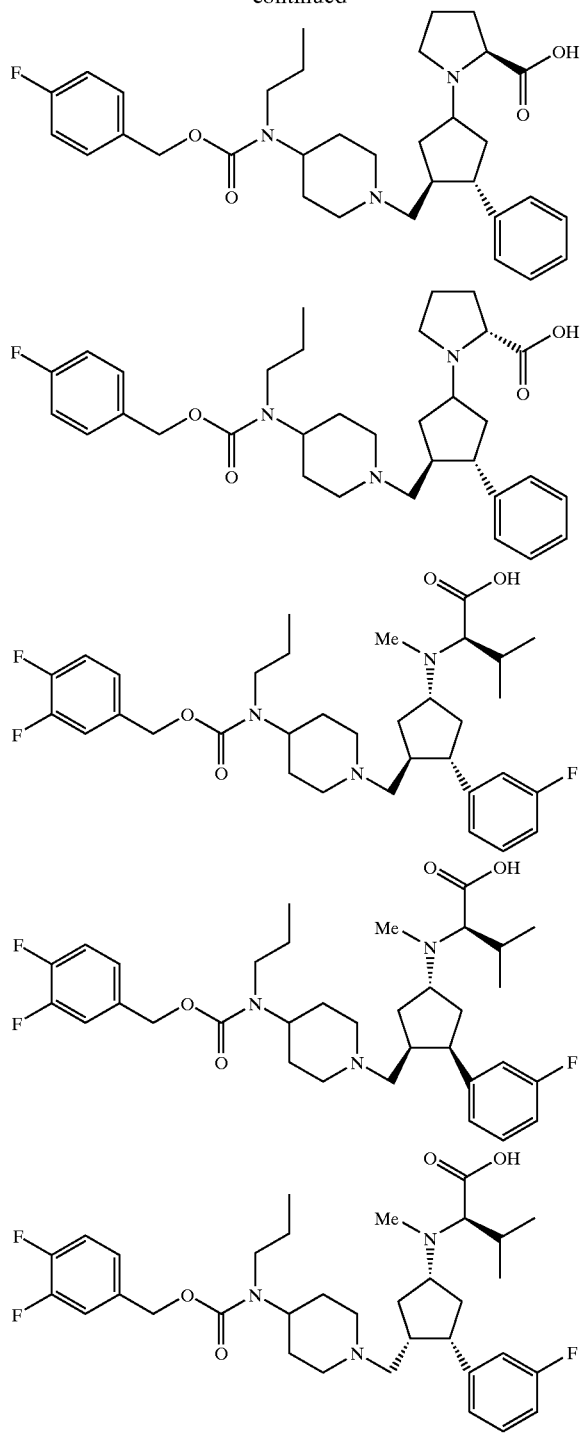

and pharmaceutically acceptable salts thereof and individual diastereomers thereof.

22. A pharmaceutical composition which comprises an inert carrier and a compound of claim 1, or a pharmaceutically acceptable salt or an individual diastereomer thereof.

23. A method for modulation of chemokine receptor activity in a mammal which comprises the administration of an effective amount of the compound of claim 1, or a pharmaceutically acceptable salt or an individual diastereomer thereof.

24. A method for treating infection by HIV, delaying of the onset of AIDS, or treating AIDS comprising the administration to a patient of an effective amount of the compound of claim 1, or a pharmaceutically acceptable salt or an individual diastereomer thereof.

25. A method for treatment of an inflammatory and immunoregulatory disorder or disease which comprises the administration to a patient of an effective amount of the compound of claim 1, or a pharmaceutically acceptable salt or an individual diastereomer thereof.

26. A method for treatment of asthma, allergic rhinitis, dermatitis, conjunctivitis, atherosclerosis or rheumatoid arthritis which comprises the administration to a patient of an effective amount of the compound of claim 1, or a pharmaceutically acceptable salt or an individual diastereomer thereof.

27. A method for blocking the entry of HIV into target cells of a patient which comprises administering to the patient in need thereof the compound of claim 1, or a pharmaceutically acceptable salt or an individual diastereomer thereof, in an amount effective to block HIV from binding to surface receptors of the target cells.

28. The method according to claim 27, wherein blocking the entry of HIV into target cells prevents infection of the patient by HIV.

29. The method according to claim 27, wherein blocking the entry of HIV into target cells prevents infectious spread of HIV in the patient.

30. The method according to claim 27, wherein blocking the entry of HIV into target cells delays the onset of AIDS in the patient.

31. The method according to claim 27, wherein blocking the entry of HIV into target cells treats the pathological conditions of AIDS in the patient.

* * * * *